US008524978B2

(12) United States Patent
Ogawa

(10) Patent No.: US 8,524,978 B2
(45) Date of Patent: Sep. 3, 2013

(54) COMPOSITION FOR PRODUCTION OF PLANT BODY HAVING IMPROVED SUGAR CONTENT, AND USE THEREOF

(75) Inventor: Kenichi Ogawa, Kyoto (JP)

(73) Assignee: Japan Science and Technology Agency, Kawaguchi (JP)

( * ) Notice: Subject to any disclaimer, the term of this patent is extended or adjusted under 35 U.S.C. 154(b) by 0 days.

(21) Appl. No.: 13/586,612

(22) Filed: Aug. 15, 2012

(65) Prior Publication Data

US 2012/0324601 A1 Dec. 20, 2012

Related U.S. Application Data

(62) Division of application No. 12/599,710, filed as application No. PCT/JP2008/070312 on Nov. 7, 2008, now Pat. No. 8,268,748.

(30) Foreign Application Priority Data

Nov. 13, 2007 (JP) ................................. 2007-294797

(51) Int. Cl.
*A01H 5/00* (2006.01)
*C12N 15/63* (2006.01)

(52) U.S. Cl.
USPC ......................................... 800/284; 435/468

(58) Field of Classification Search
None
See application file for complete search history.

(56) References Cited

U.S. PATENT DOCUMENTS

| | | |
|---|---|---|
| 5,350,689 A | 9/1994 | Shillito et al. |
| 5,595,733 A | 1/1997 | Carswell et al. |
| 5,766,900 A | 6/1998 | Shillito et al. |
| 5,770,450 A | 6/1998 | Shillito et al. |
| 5,824,302 A | 10/1998 | Carswell et al. |
| 7,479,267 B2 | 1/2009 | Ogawa et al. |
| 2003/0110527 A1 | 6/2003 | Ogawa et al. |
| 2004/0052774 A1 | 3/2004 | Creissen et al. |
| 2006/0183137 A1 | 8/2006 | Harper et al. |
| 2009/0099023 A1 | 4/2009 | Ogawa et al. |
| 2010/0016166 A1 | 1/2010 | Ogawa et al. |

FOREIGN PATENT DOCUMENTS

| | | |
|---|---|---|
| EP | 0655196 A2 | 5/1995 |
| JP | 10-271924 | 10/1998 |
| JP | 2004-352679 | 12/2004 |
| RU | 2126047 C1 | 2/1999 |
| WO | WO 2004/016726 | 2/2004 |

OTHER PUBLICATIONS

Herschnach et al (Plant Cell Physiol. 1998 39(4): 447-451).*
Examiner's Report for corresponding Australian Application No. 2008321944 dated Sep. 13, 2010.
The Notice of Allowance dated Oct. 4, 2011, for corresponding Russian Patent Application No. 2009139630, and English Translation.
Ito, H. et al. "The Sugar-Metabolic Enzymes Aldolase and Triose-Phosphate Isomerase are Targets of Glutathionylation in *Arabidopsis thaliana*; Detection using Biotinylated Glutathione", Plant Cell Physiol. (2003) 44(7); p. 655-660 (2003).
Ogawa, K. et al. "Fructose-1,6-Bisphosphate Aldolase is a Target Protein of Glutathionylation in *Arabidopsis* Chloroplasts", XP003016751, 13th International Congress on Photosynthesis, HTTP://abstracts.co.allenpress.com/pweb/pwc2004/document/?ID+39705 (2007).
Supplementary European Search Report for corresponding European Application No. 08849628, issued Dec. 15, 2011.
Wingsle, et al. "Differential redox regulation by glutathione of glutathione reductase and CuZn-superoxide Dismutase Gene Expression in Pinus Sylvestris L. needles" Planta (1996) 198: p. 151-157.
Hopkins, et al. "On Glutathione. A Thermostable Oxidation-reduction Systems" J. Biol. Chem. (1992) 54, p. 527-563.
Simoni et al. "The Discovery of Glutathione by F. Gowland Hopkins and the Beginning of Biochemistry at Cambridge University" J. Biol. Chem, vol. 277, No. 24, 2002.
Office Action dated Aug. 17, 2011, in connection with U.S. Appl. No. 12/599,710.
Office Action dated Nov. 22, 2011, in connection with U.S. Appl. No. 12/599,710.
Office Action dated Feb. 24, 2012, in connection with U.S. Appl. No. 12/599,710.
Supplementary European Search Report for corresponding European Application No. 08849628.6, mailed Dec. 22, 2011.
Japanese Office Action mailed on May 7, 2013, during prosecution of corresponding Japanese Patent Application No. 2009-541115.
Canadian Office Action mailed on Apr. 4, 2013, during prosecution of corresponding Canadian Patent Application No. 2,687,249.

\* cited by examiner

*Primary Examiner* — Medina A Ibrahim
*Assistant Examiner* — Lee A Visone
(74) *Attorney, Agent, or Firm* — Edwards Wildman Palmer LLP; David G. Conlin; Lisa Swiszcz

(57) ABSTRACT

The composition, in accordance with the present invention, for producing a plant body having an improved sugar content includes glutathione, a polynucleotide encoding γ-glutamyl-cysteine synthetase, or a polynucleotide encoding glutathione-binding plastid type fructose-1,6-bisphosphate aldolase. The composition preferably includes oxidized glutathione. This allows provision of a composition for easily producing a plant body having an improved sugar content.

1 Claim, 7 Drawing Sheets

COMPOSITION FOR PRODUCTION OF PLANT BODY HAVING IMPROVED SUGAR CONTENT, AND USE THEREOF

CROSS REFERENCE TO RELATED APPLICATIONS

This application is a divisional of U.S. patent application Ser. No. 12/599,710, filed on Nov. 11, 2009, which is a National Stage of PCT/JP2008/070312, filed on Nov. 7, 2008, which claims the benefit of Japanese Patent Application No.: 294797/2007, filed on Nov. 13, 2007, the disclosure of each of which is incorporated herein by reference in their entireties for all purposes.

TECHNICAL FIELD

The present invention relates to a composition, including a substance for regulating an oxidation-reduction state of a cell, which is for producing a plant body having an improved sugar content. The present invention also relates to use of the composition.

BACKGROUND ART

A plant such as fruit, vegetable, and cereal generally includes sugar. An amount of sugar in the plant is represented by a sugar content. The sugar content affects a commercial value of plant depending on a type of the plant. Therefore, in recent years, technical developments for increasing a sugar content of a plant have been carried out.

For example, tomatoes of high sugar content are produced mainly by soil culture. Further, a technique for producing tomatoes of high sugar content by nutrient solution culture has been suggested (Patent Literature 1).

It is known that a substance for regulating an oxidation-reduction state of a cell, such as glutathione, can function as a differentiation control agent for a cell or an organ (Patent Literature 2). Further, it is known that glutathione can function as a plant growth control auxiliary agent (Patent Literature 3).

CITATION LIST

Patent Literature 1

Japanese Patent Application Publication, Tokukaihei, No. 10-271924 (Publication Date: Oct. 13, 1998)

Patent Literature 2

International Publication WO 01/080638 (Publication Date: Nov. 1, 2001)

Patent Literature 3

Japanese Patent Application Publication, Tokukai No. 2004-352679 (Publication Date: Dec. 16, 2004)

SUMMARY OF INVENTION

However, the conventional technique for improving a sugar content of a plant lacks in simplicity. Those who can produce tomatoes of high sugar content by soil culture are limited to few specialists. Further, production of tomatoes of high sugar content by nutrient solution culture requires a specialized technique and specialized production apparatus for cultivation management.

The present invention has been accomplished in view of such circumstances, and an object of the present invention is to provide a composition for easily producing a plant having an improved sugar content and to provide a technique using the composition.

In order to attain the object, the inventors of the present invention studied diligently. As a result, they found that a sugar content of a plant body was improved in a case where the plant body was grown in a culture medium (which includes soil and a soil improvement agent) to which a substance for regulating an oxidation-reduction state of a cell is added, or in a case where the plant body was sprayed or directly coated with the substance. The present invention was accomplished based on this totally new finding and includes the following inventions.

The composition in accordance with the present invention is a composition for producing a plant body having an improved sugar content, the composition including a substance (excluding hydrogen peroxide) for regulating an oxidation-reduction state of a cell.

The composition in accordance with the present invention is preferably arranged so that the substance is glutathione, a polynucleotide encoding γ-glutamylcysteine synthetase, or a polynucleotide encoding glutathione-binding plastid type fructose-1,6-bisphosphate aldolase The composition in accordance with the present invention is preferably arranged so that the substance is oxidized glutathione.

The kit in accordance with the present invention is a kit for producing a plant body having an improved sugar content, the kit including a substance (excluding hydrogen peroxide) for regulating an oxidation-reduction state of a cell.

The production method in accordance with the present invention is a method for producing a plant body having an improved sugar content, the method including the step of cultivating the plant body by using a substance (excluding hydrogen peroxide) for regulating an oxidation-reduction state of a cell.

The present invention also includes a plant body obtained by the production method in accordance with the present invention.

Additional objects, features, and strengths of the present invention will be made clear by the description below. Further, the advantages of the present invention will be evident from the following explanation in reference to the drawings.

DESCRIPTION OF EMBODIMENTS

Figure 1:
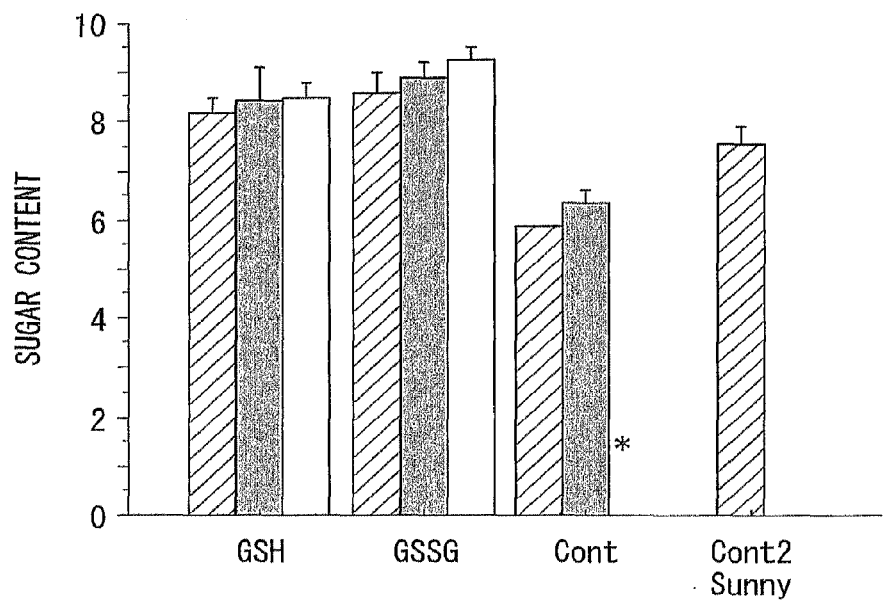
FIG. 1 illustrates a determination result of sugar content of *Lycopersicum esculentum* fruit obtained in Example 2.

1. Composition, in Accordance with the Present Invention, for Producing Plant Body Having Improved Sugar Content A composition, in accordance with the present invention, for producing a plant body having an improved sugar content (hereinafter referred to as "composition in accordance with the present invention") only has to include a substance for regulating an oxidation-reduction state of a cell.

By using the composition in accordance with the present invention, it becomes possible to easily produce a plant body having an improved sugar content. For example, the plant body can be produced in a culture medium that includes the composition in accordance with the present invention. Further, in a case where the substance for regulating an oxidation-reduction state of a cell is a polynucleotide as described later, what is necessary to do is only to introduce the polynucleotide into a plant by means of a conventional transformation technique and then grow the plant. This makes it possible to obtain the plant having an improved sugar content in an extremely simple way compared to the conventional technique such as the soil culture described above. This is because this case does not require skills, specialized techniques, specialized production apparatuses, or the like.

In the present invention, the substance for regulating an oxidation-reduction state of a cell is used for the purpose of production of a plant having an improved sugar content. This usage of the substance is new and totally differs from a conventional usage of the substance. Such an effect that the plant having an improved sugar content can be obtained could not have been expected from the conventional usage. Therefore, the present invention is accomplished based on a totally new finding by the inventors of the present invention.

In the present specification, the "plant body having an improved sugar content" is a plant body having a better sugar content than a wild strain of the plant body. In other words, the "plant body having an improved sugar content" has a higher sugar content than the wild strain. That is to say, the composition in accordance with the present invention is a composition used in production of a plant body having a higher sugar content than a wild strain. For example, by cultivating a plant body by using the composition in accordance with the present invention, it is possible to improve a sugar content of the plant body compared to a case of cultivating the plant body without the composition in accordance with the present invention. It is possible to determine a sugar content by a conventional method. It is also possible to determine a sugar content by using a conventional brix refractometer as described in Examples.

In the present specification, the "substance for regulating an oxidation-reduction state of a cell" is a substance that regulates oxidation/reduction of a substance that is responsible for oxidation-reduction of the cell. The substance for regulating an oxidation-reduction state of a cell includes substances that change values of, for example, an occurrence frequency of active oxygen, an absolute amount of glutathione, a ratio between reduced glutathione and oxidized glutathione, an absolute amount of reduced nicotinamide adenine dinucleotide phosphate (NAD(P)H), a ratio of NADPH/NADP+, a ratio of oxidized cytochrome c to reduced cytochrome c, and a ratio between oxidation and reduction of a component of electron transfer chain such as plastoquinone and ubiquinone. The substance responsible for oxidation-reduction of a cell is known in the art, but is not limited to those known in the art. The substances that change the values may be, for example, a substance that affects synthesis of glutathione or an amount of glutathione, a substance that promotes or inhibits synthesis of active oxygen, and a substance that promotes or inhibits change of a certain compound into either an oxidized form or a reduced form.

The substance, included in the composition in accordance with the present invention, for regulating an oxidation-reduction state of a cell is not limited as long as being included in the above-mentioned meaning. However, it is preferable that the substance affects synthesis of glutathione or an amount of glutathione. Such a substance makes it possible to obtain a plant having a higher sugar content.

In the present specification, the "substance that affects synthesis of glutathione or an amount of glutathione" is a substance that changes an amount of glutathione in a cell, and is preferably a substance that increases glutathione, such as glutathione itself, an enzyme for synthesis of glutathione, and a polynucleotide encoding the enzyme.

The substance for regulating an oxidation-reduction state of a cell can be classified into (i) a substance that can be absorbed into a plant by having contact with the plant and (ii) a substance that is introduced into genome of the plant. It will be understood that these substances can be used singularly or in combination.

The substance that affects synthesis of glutathione or an amount of glutathione and can be absorbed into a plant by having contact with the plant may be, for example, glutathione, glutathione conjugate, active oxygen (hydrogen peroxide, for example), active nitrogen, polyamine, oxidized titanium, jasmonic acid, salicylic acid, cysteine, cystine, heavy-metal cadmium, or iron ion. Polyamine can generate hydrogen peroxide. Oxidized titanium generates active oxygen in response to light. Cysteine and cystine are precursors of glutathione. In regard to heavy-metal cadmium and iron ion, excessive application is preferable. Among the substances exemplified above, glutathione is the most preferable to use. Glutathione includes reduced glutathione (hereinafter referred to as "GSH") and oxidized glutathione (hereinafter referred to as "GSSG"). GSSG is preferable as glutathione to be included in the composition in accordance with the present invention. As described later in Examples, use of GSSG makes it possible to obtain a plant having a higher sugar content. Further, use of GSSG makes it possible to increase the number and size of fruit.

The substance that affects synthesis of glutathione or an amount of glutathione and is introduced into genome of a plant may preferably be, for example, γ-glutamylcysteine synthetase, a polynucleotide encoding the γ-glutamylcysteine synthetase (hereinafter referred to as "GSH1 gene"), glutathione-binding plastid type fructose-1,6-bisphosphate aldolase, or a polynucleotide encoding the glutathione-binding plastid type fructose-1,6-bisphosphate aldolase (hereinafter referred to as "FBA gene").

Concrete examples of the GSH1 gene are not particularly limited, but include genes of, for example, *Zinnia elegans* (Genbank accession: AB158510), *Oryza sativa* (Genbank accession: AJ508915), and *Nicotiana tabacum* L. (Genbank accession: DQ444219). The genes of these plants can be suitably used in the present invention. Each translation product of these genes has a chloroplast transit signal peptide at its N-terminal region, like *Arabidopsis thaliana*.

In this regard, however, the following examples (a) through (d) are preferably used as the GSH1 gene in the present invention:

(a) a polynucleotide encoding a polypeptide which has the amino acid sequence of SEQ ID NO: 1 or 3;

(b) a polynucleotide encoding an polypeptide which has a γ-glutamylcysteine synthetase activity and has an amino acid sequence with deletion, substitution, or addition of one or several amino acids in the amino acid sequence of SEQ ID NO: 1 or 3;

(c) a polynucleotide having the base sequence of SEQ ID NO: 2 or 4; and (d) a polynucleotide which hybridizes under a stringent condition with a polynucleotide having a base sequence complementary to any one of the polynucleotides of the examples (a) through (c).

Note that the sequence of SEQ ID NO: 2 is an example of a base sequence encoding a polypeptide which has the amino acid sequence of SEQ ID NO: 1. Note also that the sequence of SEQ ID NO: 4 is an example of a base sequence encoding a polypeptide which has the amino acid sequence of SEQ ID NO: 3.

The FBA gene is not particularly limited, but may preferably be the following examples (e) through (h):

(e) a polynucleotide encoding a protein which has the amino acid sequence of any one of SEQ ID NO: 5, 6, and 15 through 36;

(f) a polynucleotide encoding a protein which has an activity of glutathione-binding plastid type fructose-1,6-bisphosphate aldolase and has an amino acid sequence with deletion, substitution, or addition of one or several amino acids in the amino acid sequence of any one of SEQ ID NO: 5, 6, and 15 through 36;

(g) a polynucleotide having the base sequences of SEQ ID NO: 7 and 37 through 56; and (h) a polynucleotide which hybridizes under a stringent condition with a polynucleotide having a base sequence complementary to any one of the polynucleotides of the examples (e) through (g).

The sequence of SEQ ID NO: 8 shows a cDNA sequence of a protein having the amino acid sequence of SEQ ID NO: 5. In the base sequence of SEQ ID NO: 8, the sequence from position 145 to position 147 is a start codon, and the sequence from position 1318 to position 1320 is a stop codon. That is to say, an *Arabidopsis thaliana* FBA1 gene has the sequence from position 145 to position 1320 of the base sequence of SEQ ID NO: 8 as an open reading frame (ORF).

The sequence of SEQ ID NO: 9 shows an example of a base sequence encoding a protein which has the amino acid sequence of SEQ ID NO: 6. In the sequence of SEQ ID NO: 9, the sequence from position 104 to position 1300 is a region encoding the protein which has the amino acid sequence of SEQ ID NO: 6. Note that a peptide constituted by amino acids between methionine at position 1 and alanine at position 48 of the sequence of SEQ ID NO: 6 is a chloroplast transit peptide.

The base sequence of SEQ ID NO: 7 is a base sequence serving as an ORF in the *Arabidopsis thaliana* FBA1 gene. The base sequence of the *Arabidopsis thaliana* FBA1 gene is homologous with, for example, a gene (dbj|BAB55475.1) found on genome of *Oryza sativa*.

The sequences of SEQ ID NO: 37 through 56 are examples of DNA sequences encoding the amino acid sequences of SEQ ID NO: 15 through 34, respectively.

Figure 9:
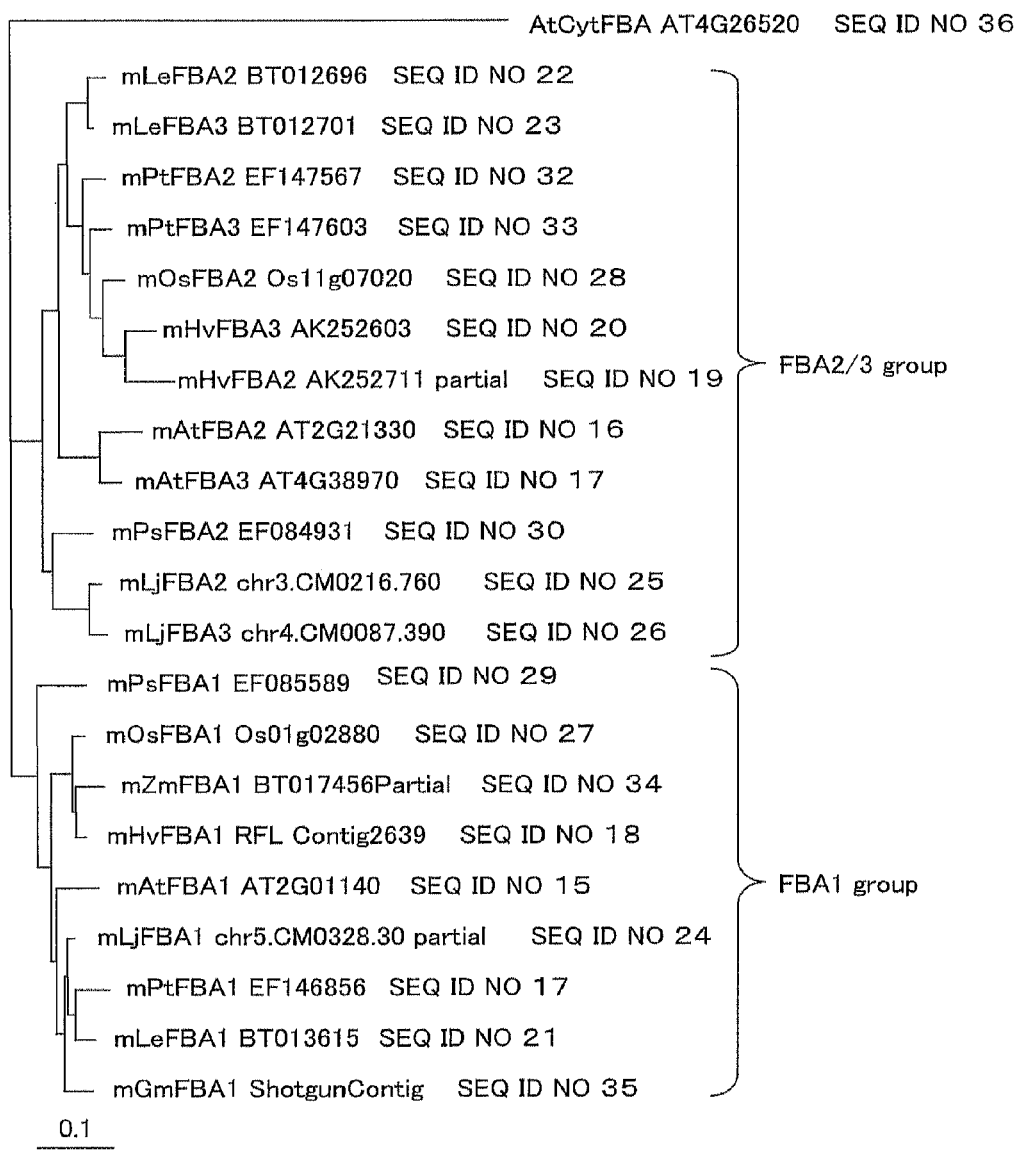
FIG. 9 is a view illustrating a genetic family tree of the genes of SEQ ID NO: 15 through 36.

For reference, FIG. 9 shows a dendrogram of the amino acid sequences of SEQ ID NO: 15 through 36.

Persons skilled in the art can easily understand that, in a case where the above-mentioned amino acid sequences or DNA sequences include a region corresponding to a chloroplast transit signal, the region can be substituted by a chloroplast transit signal of another protein.

The wording "deletion, substitution, or addition of one or several amino acids" herein means deletion, substitution, or addition of such a number of amino acid(s) (preferably 10 or less, more preferably 7 or less, further preferably 5 or less) that can be deleted, substituted, or added by means of a known method for producing a mutant peptide, such as a site-specific mutation induction method. Such a mutant protein is not limited to a protein which is artificially mutated by means of a known method for producing a mutant polypeptide, but may be a naturally-existing protein being isolated and purified.

It is known in the art that some amino acids in an amino acid sequence of a protein can be easily altered without significantly affecting a structure or function of the protein. It is also known in the art that a protein has a naturally-existing mutant which does not significantly change a structure or function of the protein, apart from an artificially-altered protein.

It is preferable that a mutant includes conservative or non-conservative substitution, deletion, or addition of amino acid(s). In this regard, silent substitution, addition, and deletion are more preferable, and conservative substitution is particularly preferable. Such mutations do not change a polypeptide activity in accordance with the present invention.

It is considered that representative examples of the conservative substitution are: substitution of one amino acid with another among aliphatic amino acids Ala, Val, Leu, and Ile; replacement of hydroxyl residues Ser and Thr; replacement of acidic residues Asp and Glu; substitution between amide residues Asn and Gln; replacement of basic residues Lys and Arg; and substitution between aromatic residues Phe and Tyr.

The "stringent condition" in the present specification means such a condition that sequences hybridize with each other only when the sequences have at least 90% identity, preferably at least 95% identity, most preferably 97% identity. Specifically, the "stringent condition" includes, for example, incubation overnight at 42° C. in a hybridization solution (50% formamide, 5×SSC (15 mM trisodium citrate and 150 mM NaCl), 50 mM sodium phosphate (pH7.6), 5×Denhardt's solution, 10% dextran sulfate, and 20 μg/ml denatured fragmented salmon sperm DNA) and washing of a filter in 0.1×SSC at approximately 65° C. The hybridization can be carried out by means of a known method such as one described in Sambrook et al., Molecular cloning, A Laboratory Manual, 3rd Ed., Cold Spring Harbor Laboratory (2001). Generally, the higher the temperature is and the lower the salt concentration is, the higher the stringency becomes (the hybridization becomes more difficult to occur). The higher stringency makes it possible to obtain a polynucleotide with a higher homology.

In a case where the composition in accordance with the present invention includes a polynucleotide among the above-mentioned polynucleotides, the composition in accordance with the present invention may include an expression vector including the polynucleotide. The expression vector may be constructed with a known method and is not particularly limited in construction method.

It is possible to use various known vectors as a base of the expression vector. For example, a plasmid, a phage, a cosmid, or the like can be used and selected as appropriate according to an introduction method or a plant cell into which the expression vector is introduced. Specifically, a pBR322 vector, a pBR325 vector, a pUC19 vector, a pUC119 vector, a pBluescript vector, a pBluescriptSK vector, a pBI vector, or the like can be used, for example. In particular, it is preferable to use a pBI binary vector in a case where the composition in accordance with the present invention is used in introducing a vector that includes the polynucleotide into a plant body by means of the *Agrobacterium* method. Specifically, the pBI binary vector may be pBIG, pBIN19, pBI101, pBI121, pBI221, or the like, for example.

In the expression vector, a promoter is not particularly limited as long as being able to express a gene in the plant body, and a known promoter can be suitably used. The promoter may be, for example, a cauliflower mosaic virus 35S promoter (CaMV35S), an actin promoter, a nopaline synthetase promoter, a tobacco PR1a gene promoter, a tomato ribulose-1,5-bisphosphate carboxylase/oxydase small subunit promoter, or the like. Among these promoters, the cauliflower mosaic virus 35S promoter or the actin promoter can be preferably used. The expression vector with each of the promoters can strongly express a given gene when introduced into a plant cell.

The promoter only has to be introduced into the vector so as to be connected so that a gene encoding a transcription factor can be expressed. The promoter is not particularly limited in specific structure as the expression vector.

The expression vector may further include a DNA segment in addition to the promoter and the polynucleotide. The DNA segment is not particularly limited and may be a terminator, a selection marker, an enhancer, a base sequence for increasing translation efficiency, and the like. Further, the expression vector may include a T-DNA region. The T-DNA region can increase efficiency of gene introduction particularly in a case where the expression vector is introduced into a plant body by means of *Agrobacterium*.

The terminator is not particularly limited as long as having a function as a transcription termination site, and may be a known terminator. Specifically, it is possible to preferably use a transcription termination site of a nopaline synthetase gene (Nos terminator), a transcription termination site of a cauliflower mosaic virus 35S (CaMV35S terminator), or the like, for example. Among these, the Nos terminator can be more preferably used. By arranging the terminator at an appropriate site in the expression vector, it becomes possible to prevent, after introduction of the expression vector into a plant body, such phenomena that an unnecessarily-long transcript is synthesized and that a strong promoter decreases the number of plasmid copies.

The selection marker may be a drug resistance gene, for example. The drug resistance gene is, for example, one resistant to hygromycin, bleomycin, kanamycin, gentamycin, chloramphenicol, or the like. With the drug resistance gene, it is possible to easily select a transformed plant by cultivating plant bodies in a culture medium that includes the above-mentioned antibiotic and thereafter selecting a plant body that can grow in the culture medium.

The polynucleotide for increasing translation efficiency may be, for example, an omega sequence derived from a tobacco mosaic virus. By arranging the omega sequence in an untranslated region (5'UTR) of a promoter, it is possible to increase translation efficiency of the gene encoding a transcription factor. As described above, various DNA segments can be included in the expression vector according to purposes.

Specifically, the expression vector is constructed by, for example, a method which the promoter, the polynucleotide, and the DNA segment, if necessary, are introduced into a base vector which is selected accordingly, so as to be arranged in a predetermined order. The polynucleotide and the promoter (and the terminator and the like, if necessary) can be connected so that an expression cassette is constructed, and the expression cassette can be introduced into the base vector. When constructing the expression cassette, it is possible to arrange so that, for example, each DNA segment includes a cleavage site as a protruding end that is complementary to a protruding end of other DNA segment, and these protruding ends are reacted via a ligation enzyme. This makes it possible to regulate an order of the DNA segments. In a case where the terminator is included in the expression cassette, the promoter, a polynucleotide encoding N-acetylglucosamine transferase, and the terminator are arranged in this order from the upstream. Reagents used in constructing the expression vector, i.e., restriction enzymes, ligation enzymes, and the like, are not particularly limited in type, and commercially available reagents can be accordingly selected and used.

The expression vector can be multiplied by a known method and a multiplication method (production method) of the expression vector is not particularly limited. In general, the expression vector is multiplied in *Escherichia coli* serving as a host. In this case, a type of *E. coli* can be selected as appropriate according to a type of the expression vector.

It is possible to singularly use the substances exemplified above and to use two or more kinds of the substances in combination.

In a case where the composition in accordance with the present invention includes, as a substance for regulating an oxidation-reduction state of a cell, a substance that can be absorbed into a plant by having contact with the plant, an amount of the substance is not particularly limited, but is preferably 0.01 mM to 20 mM, more preferably 0.1 mM to 2 mM. When the amount of the substance is within the range, it is possible to better improve a sugar content of the plant to be produced. It should be noted that the concentration of the substance may be changed as appropriate according to a desired sugar content, a type of the plant to which the substance is applied, and the like.

The composition in accordance with the present invention may include other component to such an extent that an effect of the composition in accordance with the present invention is not impaired. For example, in a case where the composition in accordance with the present invention includes, as a substance for regulating an oxidation-reduction state of a cell, a substance that can be absorbed into a plant by having contact with the plant, the composition may be dissolved in water, a known liquid carrier, or the like so as to be provided in the form of a liquid agent, an emulsion, a gel agent, or the like. Such a liquid carrier may be, for example, aromatic hydrocarbon such as xylene; alcohol such as ethanol and ethylene glycol; ketone such as acetone; ether such as dioxane and tetrahydrofuran; dimethylformamide, dimethylsulfoxide, acetonitrile, and the like, but is not limited to these. Alternatively, the substance for regulating an oxidation-reduction state of a cell may be supported by a solid carrier component so that the composition is provided as a solid agent, a powder agent, or the like. Such a solid carrier component may be, for example, an inorganic material such as talc, clay, vermiculite, diatomite, kaolin, calcium carbonate, calcium hydroxide, white clay, and silica gel; and an organic material such as flour and starch, but is not limited to these. Further, the composition in accordance with the present invention may be combined with other auxiliary agent accordingly. Such an auxiliary agent may be, for example, an anion surface-active agent such as alkyl sulfate, alkyl sulfonate, alkyl aryl sulfonate, dialkyl sulfosuccinate; a cationic surface-active agent such as higher aliphatic amine salt; a nonionic surface-active agent such as polyoxyethylene glycol alkyl ether, polyoxyethylene glycol acyl ester, polyoxyethylene glycol polyalcohol acyl ester, and cellulose derivative; a thickening agent such as gelatin, casein, and gum arabic; a weighting agent; a binding agent; and the like.

Usage of the composition in accordance with the present invention is not particularly limited. For example, in a case where the composition in accordance with the present invention includes, as a substance for regulating an oxidation-reduction state of a cell, a substance that can be absorbed into a plant by having contact with the plant, and where the composition is a liquid agent or the like, the composition may be included in a culture medium or the like which is used in cultivation of the plant, or may be sprayed, dropped, or applied to entire plant body or a part of the plant body such as a vegetative point, a bud, a leaf, and a stem. Note that a "culture medium" used in cultivation of a plant in the present specification includes soil and a soil improvement agent.

In a case where the composition is a solid agent or the like, the composition may be included in a culture medium which is used in cultivation of a plant. Alternatively, in a case of hydroponic cultivation, the composition may be added to water and gradually dissolved therein. The composition may be applied as a solid agent or the like to be dissolved in water, and dissolved in water at the time of use. Further, the composition in accordance with the present invention may be applied to a plant as a mixture with a known fertilizer and an agent such as a plant hormone.

The composition in accordance with the present invention is not particularly limited in timing of application to a plant. For example, the composition may be applied to the plant from the time of sowing. Specifically, in a case where the composition is applied to a plant such as *Lycopersicum esculentum* which produces fruit approximately 2 months to half year after sowing, the composition may be applied on the day of sowing and preferably applied in regular intervals during 30 days after sowing, more preferably during 60 days after sowing, further preferably from the day of sowing to the day of harvest. In this case, an interval of application of the composition is not particularly limited, but is preferably one to four times a week, more preferably two or three times a week. The composition is not particularly limited in applied amount. The applied amount can be arranged as appropriate according to a type of plant. In a case of *Lycopersicum esculentum* or the like, for example, preferably 0.001 mmol or more and 0.1 mmol or less, more preferably 0.01 mmol or more and 0.05 mmol or less, of the substance for regulating an oxidation-reduction state of a cell is applied at a time per plant. In a case where the composition is included in a culture medium as described above, the composition is applied to a plant from the time when the plant is sowed in the culture medium or the time when a seedling or the like of the plant is transplanted to the culture medium.

The composition in accordance with the present invention may be applied to a plant after sowing and after the plant is grown to some extent, e.g., after a seedling of the plant is produced. For example, in a case where the composition is applied to a Gramineae plant such as *Zea mays* L. var. saccharata Sturt, the composition may be applied to the plant after a seedling of the plant is grown. In this case, the composition in accordance with the present invention may be included in advance in a culture medium to which the seedling is to be transplanted, or may be periodically applied to the culture medium after the seedling is transplanted to the culture medium. In a case where the composition is applied after transplanting of the seedling, timing of the application is not particularly limited. However, it is preferable that, for example, the composition is applied one to four times a week, more preferably two or three times a week, from transplanting of the seedling until harvest. The composition in accordance with the present invention is not particularly limited in applied amount. The applied amount can be arranged as appropriate according to a type of plant. In a case of *Zea mays* L. var. saccharata Sturt or the like, for example, preferably 0.001 mmol or more and 0.1 mmol or less, more preferably 0.01 mmol or more and 0.05 mmol or less, of the substance for regulating an oxidation-reduction state of a cell is applied at a time per plant.

It is also possible to arrange timing of application of the composition in view of timing of flower production. For example, the composition may be applied while a flower bud is unbroken, after petals are fallen, from a period that the flower bud is unbroken until fruit bearing, from flowering time until fruit bearing, or from when the petals are fallen until fruit bearing. In a case where the composition is applied to *Vitis labrusca* as described later in Example, the composition may be applied to anthotaxy. In this Example, the composition is mixed with a plant hormone (gibberellin), which is for producing seedless fruit of *Vitis labrusca*, and applied when the plant hormone should be applied.

It is also possible to arrange timing of application of the composition based on back calculation of days from harvest time. For example, the composition may be applied 10 days or 20 days before harvest.

In a case where the composition in accordance with the present invention is applied to a plant during cultivation of the plant as described above, the composition may be mixed with a fertilizer and/or an agent such as a plant hormone as described above. In this case, timing of application of a mixture of the composition and the fertilizer or the like is not particularly limited, and the mixture may be applied at a time exemplified above or at a preferable time to apply the fertilizer or the like.

In a case where the composition in accordance with the present invention includes, as a substance for increasing glutathione in a cell, a substance to be introduced into genome of a plant, such as a polynucleotide described above, the composition may be used in such a way that the polynucleotide is introduced into the genome of the plant body by means of a known transformation method. For example, the composition may include a polynucleotide and may be introduced into a plant body by a known plant expression vector, or may include a vector that includes the polynucleotide.

The polynucleotide content of the composition in accordance with the present invention is not particularly limited. The polynucleotide may be dissolved in a buffer or the like which is generally used in polynucleotide preservation.

Introduction of a vector to a plant cell is carried out by a transformation method known in the art (for example, the Agrobacterium method, the particle gun, the polyethylene glycol method, and the electroporation method). In a case of the Agrobacterium method, for example, a constructed plant expression vector is introduced into suitable *Agrobacterium* (e.g., *Agrobacterium tumefaciens*) and a aseptically-cultured leaf disc is infected with this strain by the leaf disc method (Hirofumi UCHIMIYA, Manuals for plant genetic manipulation, 1990, 27-31 pp, Kodansha Scientific Ltd., Tokyo) or the like, so that a transformed plant can be obtained. In a case of the particle gun, it is possible to use (i) a plant body, plant organ, or plant tissue without any treatment, (ii) a cut piece of the plant body, plant organ, or plant tissue, or (iii) a protoplast of the plant body, plant organ, or plant tissue. Such a prepared sample can be processed using a gene introduction apparatus (e.g., PDS-1000, Bio-Rad Laboratories, Inc.). In this process, conditions differ according to a plant or a sample, however, are generally arranged so that a pressure is approximately 450 psi to 2000 psi and a distance is approximately 4 cm to 12 cm.

The cell or plant tissue into which a target gene is introduced is selected with a drug-resistance marker such as a kanamycin-resistance marker and a hygromycin-resistance marker, and then reproduced to be a plant body by a standard method. Reproduction of a plant body from a transformed cell can be carried out by a method known in the art according to a type of the plant cell.

In order to determine whether or not a target gene is introduced into a plant, it is possible to use PCR, southern hybridization, northern hybridization, or the like. For example, DNA is prepared from a transformed plant and then subjected to PCR with use of a primer specific to DNA having been introduced into the transformed plant. Then, an amplification product thus obtained is subjected to agarose gel electrophoresis, polyacrylamide gel electrophoresis, or capillary electrophoresis and thereafter stained with ethidium bromide. As a result, a target amplification product can be detected. In this way, it is possible to determine whether or not the plant is transformed.

Once a transformed plant body in which a target gene is introduced into genome is obtained, it is possible to obtain a progeny of the transformed plant body by sexual or asexual reproduction. Further, it is possible to mass-produce target plant bodies with a reproduction material (e.g., seed, protoplast) obtained from the plant body or the progeny or clone of the plant body.

In the present invention, a target plant for transformation is an entire plant body, a plant organ (for example, leaf, petal, stem, root, and seed), a plant tissue (for example, epidermis, phloem, parenchyma, xylem, vessel bundle, palisade parenchyma, sponge parenchyma), a plant culture cell, a plant cell in various forms (for example, suspension culture cell), protoplast, a cut piece of leaf, callus, or the like. The target plant for transformation is not particularly limited, and a plant capable of expressing a target gene may be selected accordingly.

The polynucleotide mentioned above is derived from *Arabidopsis thaliana*. It has been reported that, for example, transformed plants of *Nicotiana tabacum* L., *Populus, Citrus limon*, and the like can be produced with use of a gene of *Arabidopsis thaliana*. Such reports also can be used as references for how to use the composition in accordance with the present invention (Franke R, McMichael C M, Meyer K, Shirley A M, Cusumano J C, Chapple C. (2000) Modified lignin in tobacco and poplar plants over-expressing the *Arabidopsis* gene encoding ferulate 5-hydroxylase. Plant J. 22: 223-234; Pena L, Martin-Trillo M, Juarez J, Pina J A, Navarro L, Martinez-Zapater J M. (2001) Constitutive expression of *Arabidopsis* LEAFY or APETALA1 genes in citrus reduces their generation time. Nat Biotechnol. 19: 263-267).

Target plants for the composition in accordance with the present invention are not particularly limited. The composition can be applied to almost all plants such as various monocotyledonous plants, dicotyledonous plants, and trees. Examples of monocotyledonous plants include: Lemnaceae such as *Spirodela* (*Spirodela polyrhiza* Schleid) and *Lemna* (*Lemna paucicostata* and *Lemna trisulca*); Orchidaceae such as *Cattleya, Cymbidium, Dendrobium, Phalaenopsis, Vanda, Paphlopedllum* and *Oncidium*; Typhaceae; Sparganiaceae; Potamogetonaceae; Najadaceae; Scheuchzeriaceae; Alismataceae; Hydrocharitaceae; Triuridaceae; Gramineae (e.g., *Zea mays* such as *Zea mays* L. var. saccharata Sturt), Cyperaceae; Palmae; Araceae; Eriocaulaceae; Commelinaceae; Pontederiaceae; Juncaceae; Stemonaceae; Liliaceae; Amaryllidaceae; Dioscoreacea; Iridaceae; Musaceae; Zingiberaceae; Cannaceae; and *Burmannia*.

Examples of dicotyledonous plants include: Convolvulaceae such as *Pharbitis* (*Pharbitis nil* Choisy), *Calystegia* (*Calysteegia japonica* Choisy, *Calystegia hederacea* and *Calysteegia soldanella* Rohm. et Schult.), *Ipomoea* (*Ipomoea pes-caprae* and *Ipomoea batatas* Lam. var. edulis Maikno) and *Cuscuta* (*Cuscuta japonica* Chois. and *Cuscuta australis*); Caryophyllaceae such as *Dianthus* (*Dianthus caryophillus* L.), *Stellaria, Minuartia, Cerastium, Sagina, Arenaria, Moehringia, Pseudostellaria, Hankenya, Spergula, Spergularia, Silene, Lychnis, Melandryum* and *Cucubalus*; Casuarinaceae; Saururacea; Piperaceae; Choranthaceae; Sailicaceae; Myricaceae; Juglandaceae; Betulaceae; Fagaceae; Ulmaceae; Moraceae; Urticaceae; Podostemaceae; Proteaceae; Olacaceae; Santalaceae; Loranthaceae; Aristolochiaceae; Rafflesiaceae; Balanophoraceae; Polygonaceae; Chenopodiaceae; Amaranthaceae; Nyctaginaceae; Cynocrmbaceae; Phytolaccaceae; Aizoaceae; Portulacaceae; Magnoliaceae; Trochodendraceae; Cercidphyllaceae; Nymphaeaceae; Ceratophyllaceae; Ranunculaceae; Lardizabalaeae; Berberidaceae; Menispermaceae; Calycanthaceae; Lauraceae; Papaveraceae; Capparidaceae; Cruciferae; Droseraceae; Nepenthaceae; Crassulaceae; Saxifragaceae; Pittosporaceae; Hamamelidaceae; Platanaceae; Rosaceae; Leguminosae; Oxalidaceae; Geraniaceae; Linaceae; Zygophyllaceae; Rutaceae; Cimaroubaceae; Meliaceae; Polygalaceae; Euphorbiaceae; Callitrichaceae; Buxaceae; Empetraceae; Coriariaceae; Anacardiaceae; Aquifoliaceae; Celastraceae; Staphyleaceae; Icacinaceae; Aceraceae; Hippocastanaceae; Sapindaceae; Sabiaceae; Balsaminaceae; Rhamnaceae; Vitaceae; Elaeocarpaceae; Tiliaceae; Malvaceae; Stearculiaceae; Actinidiaceae; Theaceae; Guttiferae; Elatinaceae; Tamaricaceae; Violaceae; Flacourtiaceae; Stachyuraceae; Pas sifloraceae; Begoniaceae; Cactaceae; Thymelaeaceae; Elaegnaceae; Lythraceae; Punicaceae; Rhizophoraceae; Alangiaceae; Melastomataceae; Hydrocaryaceae; Oenotheraceae; Haloragaceae; Hippuridaceae; Araliaceae; Umbelliferae; Cornaceae; Diapensiaceae; Clethraceae; Pyrolaceae; Uricaceae; Myrsinaceae; Primulaceae; Plumbaginaceae; Ebenaceae; Symplocaceae; Styracaceae; Oleaceae; Loganiaceae; Gentianaceae; Apocynaceae; Asclepiadaceae; Polemoniaceae; Boraginaceae; Verbenaceae; Labiatae; Solanaceae (e.g., *Lycopersicum esculentum*); Scrophulariaceae; Bignoniaceae; Pedaliaceae; Orobanchaceae; Gesneriaceae; Lentibulariaceae; Acanthaceae; Myoporaceae; Phrymaceae; Plantaginaceae; Rubiaceae; Caprifoliaceae; Adoxaceae; Valerianaceae; Dipsacaceae; Cucurbitaceae; Campanulaceae; and Compositae.

The present invention includes a kit for producing a plant body having an improved sugar content (hereinafter referred to as "kit in accordance with the present invention"). The kit in accordance with the present invention only has to include a substance for regulating an oxidation-reduction state of a cell (for example, glutathione, a polynucleotide encoding γ-glutamylcysteine synthetase, or a polynucleotide encoding glutathione-binding plastid type fructose-1,6-bisphosphate aldolase). Further, the kit in accordance with the present invention may include a component other than the substance above. The substance for regulating an oxidation-reduction state of a cell and the component may be provided together in a single container for containing the substance and the component of an appropriate amount and/or in an appropriate form, or may be separately provided in different containers. Further, the kit in accordance with the present invention may include an instrument for plant cultivation, a culture medium, and the like. In a case where a polynucleotide is included in the kit in accordance with the present invention, the kit may be such that a base vector of an expression vector for expressing the polynucleotide may be provided in a different container from the polynucleotide. Alternatively, the kit may include the base vector into which the polynucleotide is introduced in advance. Further, the kit in accordance with the present invention may include a reagent and the like which is used in a known plant transformation method.

2. Method, in Accordance with the Present Invention, for Producing Plant Body Having Improved Sugar Content A method, in accordance with the present invention, for producing a plant body having an improved sugar content (hereinafter referred to as "method in accordance with the present invention") only has to include a step for cultivating a plant body with use of a substance for regulating an oxidation-reduction state of a cell (for example, glutathione, a polynucleotide encoding γ-glutamylcysteine synthetase, or a polynucleotide encoding glutathione-binding plastid type fructose-1,6-bisphosphate aldolase).

In a case where a substance that can be absorbed into a plant by having contact with the plant is used in regulation of an oxidation-reduction state of a cell, the step may include, for example, causing the plant to absorb the substance. How to cause the plant to absorb the substance for regulating an oxidation-reduction state of a cell is not particularly limited. For example, it is possible to cause the plant to absorb the substance by cultivating the plant on a culture medium (including soil and an soil improvement agent) that includes the substance, or by spraying or coating the plant with the substance during cultivation of the plant. Alternatively, it is also possible to cultivate the plant on a culture medium that includes absorbent such as an ion-exchange resin into which the substance is absorbed, where the absorbent is buried in soil of the culture medium, for example.

In a case where a substance such as a polynucleotide which is to be introduced into genome of a plant is used in regulation of an oxidation-reduction state of a cell, the method does not include causing the plant to absorb the substance, but may include introducing the substance to the plant in advance so as to produce a transformed plant and then cultivating the transformed plant. How to introduce a polynucleotide into the plant is described above in the explanation of the composition in accordance with the present invention.

The present invention includes a plant body obtained by the method in accordance with the present invention. It is possible to easily identify the plant body by measuring at least either a content or ratio, in the plant body, of the substance for regulating an oxidation-reduction state of a cell. Therefore, it is possible to clearly distinguish the plant body from one obtained by other method. The plant body can be identified also by, for example, comparing gene expression patterns by means of DNA microarray or the like, other than by measuring the content and concentration of the substance. In a case where GSSG is used as the substance, it is possible to take the following procedures, for example: (i) a gene expression pattern of a plant cultivated after being applied with GSSG is analyzed in advance; (ii) an expression pattern unique to the plant body applied with GSSG (GSSG expression pattern) is determined by comparison of gene expression pattern between the plant body applied with GSSG and a plant body cultivated by other method; (ii) an expression pattern of a target plant body is analyzed; and then (iv) the expression pattern of the target plant body is compared with the GSSG expression pattern. This allows an easy identification of the plant body applied with GSSG. Further, as another example of the identification, comparison of a two-dimensional electrophoretic profile of a glutathione-binding protein to a pattern change analyzed in advance makes it possible to determine whether or not GSSG is applied. In a case where a polynucleotide is used, it is possible to distinguish the plant body in accordance with the present invention from other plant body by identifying the polynucleotide in the plant body by means of PCR, southern hybridization, northern hybridization, or the like.

Details of the embodiments of the present invention are described below in Examples. It will be obvious that the present invention is not limited to the descriptions of the examples below and details of the present invention may be varied in many ways. The present invention is not limited to the description of the embodiments above, but may be altered by a skilled person within the scope of the claims. An embodiment based on a proper combination of technical means disclosed in different embodiments is encompassed in the technical scope of the present invention. All documents cited is incorporated herein by reference.

EXAMPLES

Example 1

Production of *Lycopersicum esculentum*

In the present example, *Lycopersicum esculentum* was cultivated with use of GSSG or GSH. Details of cultivation are described below.

First, *Lycopersicum esculentum* seedlings (TAKII & CO. Ltd., product name: Osama tomato reika) were transplanted into a hydroponic culture pot (1/2000 a). In the hidroponic culture pot, 6 L of vermiculite (ASAHI INDUSTRIES Co., LTD.), 3 L of KUREHA horticultural soil (KUREHA CORPORATION), and 3 L of vermiculite were layered as a lower, middle, and upper layers, respectively.

During the cultivation of *Lycopersicum esculentum*, 50 mL of 0.5 mM GSSG or 0.5 mM GSH (adjusted with 0.1N NaOH to be at pH 7) was applied twice a week at a root per plant. The *Lycopersicum esculentum* plants were grown for 60 days without being subjected to bud removal. Last 10 days was used as a harvest period for harvesting fruit of the plants. For comparison, a *Lycopersicum esculentum* plant was grown under the same condition, except that GSSG and GSH were not applied. To the plants of any condition, 3 g of Kumiai phosphorate ammonium nitrate potassium S-604 (Chisso Asahi Fertilizer Co., Ltd.) was applied as an additional fertilizer once in 2 weeks.

Next, the fruit harvested was subjected to sensory tests of sugar content and the like. As a result, it was determined that fruit of the plant applied with GSSG increased in sugar content compared to that of the plant not applied with GSSG or GSH. Further, it was determined that the plant applied with GSSG increased in number of fruit. It was determined that fruit of the plant applied with GSH increased in sugar content and acidity.

These results indicated that *Lycopersicum esculentum* having an increased sugar content could be produced by cultivation using a culture medium that contains GSSG or GSH.

Example 2

Sugar Content Determination

Cultivated were *Lycopersicum esculentum* plants to which GSSG or GSH was applied by the method described in Example 1. Then, obtained fruit of the plants was subjected to sugar content determination using "Pocket" Refractometer APAL-1 (ATAGO CO., LTD.).

For comparison, *Lycopersicum esculentum* plants were cultivated under two types of conditions (referred to as "Cont" and "Cont2 Sunny"). In the Cont condition, *Lycopersicum esculentum* plants were cultivated by the same method as in Example 1, except that GSSG and GSH were not applied. In the Cont2 Sunny condition, a *Lycopersicum esculentum* plant was not applied with GSSG or GSH and was independently cultivated at a site sufficiently irradiated with sunlight so that illuminance on the *Lycopersicum esculentum* plant becomes 100%. In the Cont condition and a condition in which GSSG or GSH was applied, the plants were planted at intervals of 40 cm to 50 cm. In this case, a plant may intercept light irradiating another plant. Therefore, illuminance on such plants becomes less than 100%.

In the condition in which GSSG was applied, the condition in which GSH is applied, and the Cont condition, three *Lycopersicum esculentum* plants were cultivated, respectively. In the Cont2 Sunny condition, one *Lycopersicum esculentum* plant was cultivated.

Figure 2:
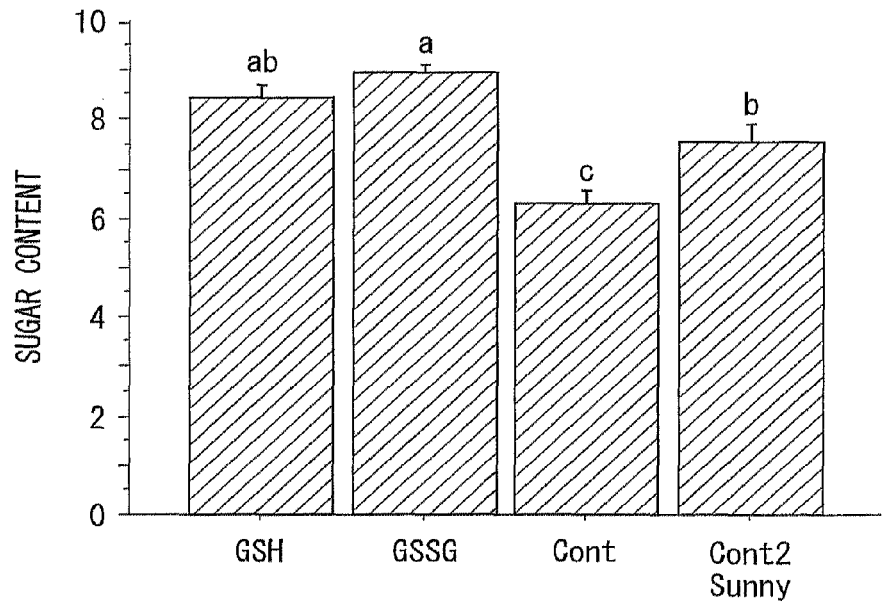
FIG. 2 illustrates a result of ANOVA analysis on the determination result of sugar content shown in FIG. 1.

FIGS. 1 and 2 show results of the sugar content determination. FIG. 1 shows a result of sugar content determination of *Lycopersicum esculentum* plants obtained in the present example. In FIG. 1, the vertical scale indicates sugar content (Brix, unit: %) and the horizontal scale indicates cultivation conditions. In FIG. 1, the reference sign * indicates that fruit could not be obtained during the harvest period. FIG. 2 shows a result of ANOVA analysis on the result of sugar content determination shown in FIG. 1. In FIG. 2, the vertical scale indicates sugar content and the horizontal scale indicates cultivation conditions. In FIG. 2, alphabetic characters above each bar are for indicating that bars indicated by a same character belong to a same group when being grouped based on ANOVA analysis. The ANOVA analysis was carried out by means of StatView 5.0 (SAS Institute Inc.) with a significant difference level of 5%.

As shown in FIGS. 1 and 2, application of GSSG or GSH made it possible to obtain *Lycopersicum esculentum* fruit which was significantly increased in sugar content compared to *Lycopersicum esculentum* fruit cultivated under the Cont condition and also to *Lycopersicum esculentum* fruit sufficiently irradiated with sunlight. Especially, application of GSSG made it possible to obtain *Lycopersicum esculentum* having an extremely high sugar content.

Example 3

Production of *Zea mays* L. var. Saccharata Sturt

In the present example, *Zea mays* L. var. saccharata Sturt was cultivated. First, a *Zea mays* L. var. saccharata Sturt seed (TAKII & CO. Ltd., product number: Canberra 90) was sown in vermiculite (ASAHI INDUSTRIES Co., LTD.). Two weeks after sowing, a *Zea mays* L. var. saccharata Sturt plant was transplanted to a hydroponic culture pot described in Example 1. To the plant, 3 g of Kumiai phosphorate ammonium nitrate potassium S-604 (Chisso Asahi Fertilizer Co., Ltd.) was applied as an additional fertilizer 4 weeks and 6 weeks after the sowing.

Within 2 weeks from the 5th week after the sowing, 50 mL of 0.2 mM GSSG was applied 4 times at a root of the plant. Within 2 weeks from the 7th week after the sowing, 50 mL of 0.2 mM GSSG was sprayed 4 times to leaves of the plant. For comparison, a *Zea mays* L. var. saccharata Sturt plant was cultivated by the same method as in the present example, except that GSSG was not applied, and fruit thereof was harvested.

Fruit was harvested 90 days after the sowing and subjected to a sensory test of sugar content. As a result, it was determined that fruit of the plant applied with GSSG increased in sugar content compared to that of the plant applied with no GSSG. Further, it was determined that the plant applied with GSSG increased in size and number of fruit.

Example 4

Production of *Zea mays* L. var. Saccharata Sturt (2)

In the present example, *Zea mays* L. var. saccharata Sturt was cultivated under a condition different from Example 3 in how to apply GSSG. First, a *Zea mays* L. var. saccharata Sturt seed (TAKII & CO. Ltd., product number: Canberra 90) was sown in vermiculite (ASAHI INDUSTRIES Co., LTD.). One week after sowing, a *Zea mays* L. var. saccharata Sturt plant was transplanted to a hydroponic culture pot described in Example 1. To the plant, 3 g of Kumiai phosphorate ammonium nitrate potassium S-604 (Chisso Asahi Fertilizer Co., Ltd.) was applied as an additional fertilizer 4 weeks and 6 weeks after the sowing.

During 12 weeks after germination, 200 mL of 0.5 mM GSSG was applied at a root of the plant twice a week. For comparison, a *Zea mays* L. var. saccharata Sturt plant was cultivated by the same method as in the present example, except that GSSG was not applied, and fruit thereof was harvested.

Fruit was harvested 12 weeks after the sowing and subjected to a sensory test of sugar content. As a result, it was determined that fruit of the plant applied with GSSG increased in sugar content compared to that of the plant applied with no GSSG. Further, it was determined that the plant applied with GSSG increased in size and number of fruit.

Example 5

Production of *Vitis labrusca*

In the present invention, *Vitis labrusca* was cultivated. Specifically, immediately after flowering of a *Vitis labrusca* (Delaware) plant, a mixed solution of 1 mM gibberellin (GA3) and 1 mM of an agent was applied to anthotaxy of the plant. The agent was GSSG or GSH. Then, the plant was coated with the agent and thereafter produced fruit was harvested. For comparison, a *Vitis labrusca* plant was cultivated in the same way, except that GA3, but not GSSG or GSH, was applied, and fruit thereof was harvested and subjected to a sensory test described below.

The fruit harvested was subjected to a sensory test of sugar content. As a result, it was determined that fruit of the plant applied with GA3 and GSSG or GSH increased in sugar content compared to that of the plant applied with only GA3. Further, it was determined that the plant applied with GSSG and GA3 increased in size of fruit.

In addition, it was determined that a *Vitis labrusca* plant applied with GSSG or GSH but not GA3 increased in sugar content. In this case, effect of producing seedless grape was suppressed without GA3.

Example 6

Change Over Time after Application of Substance for Regulating Oxidation-Reduction State of Cell In the present example, a sugar content of a plant was determined after a substance for regulating an oxidation-reduction state of a cell was applied to the plant. The substance for regulating an oxidation-reduction state of a cell was GSH or GSSG. As in the case of Example 1, *Lycopersicum esculentum* was used as the plant. Specifically, the following operations were carried out.

Figure 3:
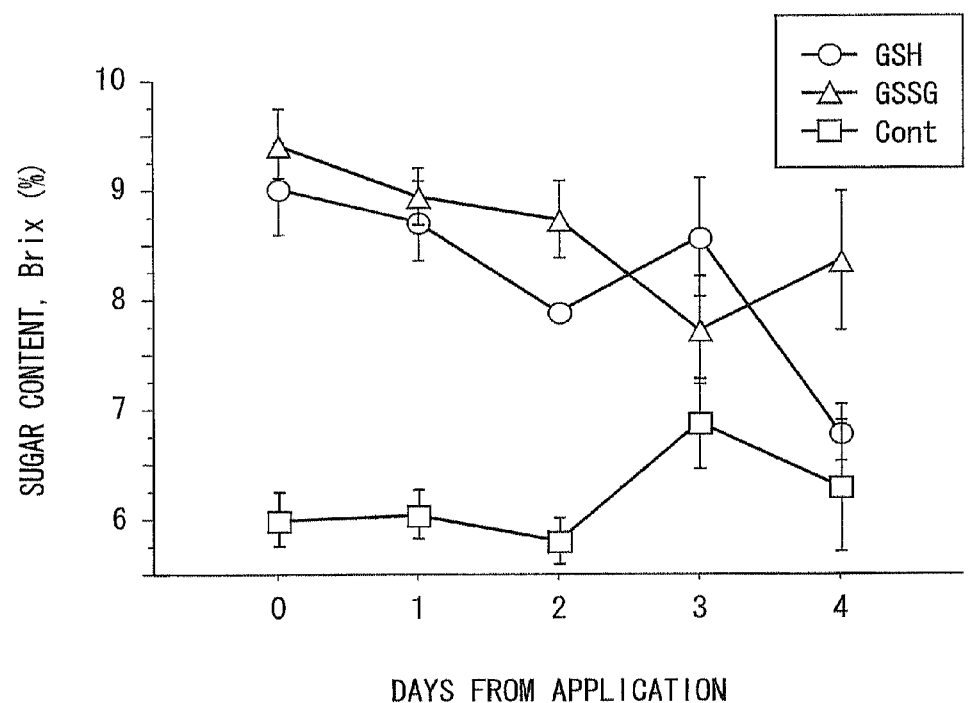
FIG. 3 is a view illustrating a determination result of relation between sugar content and the number of days from a treatment day of GSSG or GSH.

Ninety days after sowing of *Lycopersicum esculentum* seeds, *Lycopersicum esculentum* plants were subjected to a GSH or GSSG treatment. The *Lycopersicum esculentum* plants were cultivated by the same method as in Example 1 except for the GSH or GSSG treatment. The GSH or GSSG treatment was such that 50 mL of 0.5 mM GSSH or 0.5 mM GSH (adjusted with 0.1N NaOH to be at pH 7) was applied once at a root per plant. Then, fruit of the plants was harvested every day from the 0th day until the 4th day after application of GSH or GSSG, and subjected to sugar content determination. FIG. 3 shows a result of the sugar content determination. FIG. 3 is a graph showing a determination result of relation between sugar content and the number of days from an application day of GSH or GSSG. In FIG. 3, the vertical scale indicates sugar content (Brix, unit: %) and the horizontal scale indicates days from the application day. In FIG. 3, lines labeled with circles, triangles, and squares show results of the plants applied with GSH, GSSG, and no GSH and no GSSG, respectively. Note that GSSG or GSH was applied in the morning of the 0th day, and a result of the 0th day in FIG. 3 was obtained by harvesting fruit and determining a sugar content of the fruit in the evening of the 0th day.

As shown in FIG. 3, it was shown that application of GSSG or GSH made it possible to rapidly improve a sugar content of fruit.

Example 7

Production of Plant Into which GSH1 Gene is Introduced

In the present example, a clone of a γ-glutamylcysteine synthetase gene was used as a substance for regulating an oxidation-reduction state of a cell. The clone is a polynucleotide having a sequence of SEQ ID NO:3, is one of GSH1 genes, and is referred to merely as "GSH1 gene" in the present example.

(1) Plant to be Used

In order to produce a transformed plant, a wild type *Arabidopsis thaliana* Columbia (Col-0) was used as a parent plant. The Columbia (Col-0) was sown in soil in a square plastic pot (6.5×6.5×5 cm), which soil is constituted by three layers of vermiculite (ASAHI INDUSTRIES Co., LTD., Okayama), KUREHA culture soil (KUREHA horticultural soil, KUREHA CORPORATION, Tokyo), and vermiculite being layered in this order from the bottom at a ratio of 2:1:1. Then, the Columbia (Col-0) was cultivated at a growth temperature of 22° C. under a long-day condition (16-hour light period/8-hour dark period).

(2) Cloning of GSH1 Gene, Alteration of GSH1 Gene, and Production of GSH1-Transformed Plant Entire RNA of a 3-week-old wild type *Arabidopsis thaliana* Columbia (Col-0) was isolated, and cDNA was synthesized based on the RNA by using a Prostar first strand RT-PCR kit (Stratagene, La Jolla, Calif., USA).

With use of the following specific primers designed based on a cDNA sequence of a GSH1 gene, a full-length cDNA was amplified as two fragments by PCR:

```
                                           (SEQ ID NO: 10)
GSH1_5'-3:  5'-GCTTTCTTCTAGATTTCGACGG-3'

(SEQ ID NO: 11)
GSH1_3'-3:  5'-CCTGATCATATCAGCTTCTGAGC-3'

(SEQ ID NO: 12)
GSH1_5'-2:  5'-ATGCCAAAGGGGAGATACGA-3'

(SEQ ID NO: 13)
GSH1_3'-2:  5'-GGAGACTCGAGCTCTTCAGATAG-3'.
```

Then, subcloning was carried out so that each of the fragments was inserted into a pGEM-T Easy vector (Promega, Madison, Wis., USA). The primers GSH1__5'-3 and GSH1__3'-2 respectively includes XbaI and SacI cleavage sites required for introduction of the fragments to a binary vector pBI121 used in plant transformation.

The two fragments were fused with each other at a KpnI cleavage site, so that a vector (Ch1.GSH1-pGEM) including the full-length cDNA was constructed. The Ch1.GSH1-pGEM was treated with restriction enzymes XbaI and SacI and a fragment thus obtained was substituted with a region of a binary vector pBI121, which region encodes β-glucuronidase (GUS) and is located downstream of a cauliflower mosaic virus 35S promoter. As a result, a construct (35S-Ch1.GSH1-pBI121) for producing the transformed plant was produced.

There is only one copy of the GSH1 gene in genome of *Arabidopsis thaliana*, and the GSH1 gene includes a chloroplast transit signal. For the purpose of accumulating GSH1 gene products (γ-glutamylcysteine synthetase) in cytoplasm, produced was a construct (35S-cyt.GSH1-pBI121) for expressing a protein in which the 73rd amino acid from an N-terminal, which amino acid was presumed to be the chloroplast transit signal, was deleted and an alanine residue at the $74^{th}$ position from the N-terminal was substituted with a methionine residue. First, PCR was performed with the primer GSHI__3'-3 and the following primer GSH1(cyt.)__5' (a base substitution site is underlined) in which the alanine residue at the 74th position from the N-terminal was substituted with the methionine residue and an XbaI cleavage site was inserted upstream of the $74^{th}$ position:

```
                                           (SEQ ID NO: 14)
GSH1(cyt.)_5':  5'-AGGGCATCTAGAGACCATGGCAAGTCC-3'.
```

Then, a fragment thus obtained was treated with restriction enzymes XbaI and KpnI. Thereafter, subcloning was carried out so that the fragment was inserted into a pBluescript vector (Stratagene, La Jolla, Calif. USA) (cyt.GSH-1pBS). The cyt.GSH1-pBS was treated with the restriction enzymes XbaI and KpnI, and a fragment thus obtained was substituted with a XbaI-KpnI fragment of the 35S-Ch1.GSH1-pBI121. As a result, the 35S-cyt.GSH1-pBI121 was produced.

The two types of expression vectors produced as above, i.e., the 35S-Ch1.GSH1-pBI121 and the 35S-cyt.GSH1-pBI121, were introduced into the Col-0 by the *Agrobacterium* method (Clough, S. J. and SH1-pB Bent, A. F. (1998) Floral dip: A simplified method for *Abrobacterium*-mediated transformation of *Arabidopsis thaliana*. Plant J. 16: 735-743). As a result, a transformed plant was produced.

Specifically, selection of the transformed plant was repeated on an agar medium (Murashige-Skoog medium of a half concentration) which contains kanamycin serving as a selection marker, until such a generation occurred that all seeds exhibit kanamycin resistance (a generation does not exhibit divergence). In process of the selection, it was determined that characters of the kanamycin resistance were diverged at a ratio of 3:1 and that the expression vectors were introduced into at least single chromosome.

The plant obtained as above is hereinafter referred to as "35S-GSH1".

(3) Sugar Content Determination

A 35S-GSH1 and a wild type *Arabidopsis thaliana* (Col-0) for comparison were cultivated at a growth light intensity of 50 $\mu Em^{-2}s^{-1}$ or 500 $\mu Em^{-2}s^{-1}$. After one-week cultivation, each plant body was collected. Then, each plant body was frozen with liquid nitrogen, ground into powder, and thereafter subjected to extraction using 100 μl of 50 mM sodium acetate buffer per 50 mg of plant body.

Figure 4:
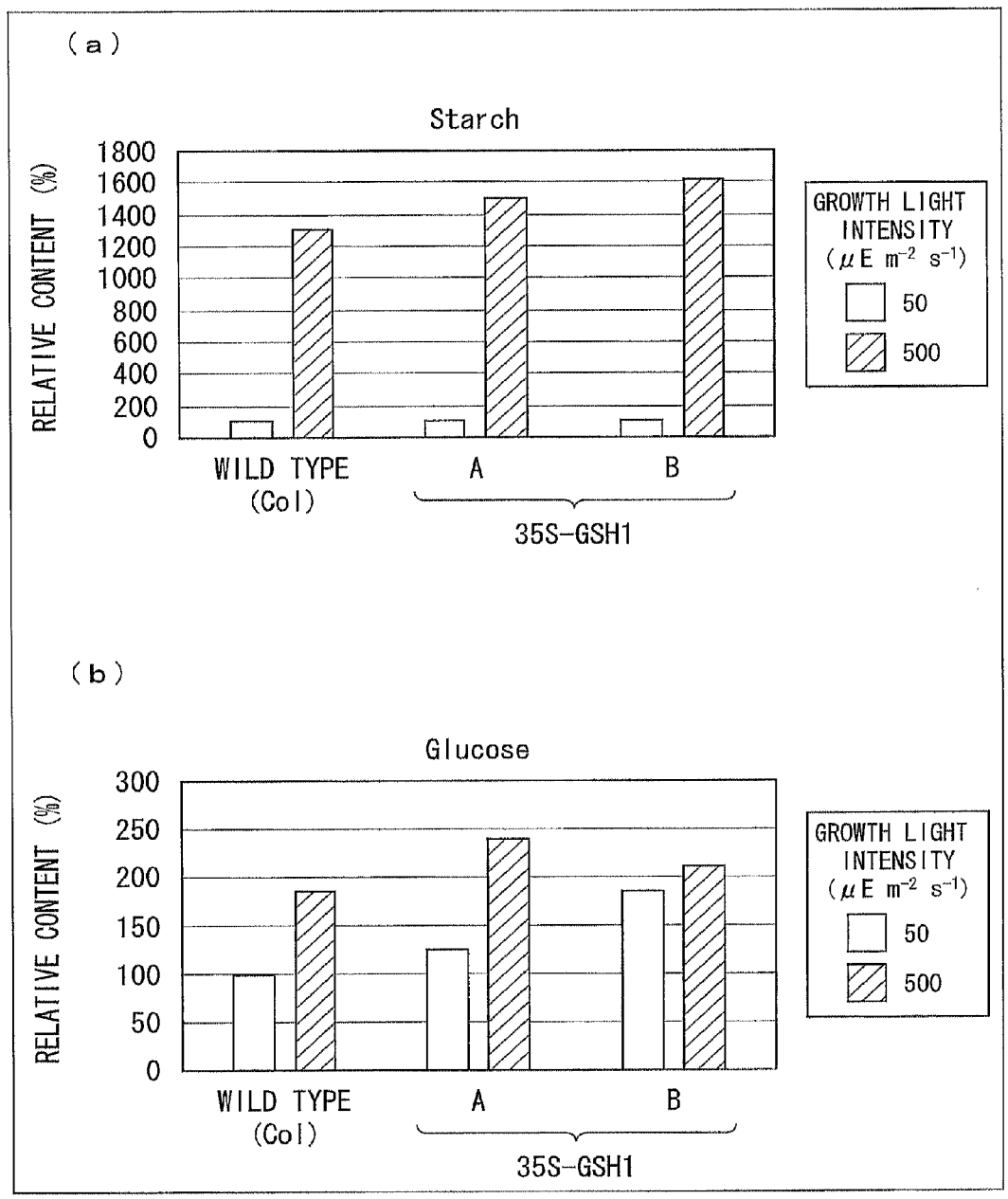
FIG. 4 illustrates a determination result of starch and glucose of 35S-GSH1.

Next, a glucose content and a starch content of each extract thus obtained were determined. The glucose content was determined using Glucose CII-Test Wako (Wako Pure Chemical Industries, Ltd.). The starch content was determined by mixing the extract with 35 Units/ml amyloglucanase and a sodium acetate buffer (50 mM, pH4.5), leaving at rest the resulting mixture for 1 hour, and then determining an amount of glucose. Results of determination are shown in FIG. 4. FIG. 4 shows determination results of starch and glucose contents of 35S-GSH1. In FIG. 4, (a) shows starch contents, and (b) shows glucose contents. In (a) and (b) of FIG. 4, the vertical scales indicate relative contents of starch and glucose, respectively, and the horizontal scales indicate types of plants. A and B shown in FIG. 4 are results of the 35S-GSH1. In the present example, two 35S-GSH1 plants were used in an experiment as A and B shown in FIG. 4. The term "relative content" above means a relative amount where an amount in the Col-0 cultivated at a growth light intensity of 50 $\mu Em^{-2}s^{-1}$ is 100.

As shown in FIG. 4, the 35S-GSH1 had a higher starch content and a higher sugar content than the Col-0.

Example 8

Production of *Prunus avium*

In the present example, *Prunus avium* was cultivated. Specifically, 4 weeks and 3 weeks before an expected date of harvesting *Prunus avium* (Napoleon) fruit, a surface of a leaf on a branch having the fruit to be harvested was coated with 0.5 mM GSSG. The fruit was harvested on the expected date.

Figure 5:
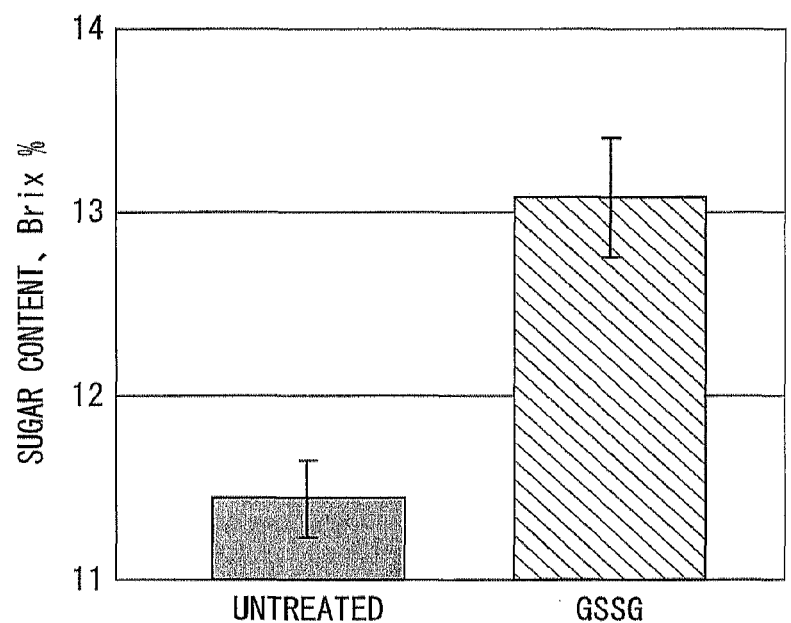
FIG. 5 illustrates a determination result of sugar content of *Prunus avium* fruit obtained in Example 8.

Next, the fruit harvested was subjected to a sensory test of sugar content. As a result, it was determined that the fruit applied with GSSG increased in sugar content and decreased in acidity. Further, it was determined that the fruit applied with GSSG increased in weight. Furthermore, the fruit obtained was subjected to sugar content determination using "Pocket" Refractometer APAL-1 (ATAGO CO., LTD.). For comparison, fruit applied with no GSSG was also subjected to the sugar content determination. FIG. 5 shows a result of determination of sugar content of *Prunus avium* fruit obtained in the present example. In FIG. 5, the vertical scale indicates sugar content (Brix, unit: %). Further, an ANOVA analysis was carried out by using StatView5.0 (SAS Institute Inc.) with a significant difference level of 5%. As a result, a significant difference was shown.

As described above, application of GSSG made it possible to obtain *Prunus avium* fruit having a significantly improved sugar content.

Example 9

Production of *Citrus unshiu*

In the present example, *Citrus unshiu* was cultivated. Specifically, one week before an expected date of harvesting *Citrus unshiu* fruit, a surface of a leaf on a branch having the fruit to be harvested was coated with 0.5 mM GSSG. The fruit was harvested on the expected date.

Figure 6:
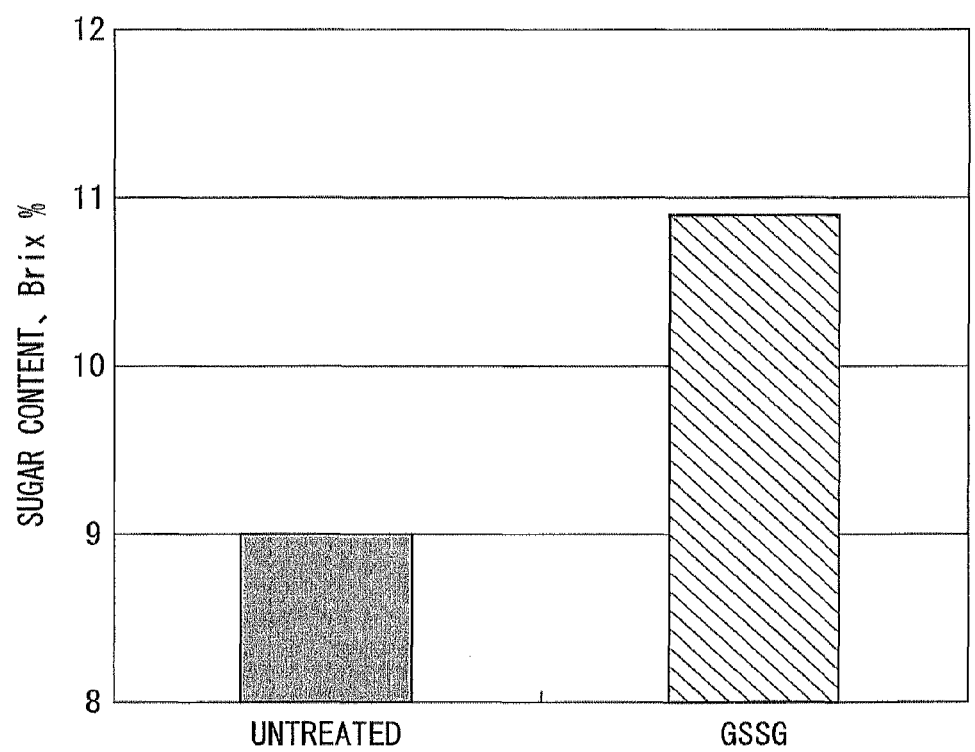
FIG. 6 illustrates a determination result of sugar content of *Citrus unshiu* fruit obtained in Example 9.

Next, the fruit harvested was subjected to a sensory test of sugar content. As a result, it was determined that the fruit applied with GSSG increased in sugar content and decreased in acidity. Further, it was determined that the fruit applied with GSSG increased in weight. Furthermore, the fruit obtained was subjected to sugar content determination using "Pocket" Refractometer APAL-1 (ATAGO CO., LTD.). For comparison, fruit applied with no GSSG was also subjected to the sugar content determination. FIG. 6 shows a result of determination of sugar content of *Citrus unshiu* fruit obtained in the present example. In FIG. 6, the vertical scale indicates sugar content (Brix, unit: %). Further, an ANOVA analysis was carried out by using StatView5.0 (SAS Institute Inc.) with a significant difference level of 5%. As a result, a significant difference was shown.

As described above, application of GSSG made it possible to obtain *Citrus unshiu* fruit having a significantly improved sugar content.

Example 10

Production of *Fragaria ananassa*

In the present example, *Fragaria ananassa* was cultivated with use of GSSG or GSH. Details of cultivation are described below.

First, *Fragaria ananassa* seedlings were transplanted to a planter. In the planter, 6 L of vermiculite (ASAHI INDUSTRIES Co., LTD.), 3 L of KUREHA horticultural soil (KUREHA CORPORATION), and 3 L of vermiculite were layered as a lower, middle, and upper layers, respectively.

During cultivation of *Fragaria ananassa* plants, 50 mL of 0.2 mM or 0.5 mM GSSG or 50 mL of 0.4 mM or 0.5 mM GSH (adjusted with 0.1N NaOH to be at pH7) was applied once a week at a root per plant. The plants were grown for 63 days without being subjected to bud removal. For comparison, a *Fragaria ananassa* plant was grown under the same condition, except that GSSG and GSH were not applied. To the plants of any condition, 3 g of Kumiai phosphorate ammonium nitrate potassium S-604 (Chisso Asahi Fertilizer Co., Ltd.) was applied as an additional fertilizer once in 2 weeks.

Next, the fruit harvested was subjected to sensory tests of sugar content and the like. As a result, it was determined that fruit of the plant applied with GSSG increased in sugar content and decreased in acidity compared to that of the plant not applied with GSSG or GSH. Further, it was determined that the plant applied with GSSG increased in number of fruit. It was also determined that fruit of the plant applied with GSH increased in sugar content and acidity.

Figure 7:
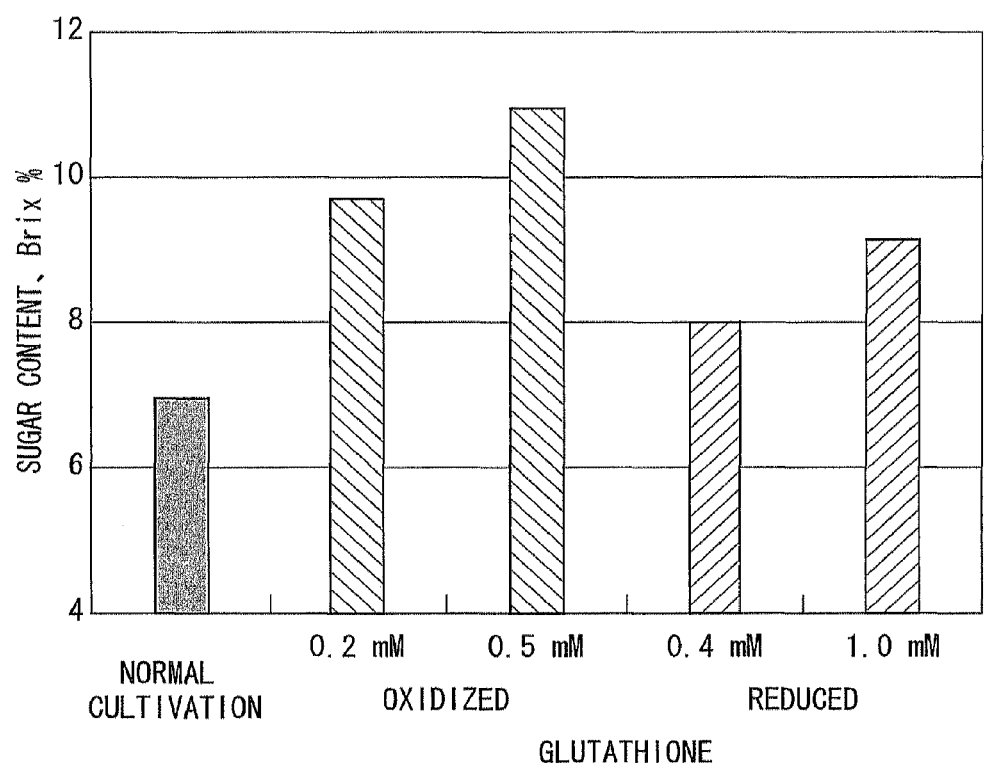
FIG. 7 illustrates a determination result of sugar content of *Fragaria ananassa* fruit obtained in Example 10.

Further, the fruit obtained was subjected to sugar content determination using "Pocket" Refractometer APAL-1 (ATAGO CO., LTD.). For comparison, fruit not applied with GSSG or GSH was also subjected to the sugar content determination. FIG. 7 shows a result of determination of sugar content of *Fragaria ananassa* fruit obtained in the present example. In FIG. 7, the vertical scale indicates sugar content (Brix, unit: %). Further, an ANOVA analysis was carried out by using StatView5.0 (SAS Institute Inc.) with a significant difference level of 5%. As a result, a significant difference was shown.

These results indicated that *Fragaria ananassa* fruit having an increased sugar content could be produced by cultivation using a culture medium that contains GSSG or GSH.

Example 11

Production of *Zea mays* L. var. Saccharata Sturt

In the present example, *Zea mays* L. var. saccharata Sturt was cultivated. First, a *Zea mays* L. var. saccharata Sturt seed (TAKII & CO. Ltd., product number: Canberra 86) was sown in vermiculite (ASAHI INDUSTRIES Co., LTD.). Two weeks after sowing, a *Zea mays* L. var. saccharata Sturt plant was transplanted to a hydroponic culture pot described in Example 1. To the plant, 3 g of Kumiai phosphorate ammonium nitrate potassium S-604 (Chisso Asahi Fertilizer Co., Ltd.) was applied as an additional fertilizer 4 weeks and 6 weeks after the sowing.

In the 5th, 6th, 7th, and 8th week after the sowing, 0.5 mM GSSG (dissolved in 0.1% Tween80 serving as a spreading agent) was sprayed onto a leaf surface. For comparison, a *Zea mays* L. var. saccharata Sturt plant was cultivated by the same method as in the present example, except that Tween80, but not GSSG, was applied, and fruit thereof was harvested.

Figure 8:
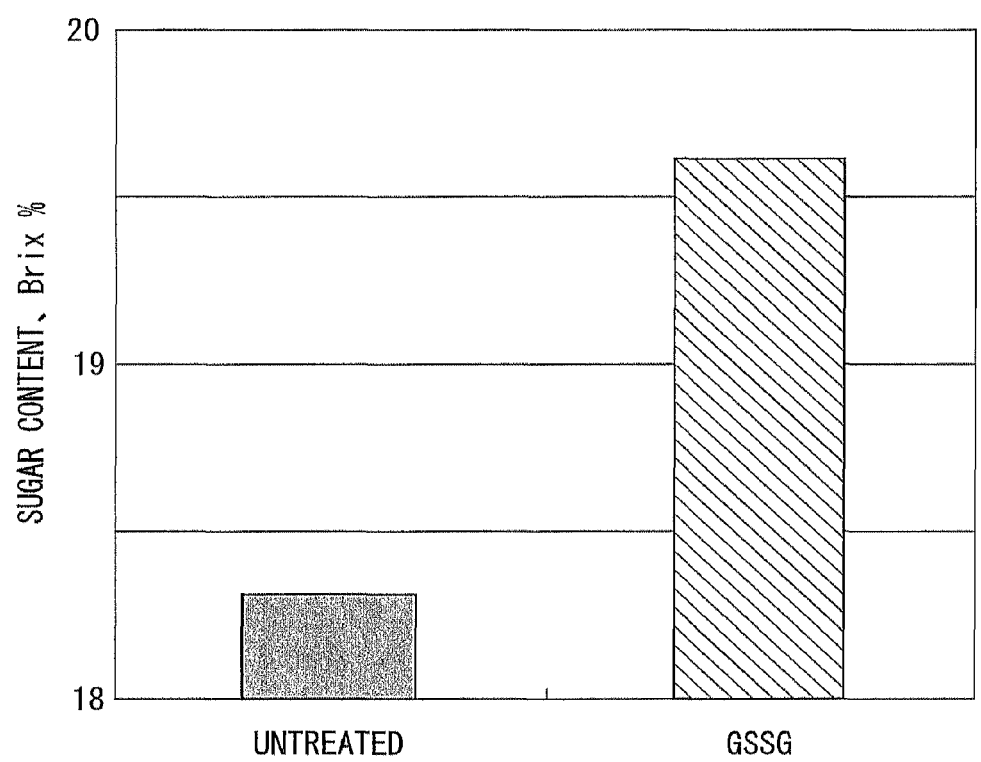
FIG. 8 illustrates a determination result of sugar content of *Zea mays* L. var. saccharata Sturt fruit obtained in Example 11.

Fruit was harvested 86 days after the sowing and subjected to a sensory test of sugar content. As a result, it was determined that fruit of the plant applied with GSSG increased in sugar content compared to that of the plant applied with no GSSG. Further, the fruit obtained was subjected to sugar content determination using "Pocket" Refractometer APAL-1 (ATAGO CO., LTD.). For comparison, the fruit of the plant applied with no GSSG was also subjected to the sugar content determination. FIG. 8 shows a result of determination of sugar content of *Zea mays* L. var. saccharata Sturt fruit obtained in the present example. In FIG. 8, the vertical scale indicates sugar content (Brix, unit: %). Further, an ANOVA analysis was carried out by using StatView5.0 (SAS Institute Inc.) with a significant difference level of 5%. As a result, a significant difference was shown.

It was also determined that the plant applied with GSSG increased in size and number of fruit. Further, it was determined that the fruit of the plant applied with GSSG was already able to be harvested 70 days after the sowing.

The results above indicated that *Zea mays* L. var. saccharata Sturt fruit having an increased sugar content could be produced by cultivation using a culture medium that includes GSSG.

The composition, in accordance with the present invention, for producing a plant body having an improved sugar content includes a substance for regulating an oxidation-reduction state of a cell. Therefore, with the composition in accordance with the present invention, it is possible to easily produce the plant body having an improved sugar content.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

The composition in accordance with the present invention, with which a plant having an improved sugar content can be easily produced, is industrially applicable in agriculture, food industry, and the like. Further, because ethanol can be produced with high efficiency from a plant having a high sugar content, the composition in accordance with the present invention is applicable to a wide range of industries such as energy industry.

The invention claimed is:

1. A method for producing a plant with a higher sugar content relative to a corresponding wild strain or untreated plant, the method comprising the steps of:
introducing an effective amount of polynucleotide encoding a γ-glutamylcysteine synthetase into a plant, so as to produce a transgenic plant;
cultivating the transgenic plant under conditions suitable for growth; and
comparing the sugar content of fruit of the plant to fruit of the wild strain to indicate that the sugar content of the transgenic plant is increased.

* * * * *

```
                        SEQUENCE LISTING

<160> NUMBER OF SEQ ID NOS: 56

<210> SEQ ID NO 1
<211> LENGTH: 522
<212> TYPE: PRT
<213> ORGANISM: Arabidopsis thaliana

<400> SEQUENCE: 1

Met Ala Leu Leu Ser Gln Ala Gly Gly Ser Tyr Thr Val Val Pro Ser
1               5                   10                  15

Gly Val Cys Ser Lys Ala Gly Thr Lys Ala Val Val Ser Gly Gly Val
            20                  25                  30

Arg Asn Leu Asp Val Leu Arg Met Lys Glu Ala Phe Gly Ser Ser Tyr
        35                  40                  45

Ser Arg Ser Leu Ser Thr Lys Ser Met Leu Leu His Ser Val Lys Arg
    50                  55                  60

Ser Lys Arg Gly His Gln Leu Ile Val Ala Ala Ser Pro Pro Thr Glu
65                  70                  75                  80

Glu Ala Val Val Ala Thr Glu Pro Leu Thr Arg Glu Asp Leu Ile Ala
                85                  90                  95

Tyr Leu Ala Ser Gly Cys Lys Thr Lys Asp Lys Tyr Arg Ile Gly Thr
            100                 105                 110
```

Glu His Glu Lys Phe Gly Phe Glu Val Asn Thr Leu Arg Pro Met Lys
            115                 120                 125

Tyr Asp Gln Ile Ala Glu Leu Leu Asn Gly Ile Ala Glu Arg Phe Glu
130                 135                 140

Trp Glu Lys Val Met Glu Gly Asp Lys Ile Ile Gly Leu Lys Gln Gly
145                 150                 155                 160

Lys Gln Ser Ile Ser Leu Glu Pro Gly Gly Gln Phe Glu Leu Ser Gly
            165                 170                 175

Ala Pro Leu Glu Thr Leu His Gln Thr Cys Ala Glu Val Asn Ser His
            180                 185                 190

Leu Tyr Gln Val Lys Ala Val Ala Glu Glu Met Gly Ile Gly Phe Leu
            195                 200                 205

Gly Ile Gly Phe Gln Pro Lys Trp Arg Arg Glu Asp Ile Pro Ile Met
210                 215                 220

Pro Lys Gly Arg Tyr Asp Ile Met Arg Asn Tyr Met Pro Lys Val Gly
225                 230                 235                 240

Thr Leu Gly Leu Asp Met Met Leu Arg Thr Cys Thr Val Gln Val Asn
                245                 250                 255

Leu Asp Phe Ser Ser Glu Ala Asp Met Ile Arg Lys Phe Arg Ala Gly
            260                 265                 270

Leu Ala Leu Gln Pro Ile Ala Thr Ala Leu Phe Ala Asn Ser Pro Phe
            275                 280                 285

Thr Glu Gly Lys Pro Asn Gly Phe Leu Ser Met Arg Ser His Ile Trp
            290                 295                 300

Thr Asp Thr Asp Lys Asp Arg Thr Gly Met Leu Pro Phe Val Phe Asp
305                 310                 315                 320

Asp Ser Phe Gly Phe Glu Gln Tyr Val Asp Tyr Ala Leu Asp Val Pro
                325                 330                 335

Met Tyr Phe Ala Tyr Arg Lys Asn Lys Tyr Ile Asp Cys Thr Gly Met
                340                 345                 350

Thr Phe Arg Gln Phe Leu Ala Gly Lys Leu Pro Cys Leu Pro Gly Glu
            355                 360                 365

Leu Pro Ser Tyr Asn Asp Trp Glu Asn His Leu Thr Thr Ile Phe Pro
            370                 375                 380

Glu Val Arg Leu Lys Arg Tyr Leu Glu Met Arg Gly Ala Asp Gly Gly
385                 390                 395                 400

Pro Trp Arg Arg Leu Cys Ala Leu Pro Ala Phe Trp Val Gly Leu Leu
                405                 410                 415

Tyr Asp Asp Asp Ser Leu Gln Ala Ile Leu Asp Leu Thr Ala Asp Trp
                420                 425                 430

Thr Pro Ala Glu Arg Glu Met Leu Arg Asn Lys Val Pro Val Thr Gly
            435                 440                 445

Leu Lys Thr Pro Phe Arg Asp Gly Leu Leu Lys His Val Ala Glu Asp
            450                 455                 460

Val Leu Lys Leu Ala Lys Asp Gly Leu Glu Arg Arg Gly Tyr Lys Glu
465                 470                 475                 480

Ala Gly Phe Leu Asn Ala Val Asp Glu Val Val Arg Thr Gly Val Thr
                485                 490                 495

Pro Ala Glu Lys Leu Leu Glu Met Tyr Asn Gly Glu Trp Gly Gln Ser
            500                 505                 510

Val Asp Pro Val Phe Glu Glu Leu Leu Tyr
            515                 520

<210> SEQ ID NO 2

<211> LENGTH: 1569
<212> TYPE: DNA
<213> ORGANISM: Arabidopsis thaliana

<400> SEQUENCE: 2

```
atggcgctct tgtctcaagc aggaggatca tacactgttg ttccttctgg agtttgttca    60
aaggctggaa ctaaagctgt tgtttcgggt ggcgtgagga atttggatgt tttgaggatg   120
aaagaagctt ttggtagctc ctactctagg agtctatcta ccaaatcaat gcttctccat   180
tctgttaaga ggagtaagag agggcatcaa ttgattgttg cggcaagtcc tccaacggaa   240
gaggctgtag ttgcaactga gccgttgacg agagaggatc tcattgccta tcttgcctct   300
ggatgcaaaa caaaggacaa atatagaata ggtacagaac atgagaaatt tggttttgag   360
gtcaatactt tgcgccctat gaagtatgat caaatagccg agcttcttaa tggtatcgct   420
gaaagatttg aatgggaaaa agtaatggaa ggtgacaaga tcattggtct gaagcaggga   480
aagcaaagca tttcacttga acctgggggt cagttcgagc ttagtggtgc acctcttgag   540
actttgcatc aaacttgtgc tgaagtcaat tcacatcttt atcaggtaaa agcagttgct   600
gaggaaatgg gaattggttt cttaggaatt ggcttccagc ccaaatggcg tcgggaggat   660
atacccatca tgccaaaggg gagatacgac attatgagaa actacatgcc gaaagttggt   720
acccttggtc ttgatatgat gctccgaacg tgtactgttc aggttaatct ggattttagc   780
tcagaagctg atatgatcag gaagtttcgt gctggtcttg ctttacaacc tatagcaacg   840
gctctatttg cgaattcccc ttttacagaa ggaaagccaa acggatttct cagcatgaga   900
agccacatat ggacagacac tgacaaggac cgcacaggaa tgctaccatt tgttttcgat   960
gactcttttg ggtttgagca gtatgttgac tacgcactcg atgtccctat gtactttgcc  1020
tacagaaaga acaaatacat cgactgtact ggaatgacat tcggcaatt cttggctgga  1080
aaacttccct gtctccctgg tgaactgcct tcatataatg attgggaaaa ccatctgaca  1140
acaatattcc cagaggttcg gttgaagaga tacttggaga tgagaggtgc tgatggaggt  1200
ccctggagga ggctgtgtgc cctgccagct ttctgggtgg gtttattata tgatgatgat  1260
agtctccaag ctatcctgga tctgacagct gactggactc cagcagagag agagatgcta  1320
aggaacaaag tcccagttac tggcttaaag actccttttta gggatggttt gttaaagcat  1380
gtcgctgaag atgtcctgaa actcgcaaag gatgtttag agcgcagagg ctacaaggaa  1440
gccggttttct tgaacgcagt cgatgaagtg gtcagaacag gagttacgcc tgcggagaag  1500
ctcttggaga tgtacaatgg agaatgggga caaagcgtag atcccgtgtt cgaagagctg  1560
ctgtactaa                                                          1569
```

<210> SEQ ID NO 3
<211> LENGTH: 449
<212> TYPE: PRT
<213> ORGANISM: Arabidopsis thaliana

<400> SEQUENCE: 3

```
Met Ala Ser Pro Pro Thr Glu Glu Ala Val Val Ala Thr Glu Pro Leu
1               5                   10                  15

Thr Arg Glu Asp Leu Ile Ala Tyr Leu Ala Ser Gly Cys Lys Thr Lys
            20                  25                  30

Asp Lys Tyr Arg Ile Gly Thr Glu His Glu Lys Phe Gly Phe Glu Val
        35                  40                  45

Asn Thr Leu Arg Pro Met Lys Tyr Asp Gln Ile Ala Glu Leu Leu Asn
    50                  55                  60
```

```
Gly Ile Ala Glu Arg Phe Glu Trp Glu Lys Val Met Glu Gly Asp Lys
 65                  70                  75                  80

Ile Ile Gly Leu Lys Gln Gly Lys Gln Ser Ile Ser Leu Glu Pro Gly
                 85                  90                  95

Gly Gln Phe Glu Leu Ser Gly Ala Pro Leu Glu Thr Leu His Gln Thr
            100                 105                 110

Cys Ala Glu Val Asn Ser His Leu Tyr Gln Val Lys Ala Val Ala Glu
        115                 120                 125

Glu Met Gly Ile Gly Phe Leu Gly Ile Gly Phe Gln Pro Lys Trp Arg
    130                 135                 140

Arg Glu Asp Ile Pro Ile Met Pro Lys Gly Arg Tyr Asp Ile Met Arg
145                 150                 155                 160

Asn Tyr Met Pro Lys Val Gly Thr Leu Gly Leu Asp Met Met Leu Arg
                165                 170                 175

Thr Cys Thr Val Gln Val Asn Leu Asp Phe Ser Ser Glu Ala Asp Met
            180                 185                 190

Ile Arg Lys Phe Arg Ala Gly Leu Ala Leu Gln Pro Ile Ala Thr Ala
        195                 200                 205

Leu Phe Ala Asn Ser Pro Phe Thr Glu Gly Lys Pro Asn Gly Phe Leu
    210                 215                 220

Ser Met Arg Ser His Ile Trp Thr Asp Thr Asp Lys Asp Arg Thr Gly
225                 230                 235                 240

Met Leu Pro Phe Val Phe Asp Asp Ser Phe Gly Phe Glu Gln Tyr Val
                245                 250                 255

Asp Tyr Ala Leu Asp Val Pro Met Tyr Phe Ala Tyr Arg Lys Asn Lys
            260                 265                 270

Tyr Ile Asp Cys Thr Gly Met Thr Phe Arg Gln Phe Leu Ala Gly Lys
        275                 280                 285

Leu Pro Cys Leu Pro Gly Glu Leu Pro Ser Tyr Asn Asp Trp Glu Asn
    290                 295                 300

His Leu Thr Thr Ile Phe Pro Glu Val Arg Leu Lys Arg Tyr Leu Glu
305                 310                 315                 320

Met Arg Gly Ala Asp Gly Gly Pro Trp Arg Arg Leu Cys Ala Leu Pro
                325                 330                 335

Ala Phe Trp Val Gly Leu Leu Tyr Asp Asp Asp Ser Leu Gln Ala Ile
            340                 345                 350

Leu Asp Leu Thr Ala Asp Trp Thr Pro Ala Glu Arg Glu Met Leu Arg
        355                 360                 365

Asn Lys Val Pro Val Thr Gly Leu Lys Thr Pro Phe Arg Asp Gly Leu
    370                 375                 380

Leu Lys His Val Ala Glu Asp Val Leu Lys Leu Ala Lys Asp Gly Leu
385                 390                 395                 400

Glu Arg Arg Gly Tyr Lys Glu Ala Gly Phe Leu Asn Ala Val Asp Glu
                405                 410                 415

Val Val Arg Thr Gly Val Thr Pro Ala Glu Lys Leu Leu Glu Met Tyr
            420                 425                 430

Asn Gly Glu Trp Gly Gln Ser Val Asp Pro Val Phe Glu Glu Leu Leu
        435                 440                 445

Tyr

<210> SEQ ID NO 4
<211> LENGTH: 1350
<212> TYPE: DNA
<213> ORGANISM: Arabidopsis thaliana
```

<400> SEQUENCE: 4

```
atggcaagtc ctccaacgga agaggctgta gttgcaactg agccgttgac gagagaggat     60
ctcattgcct atcttgcctc tggatgcaaa acaaaggaca atatagaat aggtacagaa     120
catgagaaat ttggttttga ggtcaatact ttgcgcccta tgaagtatga tcaaatagcc    180
gagcttctta atggtatcgc tgaaagattt gaatgggaaa agtaatgga aggtgacaag    240
atcattggtc tgaagcaggg aaagcaaagc atttcacttg aacctggggg tcagttcgag    300
cttagtggtg cacctcttga ctttgcat caaacttgtg ctgaagtcaa ttcacatctt    360
tatcaggtaa aagcagttgc tgaggaaatg ggaattggtt tcttaggaat ggcttccag    420
cccaaatggc gtcgggagga tatacccatc atgccaaagg ggagatacga cattatgaga    480
aactacatgc cgaaagttgg tacccttggt cttgatatga tgctccgaac gtgtactgtt    540
caggttaatc tggattttag ctcagaagct gatatgatca ggaagtttcg tgctggtctt    600
gctttacaac ctatagcaac ggctctattt gcgaattccc cttttacaga aggaaagcca    660
aacggatttc tcagcatgag aagccacata tggacagaca ctgacaagga ccgcacagga    720
atgctaccat ttgttttcga tgactctttt gggtttgagc agtatgttga ctacgcactc    780
gatgtcccta tgtactttgc ctacagaaag aacaaataca tcgactgtac tggaatgaca    840
tttcggcaat tcttggctgg aaaacttccc tgtctccctg gtgaactgcc ttcatataat    900
gattgggaaa accatctgac aacaatattc ccagaggttc ggttgaagag atacttggag    960
atgagaggtc tgatggagg tccctggagg aggctgtgtg ccctgccagc tttctgggtg   1020
ggtttattat atgatgatga tagtctccaa gctatcctgg atctgacagc tgactggact   1080
ccagcagaga gagagatgct aaggaacaaa gtcccagtta ctggcttaaa gactccttt    1140
agggatggtt tgttaaagca tgtcgctgaa gatgtcctga aactcgcaaa ggatggttta   1200
gagcgcagag gctacaagga agccggtttc ttgaacgcag tcgatgaagt ggtcagaaca   1260
ggagttacgc ctgcggagaa gctcttggag atgtacaatg agaatggggg acaaagcgta   1320
gatcccgtgt tcgaagagct gctgtactaa                                    1350
```

<210> SEQ ID NO 5
<211> LENGTH: 391
<212> TYPE: PRT
<213> ORGANISM: Arabidopsis thaliana

<400> SEQUENCE: 5

```
Met Ala Ser Ala Ser Phe Val Lys Pro Asn Thr Leu Ser Ser Pro Trp
1               5                   10                  15

Ile Gly Gln Arg Ser Phe Ala His Thr Ser Ala Ser Ser Ser Pro Pro
            20                  25                  30

Pro Arg Val Ser Phe Ala Ile Arg Ala Gly Ala Tyr Ser Asp Glu Leu
        35                  40                  45

Val Lys Thr Ala Lys Ser Ile Ala Ser Pro Gly Arg Gly Ile Leu Ala
    50                  55                  60

Ile Asp Glu Ser Asn Ala Thr Cys Gly Lys Arg Leu Ala Ser Ile Gly
65                  70                  75                  80

Leu Asp Asn Thr Glu Asp Asn Arg Gln Ala Tyr Arg Gln Leu Leu Leu
                85                  90                  95

Thr Thr Pro Gly Leu Gly Asp Tyr Ile Ser Gly Ser Ile Leu Phe Glu
            100                 105                 110

Glu Thr Leu Tyr Gln Ser Thr Lys Asp Gly Lys Thr Phe Val Asp Cys
        115                 120                 125
```

```
Leu Arg Asp Ala Asn Ile Val Pro Gly Ile Lys Val Asp Lys Gly Leu
    130                 135                 140

Ser Pro Leu Ala Gly Ser Asn Glu Glu Ser Trp Cys Gln Gly Leu Asp
145                 150                 155                 160

Gly Leu Ala Ser Arg Ser Ala Glu Tyr Tyr Lys Gln Gly Ala Arg Phe
                165                 170                 175

Ala Lys Trp Arg Thr Val Val Ser Val Pro Cys Gly Pro Ser Ala Leu
            180                 185                 190

Ala Val Lys Glu Ala Ala Trp Gly Leu Ala Arg Tyr Ala Ala Ile Ser
                195                 200                 205

Gln Asp Asn Gly Leu Val Pro Ile Val Glu Pro Glu Ile Leu Leu Asp
    210                 215                 220

Gly Asp His Pro Ile Glu Arg Thr Leu Glu Val Ala Glu Lys Val Trp
225                 230                 235                 240

Ser Glu Val Phe Phe Tyr Leu Ala Gln Asn Asn Val Met Phe Glu Gly
                245                 250                 255

Ile Leu Leu Lys Pro Ser Met Val Thr Pro Gly Ala Glu His Lys Asn
                260                 265                 270

Lys Ala Ser Pro Glu Thr Val Ala Asp Phe Thr Leu Thr Met Leu Lys
                275                 280                 285

Arg Arg Val Pro Pro Ala Val Pro Gly Ile Met Phe Leu Ser Gly Gly
    290                 295                 300

Gln Ser Glu Ala Glu Ala Thr Leu Asn Leu Asn Ala Met Asn Gln Ser
305                 310                 315                 320

Pro Asn Pro Trp His Val Ser Phe Ser Tyr Ala Arg Ala Leu Gln Asn
                325                 330                 335

Ser Val Leu Arg Thr Trp Gln Gly Lys Pro Glu Lys Ile Glu Ala Ser
                340                 345                 350

Gln Lys Ala Leu Leu Val Arg Ala Lys Ala Asn Ser Leu Ala Gln Leu
            355                 360                 365

Gly Lys Tyr Ser Ala Glu Gly Glu Asn Glu Asp Ala Lys Lys Gly Met
            370                 375                 380

Phe Val Lys Gly Tyr Thr Tyr
385                 390

<210> SEQ ID NO 6
<211> LENGTH: 398
<212> TYPE: PRT
<213> ORGANISM: Arabidopsis thaliana

<400> SEQUENCE: 6

Met Ala Ser Thr Ser Leu Leu Lys Ala Ser Pro Val Leu Asp Lys Ser
1               5                   10                  15

Glu Trp Val Lys Gly Gln Ser Val Leu Phe Arg Gln Pro Ser Ser Ala
                20                  25                  30

Ser Val Val Leu Arg Asn Arg Ala Thr Ser Leu Thr Val Arg Ala Ala
            35                  40                  45

Ser Ser Tyr Ala Asp Glu Leu Val Lys Thr Ala Lys Thr Ile Ala Ser
        50                  55                  60

Pro Gly Arg Gly Ile Leu Ala Met Asp Glu Ser Asn Ala Thr Cys Gly
65                  70                  75                  80

Lys Arg Leu Asp Ser Ile Gly Leu Glu Asn Thr Glu Ala Asn Arg Gln
                85                  90                  95

Ala Phe Arg Thr Leu Leu Val Ser Ala Pro Gly Leu Gly Gln Tyr Val
            100                 105                 110
```

```
Ser Gly Ala Ile Leu Phe Glu Glu Thr Leu Tyr Gln Ser Thr Thr Glu
        115                 120                 125
Gly Lys Lys Met Val Asp Val Leu Val Glu Gln Asn Ile Val Pro Gly
        130                 135                 140
Ile Lys Val Asp Lys Gly Leu Val Pro Leu Val Gly Ser Asn Asn Glu
145                 150                 155                 160
Ser Trp Cys Gln Gly Leu Asp Gly Leu Ser Ser Arg Thr Ala Ala Tyr
                165                 170                 175
Tyr Gln Gln Gly Ala Arg Phe Ala Lys Trp Arg Thr Val Val Ser Ile
            180                 185                 190
Pro Asn Gly Pro Ser Ala Leu Ala Val Lys Glu Ala Ala Trp Gly Leu
        195                 200                 205
Ala Arg Tyr Ala Ala Ile Ser Gln Asp Ser Gly Leu Val Pro Ile Val
        210                 215                 220
Glu Pro Glu Ile Leu Leu Asp Gly Glu His Asp Ile Asp Arg Thr Tyr
225                 230                 235                 240
Asp Val Ala Glu Lys Val Trp Ala Glu Val Phe Phe Tyr Leu Ala Gln
                245                 250                 255
Asn Asn Val Met Phe Glu Gly Ile Leu Leu Lys Pro Ser Met Val Thr
            260                 265                 270
Pro Gly Ala Glu Ser Lys Asp Arg Ala Thr Pro Glu Gln Val Ala Ala
        275                 280                 285
Tyr Thr Leu Lys Leu Leu Arg Asn Arg Val Pro Pro Ala Val Pro Gly
        290                 295                 300
Ile Met Phe Leu Ser Gly Gly Gln Ser Glu Val Glu Ala Thr Leu Asn
305                 310                 315                 320
Leu Asn Ala Met Asn Gln Ala Pro Asn Pro Trp His Val Ser Phe Ser
                325                 330                 335
Tyr Ala Arg Ala Leu Gln Asn Thr Cys Leu Lys Thr Trp Gly Gly Arg
            340                 345                 350
Pro Glu Asn Val Asn Ala Ala Gln Thr Thr Leu Leu Ala Arg Ala Lys
        355                 360                 365
Ala Asn Ser Leu Ala Gln Leu Gly Lys Tyr Thr Gly Glu Gly Glu Ser
        370                 375                 380
Glu Glu Ala Lys Glu Gly Met Phe Val Lys Gly Tyr Thr Tyr
385                 390                 395

<210> SEQ ID NO 7
<211> LENGTH: 1176
<212> TYPE: DNA
<213> ORGANISM: Arabidopsis thaliana

<400> SEQUENCE: 7
atggcgtctg ctagcttcgt taagcctaac accctctctt ctccatggat cggccaacgc      60
tcctttgctc acacctctgc ttcttcttct cctcctcctc gagtctccct cgcgatccgc     120
gccggtgctt actccgacga gcttgttaaa accgccaaaa gcattgcatc ccctgggaga     180
ggtatcttgg cgatcgatga gtccaatgca acctgtggga gaggcttgc ttctatcggc      240
ttggataaca ccgaggacaa ccgtcaggcc tacaggcaac ttctgcttac cactcctggc     300
ctcggcgatt acatctctgg ttccattctc ttcgaggaga ctctttacca gtccaccaag     360
gacggtaaga cctttgtcga ttgcttgcgc gatgccaaca tcgtccctgg catcaaagtt     420
gacaagggct tgtctcccct agccggttcc aacgaagagt cttggtgcca aggcttggat     480
ggattggcct cacgctctgc tgagtactac aagcaaggcg ctcgttttgc caagtggagg     540
```

| | |
|---|---|
| acagtggtga gtgttccctg cggtccttca gcactggctg tgaaggaagc tgcgtggggg | 600 |
| ctggctcgct atgcagccat ctctcaggat aatggtcttg tccccattgt ggagccagag | 660 |
| atccttctgg acggggacca cccaatagag aggactctgg aggtggcaga gaaagtgtgg | 720 |
| tcagaggtgt tcttctactt ggcacagaac aacgtcatgt ttgagggcat tctgttgaag | 780 |
| ccgagcatgg tcaccccagg cgctgagcac aagaacaagg cctctcccga gaccgttgca | 840 |
| gatttcacgc tcaccatgct gaaaaggagg gttcctccgg ctgtcccagg gatcatgttt | 900 |
| ctgtcaggag gacaatcaga ggcagaggcc acactgaacc tgaacgccat gaaccagagc | 960 |
| ccaaacccat ggcatgtgtc cttctcatac gcacgtgccc tgcagaactc cgtgctcaga | 1020 |
| acatggcaag gcaagccgga gaagattgag gcctcgcaga aggcactgtt ggtgagggca | 1080 |
| aaggccaact cactggccca gctcggcaaa tactcagccg agggagagaa cgaggatgcc | 1140 |
| aagaaaggaa tgtttgtcaa gggttacacc tactga | 1176 |

<210> SEQ ID NO 8
<211> LENGTH: 1515
<212> TYPE: DNA
<213> ORGANISM: Artificial Sequence
<220> FEATURE:
<223> OTHER INFORMATION: Description of Artificial Sequence:Artificially Synthesized Primer Sequence

<400> SEQUENCE: 8

| | |
|---|---|
| ccaaagtaga cgactactaa tagtagtaaa caaaaccttt ggctttaaca ctctcctcca | 60 |
| aatcccagat ctctctctgt ctctgtcccg cggagtcccc gagagattga tcaccatcac | 120 |
| ttttgtacct tccttgtact acctatggcg tctgctagct tcgttaagcc taacaccctc | 180 |
| tcttctccat ggatcggcca acgctccttt gctcacacct ctgcttcttc ttctcctcct | 240 |
| cctcgagtct ccttcgcgat ccgcgccggt gcttactccg acgagcttgt taaaaccgcc | 300 |
| aaaagcattg catccctgg gagaggtatc ttggcgatcg atgagtccaa tgcaacctgt | 360 |
| gggaagaggc ttgcttctat cggcttggat aacaccgagg acaaccgtca ggcctacagg | 420 |
| caacttctgc ttaccactcc tggcctcggc gattacatct ctggttccat tctcttcgag | 480 |
| gagactcttt accagtccac caaggacggt aagaccttg tcgattgctt gcgcgatgcc | 540 |
| aacatcgtcc ctggcatcaa agttgacaag ggcttgtctc ccctagccgg ttccaacgaa | 600 |
| gagtcttggt gccaaggctt ggatggattg gcctcacgct ctgctgagta ctacaagcaa | 660 |
| ggcgctcgtt ttgccaagtg gaggacagtg gtgagtgttc cctgcggtcc ttcagcactg | 720 |
| gctgtgaagg aagctgcgtg ggggctggct cgctatgcag ccatctctca ggataatggt | 780 |
| cttgtcccca ttgtggagcc agagatcctt ctggacgggg accacccaat agagaggact | 840 |
| ctggaggtgg cagagaaagt gtggtcagag gtgttcttct acttggcaca gaacaacgtc | 900 |
| atgtttgagg cattctgtt gaagccgagc atggtcaccc caggcgctga gcacaagaac | 960 |
| aaggcctctc ccgagaccgt tgcagatttc acgctcacca tgctgaaaag gagggttcct | 1020 |
| ccggctgtcc cagggatcat gtttctgtca ggaggacaat cagaggcaga ggccacactg | 1080 |
| aacctgaacg ccatgaacca gagcccaaac ccatggcatg tgtccttctc atacgcacgt | 1140 |
| gccctgcaga actccgtgct cagaacatgg caaggcaagc cggagaagat tgaggcctcg | 1200 |
| cagaaggcac tgttggtgag gcaaaggcc aactcactgg cccagctcgg caaatactca | 1260 |
| gccgagggag agaacgagga tgccaagaaa ggaatgtttg tcaagggtta cacctactga | 1320 |
| tttgttaatt tcagagatcg taataaggat taaggaccat tgttgtcttt tgttttttt | 1380 |
| tcccttttt gttttgtctc tgagaaagaa agacagtcac gagtcacgat catatcatat | 1440 |

```
atgtatgtga gcaacgtgaa acatcctct taaatctata tttcctctca gaaagactga    1500
ttactgtttg actgc                                                   1515

<210> SEQ ID NO 9
<211> LENGTH: 1518
<212> TYPE: DNA
<213> ORGANISM: Arabidopsis thaliana

<400> SEQUENCE: 9
aaaagaggga ggagtgagag ataagggtgg tgtcataagc gtttactgtg agtctctcaa     60
agaaaccaaa ggcagagaaa agagataaca cacacaaaaa aaaatggcat caacctcact    120
cctcaaggct tctccggtgt tggacaaatc cgaatgggtc aagggacaaa gcgttctctt    180
ccgtcagcct tcttccgctt ctgtcgtcct ccgcaaccgt gccacctccc tcaccgtccg    240
tgccgcttcc tcctacgccg atgagcttgt taagacagcg aaaactattg cgtctcccgg    300
acgtggaatc ttggcgatgg acgagtcaaa cgcgacttgc gggaaacgtt tggattcgat    360
agggctagag aacactgagg caaatcgtca agctttccgg actttgctgg tctctgcacc    420
gggactcgga cagtacgtct ccggcgcaat tctatttgag gagactctgt accagtctac    480
caccgaaggc aagaaaatgg tcgacgtcct cgtcgagcag aacattgtcc ctggtatcaa    540
agtcgacaag ggtttggtgc cacttgttgg atccaacaat gagtcatggt gccaaggact    600
agatggtcta tcatctcgaa ctgctgctta ctatcaacag ggtgcgcgtt cgccaaatg     660 gcgtactgtc gtgagcattc ctaacggtcc gtctgccctc gccgtcaaag aagctgcttg    720
gggtcttgct cgatacgctg ccatttcaca ggacagcggt ttggttccga ttgttgagcc    780
agagatcttg ttggatggag aacacgacat tgacagaaca tacgacgtag cagagaaggt    840
ttgggctgag gttttctttt accttgctca gaacaatgtc atgtttgaag gtatcctcct    900
aaaaccgagc atggtgactc ccggagctga gtctaaagac agagctactc ctgaacaagt    960
tgccgcctac accctcaagc tcctccgcaa cagagtccct cccgcagtcc ccggaatcat   1020 gttttttgtcc ggaggacagt cggaggtgga ggcaacactc aacttgaacg caatgaacca   1080
ggcaccaaac ccatggcacg tgtccttctc ctacgcacgt gcgttgcaga acacttgtct   1140
gaaaacatgg ggcggcagac ccgagaacgt gaacgcagct cagaccactc tcttggcccg   1200
tgccaaggcc aattcgttgg ctcagctcgg aaaatacacc ggtgagggtg agtccgaaga   1260
ggctaaggag ggcatgttcg tcaaagggta cacctattga agagatgatg ctgtgaaaaa   1320
agagatgaag cagatgtttt aatcacattt gtttttgagt ttgcttgtta ttaatcatgt   1380
caaatcatta ttttctctgc ttactttgcg ttagctactc cttttaataa gttctattat   1440
attgaagtta tctatctctc ttgatctatt taaacttgaa actacaacta ttccataatc   1500
aaccaatttt aaattttg                                                 1518

<210> SEQ ID NO 10
<211> LENGTH: 22
<212> TYPE: DNA
<213> ORGANISM: Artificial
<220> FEATURE:
<223> OTHER INFORMATION: Primer

<400> SEQUENCE: 10
gctttcttct agatttcgac gg                                              22

<210> SEQ ID NO 11
<211> LENGTH: 23
```

```
<212> TYPE: DNA
<213> ORGANISM: Artificial
<220> FEATURE:
<223> OTHER INFORMATION: Primer

<400> SEQUENCE: 11
cctgatcata tcagcttctg agc                                                 23

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
atgccaaagg ggagatacga                                                     20

<210> SEQ ID NO 13
<211> LENGTH: 23
<212> TYPE: DNA
<213> ORGANISM: Artificial
<220> FEATURE:
<223> OTHER INFORMATION: Primer

<400> SEQUENCE: 13
ggagactcga gctcttcaga tag                                                 23

<210> SEQ ID NO 14
<211> LENGTH: 27
<212> TYPE: DNA
<213> ORGANISM: Artificial
<220> FEATURE:
<223> OTHER INFORMATION: Primer

<400> SEQUENCE: 14
agggcatcta gagaccatgg caagtcc                                             27

<210> SEQ ID NO 15
<211> LENGTH: 351
<212> TYPE: PRT
<213> ORGANISM: Arabidopsis thaliana

<400> SEQUENCE: 15

Ala Gly Ala Tyr Ser Asp Glu Leu Val Lys Thr Ala Lys Ser Ile Ala
1               5                   10                  15

Ser Pro Gly Arg Gly Ile Leu Ala Ile Asp Glu Ser Asn Ala Thr Cys
            20                  25                  30

Gly Lys Arg Leu Ala Ser Ile Gly Leu Asp Asn Thr Glu Asp Asn Arg
        35                  40                  45

Gln Ala Tyr Arg Gln Leu Leu Leu Thr Thr Pro Gly Leu Gly Asp Tyr
    50                  55                  60

Ile Ser Gly Ser Ile Leu Phe Glu Glu Thr Leu Tyr Gln Ser Thr Lys
65                  70                  75                  80

Asp Gly Lys Thr Phe Val Asp Cys Leu Arg Asp Ala Asn Ile Val Pro
                85                  90                  95

Gly Ile Lys Val Asp Lys Gly Leu Ser Pro Leu Ala Gly Ser Asn Glu
            100                 105                 110

Glu Ser Trp Cys Gln Gly Leu Asp Gly Leu Ala Ser Arg Ser Ala Glu
        115                 120                 125

Tyr Tyr Lys Gln Gly Ala Arg Phe Ala Lys Trp Arg Thr Val Val Ser
    130                 135                 140
```

-continued

```
Val Pro Cys Gly Pro Ser Ala Leu Ala Val Lys Glu Ala Ala Trp Gly
145                 150                 155                 160

Leu Ala Arg Tyr Ala Ala Ile Ser Gln Asp Asn Gly Leu Val Pro Ile
                165                 170                 175

Val Glu Pro Glu Ile Leu Leu Asp Gly Asp His Pro Ile Glu Arg Thr
            180                 185                 190

Leu Glu Val Ala Glu Lys Val Trp Ser Glu Val Phe Phe Tyr Leu Ala
        195                 200                 205

Gln Asn Asn Val Met Phe Glu Gly Ile Leu Leu Lys Pro Ser Met Val
    210                 215                 220

Thr Pro Gly Ala Glu His Lys Asn Lys Ala Ser Pro Glu Thr Val Ala
225                 230                 235                 240

Asp Phe Thr Leu Thr Met Leu Lys Arg Arg Val Pro Pro Ala Val Pro
                245                 250                 255

Gly Ile Met Phe Leu Ser Gly Gly Gln Ser Glu Ala Glu Ala Thr Leu
            260                 265                 270

Asn Leu Asn Ala Met Asn Gln Ser Pro Asn Pro Trp His Val Ser Phe
        275                 280                 285

Ser Tyr Ala Arg Ala Leu Gln Asn Ser Val Leu Arg Thr Trp Gln Gly
    290                 295                 300

Lys Pro Glu Lys Ile Glu Ala Ser Gln Lys Ala Leu Leu Val Arg Ala
305                 310                 315                 320

Lys Ala Asn Ser Leu Ala Gln Leu Gly Lys Tyr Ser Ala Glu Gly Glu
                325                 330                 335

Asn Glu Asp Ala Lys Lys Gly Met Phe Val Lys Gly Tyr Thr Tyr
            340                 345                 350
```

<210> SEQ ID NO 16
<211> LENGTH: 352
<212> TYPE: PRT
<213> ORGANISM: Arabidopsis thaliana

<400> SEQUENCE: 16

```
Ala Ala Ser Ala Tyr Ala Asp Glu Leu Val Lys Thr Ala Lys Thr Ile
1               5                   10                  15

Ala Ser Pro Gly His Gly Ile Met Ala Met Asp Glu Ser Asn Ala Thr
            20                  25                  30

Cys Gly Lys Arg Leu Ala Ser Ile Gly Leu Glu Asn Thr Glu Ala Asn
        35                  40                  45

Arg Gln Ala Tyr Arg Thr Leu Leu Val Ser Ala Pro Gly Leu Gly Gln
    50                  55                  60

Tyr Ile Ser Gly Ala Ile Leu Phe Glu Glu Thr Leu Tyr Gln Ser Thr
65                  70                  75                  80

Thr Asp Gly Lys Lys Met Val Asp Val Leu Val Glu Gln Asn Ile Val
                85                  90                  95

Pro Gly Ile Lys Val Asp Lys Gly Leu Val Pro Leu Val Gly Ser Tyr
            100                 105                 110

Asp Glu Ser Trp Cys Gln Gly Leu Asp Gly Leu Ala Ser Arg Thr Ala
        115                 120                 125

Ala Tyr Tyr Gln Gln Gly Ala Arg Phe Ala Lys Trp Arg Thr Val Val
    130                 135                 140

Ser Ile Pro Asn Gly Pro Ser Ala Leu Ala Val Lys Glu Ala Ala Trp
145                 150                 155                 160

Gly Leu Ala Arg Tyr Ala Ala Ile Ser Gln Asp Ser Gly Leu Val Pro
                165                 170                 175
```

```
Ile Val Glu Pro Glu Ile Met Leu Asp Gly Glu His Gly Ile Asp Arg
            180                 185                 190
Thr Tyr Asp Val Ala Glu Lys Val Trp Ala Glu Val Phe Phe Tyr Leu
        195                 200                 205
Ala Gln Asn Asn Val Met Phe Glu Gly Ile Leu Leu Lys Pro Ser Met
    210                 215                 220
Val Thr Pro Gly Ala Glu Ala Thr Asp Arg Ala Thr Pro Glu Gln Val
225                 230                 235                 240
Ala Ser Tyr Thr Leu Lys Leu Leu Arg Asn Arg Ile Pro Pro Ala Val
                245                 250                 255
Pro Gly Ile Met Phe Leu Ser Gly Gly Gln Ser Glu Leu Glu Ala Thr
            260                 265                 270
Leu Asn Leu Asn Ala Met Asn Gln Ala Pro Asn Pro Trp His Val Ser
        275                 280                 285
Phe Ser Tyr Ala Arg Ala Leu Gln Asn Thr Cys Leu Lys Thr Trp Gly
    290                 295                 300
Gly Lys Glu Glu Asn Val Lys Ala Ala Gln Asp Ile Leu Leu Ala Arg
305                 310                 315                 320
Ala Lys Ala Asn Ser Leu Ala Gln Leu Gly Lys Tyr Thr Gly Glu Gly
                325                 330                 335
Glu Ser Glu Glu Ala Lys Glu Gly Met Phe Val Lys Gly Tyr Thr Tyr
            340                 345                 350

<210> SEQ ID NO 17
<211> LENGTH: 352
<212> TYPE: PRT
<213> ORGANISM: Arabidopsis thaliana

<400> SEQUENCE: 17

Ala Ala Ser Ser Tyr Ala Asp Glu Leu Val Lys Thr Ala Lys Thr Ile
1               5                   10                  15
Ala Ser Pro Gly Arg Gly Ile Leu Ala Met Asp Glu Ser Asn Ala Thr
            20                  25                  30
Cys Gly Lys Arg Leu Asp Ser Ile Gly Leu Glu Asn Thr Glu Ala Asn
        35                  40                  45
Arg Gln Ala Phe Arg Thr Leu Leu Val Ser Ala Pro Gly Leu Gly Gln
    50                  55                  60
Tyr Val Ser Gly Ala Ile Leu Phe Glu Glu Thr Leu Tyr Gln Ser Thr
65                  70                  75                  80
Thr Glu Gly Lys Lys Met Val Asp Val Leu Val Glu Gln Asn Ile Val
                85                  90                  95
Pro Gly Ile Lys Val Asp Lys Gly Leu Val Pro Leu Val Gly Ser Asn
            100                 105                 110
Asn Glu Ser Trp Cys Gln Gly Leu Asp Gly Leu Ser Ser Arg Thr Ala
        115                 120                 125
Ala Tyr Tyr Gln Gln Gly Ala Arg Phe Ala Lys Trp Arg Thr Val Val
    130                 135                 140
Ser Ile Pro Asn Gly Pro Ser Ala Leu Ala Val Lys Glu Ala Ala Trp
145                 150                 155                 160
Gly Leu Ala Arg Tyr Ala Ala Ile Ser Gln Asp Ser Gly Leu Val Pro
                165                 170                 175
Ile Val Glu Pro Glu Ile Leu Leu Asp Gly Glu His Asp Ile Asp Arg
            180                 185                 190
Thr Tyr Asp Val Ala Glu Lys Val Trp Ala Glu Val Phe Phe Tyr Leu
        195                 200                 205
```

```
Ala Gln Asn Asn Val Met Phe Glu Gly Ile Leu Leu Lys Pro Ser Met
    210                 215                 220

Val Thr Pro Gly Ala Glu Ser Lys Asp Arg Ala Thr Pro Glu Gln Val
225                 230                 235                 240

Ala Ala Tyr Thr Leu Lys Leu Leu Arg Asn Arg Val Pro Pro Ala Val
                245                 250                 255

Pro Gly Ile Met Phe Leu Ser Gly Gln Ser Glu Val Glu Ala Thr
            260                 265                 270

Leu Asn Leu Asn Ala Met Asn Gln Ala Pro Asn Pro Trp His Val Ser
        275                 280                 285

Phe Ser Tyr Ala Arg Ala Leu Gln Asn Thr Cys Leu Lys Thr Trp Gly
    290                 295                 300

Gly Arg Pro Glu Asn Val Asn Ala Ala Gln Thr Thr Leu Leu Ala Arg
305                 310                 315                 320

Ala Lys Ala Asn Ser Leu Ala Gln Leu Gly Lys Tyr Thr Gly Glu Gly
                325                 330                 335

Glu Ser Glu Glu Ala Lys Glu Gly Met Phe Val Lys Gly Tyr Thr Tyr
            340                 345                 350

<210> SEQ ID NO 18
<211> LENGTH: 353
<212> TYPE: PRT
<213> ORGANISM: Hordeum Vulgare

<400> SEQUENCE: 18

Ala Ser Gly Gly Ser Tyr Ala Asp Glu Leu Val Ser Thr Ala Lys Thr
1               5                   10                  15

Val Ala Ser Pro Gly Arg Gly Ile Leu Ala Ile Asp Glu Ser Ser Ala
                20                  25                  30

Thr Cys Gly Lys Arg Leu Ala Ser Ile Gly Leu Asp Asn Thr Glu Val
            35                  40                  45

Asn Arg Gln Ala Tyr Arg Gln Leu Leu Leu Thr Thr Ala Gly Leu Gly
        50                  55                  60

Glu Tyr Ile Ser Gly Ala Ile Leu Phe Glu Glu Thr Leu Tyr Gln Ser
65                  70                  75                  80

Thr Thr Asp Gly Lys Thr Phe Val Asp Val Leu Lys Asp Gln Asn Ile
                85                  90                  95

Met Pro Gly Ile Lys Val Asp Lys Gly Leu Val Pro Leu Pro Gly Ser
            100                 105                 110

Asn Asn Glu Ser Trp Cys Gln Gly Leu Asp Gly Leu Ala Ser Arg Cys
        115                 120                 125

Ala Glu Tyr Tyr Lys Gln Gly Ala Arg Phe Ala Lys Trp Arg Thr Val
    130                 135                 140

Val Ser Ile Pro Cys Gly Pro Thr Ala Leu Ala Val Lys Glu Ala Ala
145                 150                 155                 160

Trp Gly Leu Ala Arg Tyr Ala Ala Ile Ala Gln Asp Asn Gly Leu Val
                165                 170                 175

Pro Ile Val Glu Pro Glu Ile Leu Leu Asp Gly Asp His Gly Ile Glu
            180                 185                 190

Arg Thr Leu Glu Val Ala Glu Lys Val Trp Ser Glu Val Phe Phe Tyr
        195                 200                 205

Leu Ala Glu Asn Asn Val Leu Phe Glu Gly Ile Leu Leu Lys Pro Ser
    210                 215                 220

Met Val Thr Pro Gly Ala Glu His Lys Glu Lys Ala Ser Pro Glu Ala
225                 230                 235                 240
```

```
Ile Ala Lys Asn Thr Leu Thr Met Leu Arg Arg Val Pro Pro Ala
                245                 250                 255

Val Pro Gly Ile Met Phe Leu Ser Gly Gly Gln Ser Glu Leu Glu Ala
            260                 265                 270

Thr Met Asn Leu Asn Ala Met Asn Gln Ser Ala Asn Pro Trp His Val
        275                 280                 285

Ser Phe Ser Tyr Ala Arg Ala Leu Gln Asn Ser Val Leu Lys Thr Trp
    290                 295                 300

Gln Gly Gln Pro Glu Asn Ile Glu Ala Ala Gln Lys Ala Leu Leu Val
305                 310                 315                 320

Arg Ala Lys Ala Asn Ser Leu Ala Gln Leu Gly Ser Tyr Thr Gly Glu
                325                 330                 335

Gly Glu Ser Asp Glu Ala Lys Lys Gly Met Phe Gln Lys Gly Tyr Thr
            340                 345                 350

Tyr

<210> SEQ ID NO 19
<211> LENGTH: 244
<212> TYPE: PRT
<213> ORGANISM: Hordeum vulgare

<400> SEQUENCE: 19

Ala Ser Ala Tyr Ala Asp Glu Leu Val Lys Thr Ala Lys Thr Ile Ala
1               5                   10                  15

Ser Pro Gly Arg Gly Ile Leu Ala Met Asp Glu Ser Asn Ala Thr Cys
            20                  25                  30

Gly Lys Arg Leu Ala Ser Ile Gly Leu Glu Asn Thr Glu Ala Asn Arg
        35                  40                  45

Gln Ala Tyr Arg Thr Leu Leu Val Thr Pro Pro Gly Leu Gly Asn Tyr
    50                  55                  60

Ile Ser Gly Ala Ile Leu Phe Glu Glu Thr Leu Tyr Gln Ser Thr Val
65                  70                  75                  80

Asp Gly Lys Lys Ile Val Asp Ile Leu Val Glu Gln Gly Ile Val Pro
                85                  90                  95

Gly Ile Lys Val Asp Lys Gly Leu Val Pro Ile Val Gly Ser Asn Asp
            100                 105                 110

Glu Ser Trp Cys Gln Gly Leu Asp Gly Leu Ala Ser Arg Glu Ala Ala
        115                 120                 125

Tyr Cys Gln Gln Gly Ala Arg Phe Ala Lys Trp Arg Thr Val Val Ser
    130                 135                 140

Ile Pro Asn Gly Pro Ser Glu Leu Ala Val Lys Glu Ala Ala Trp Gly
145                 150                 155                 160

Leu Ala Arg Tyr Ala Ala Ile Ser Gln Asp Asn Gly Leu Val Pro Ile
                165                 170                 175

Val Glu Pro Glu Ile Met Leu Asp Gly Glu His Gly Ile Glu Arg Thr
            180                 185                 190

Phe Glu Val Ala Gln Lys Val Trp Ala Glu Thr Phe Tyr Tyr Met Ala
        195                 200                 205

Gln Asn Asn Val Met Phe Glu Gly Ile Leu Leu Lys Pro Ser Met Val
    210                 215                 220

Thr Pro Gly Ala Glu Cys Lys Asp Arg Ala Thr Pro Glu Glu Val Ala
225                 230                 235                 240

Ser Pro Gln Val

<210> SEQ ID NO 20
```

```
<211> LENGTH: 351
<212> TYPE: PRT
<213> ORGANISM: Hordeum vulgare

<400> SEQUENCE: 20

Ala Gly Ala Tyr Asp Asp Glu Leu Val Lys Thr Ala Lys Thr Ile Ala
1               5                   10                  15

Ser Pro Gly Arg Gly Ile Leu Ala Met Asp Glu Ser Asn Ala Thr Cys
            20                  25                  30

Gly Lys Arg Leu Asp Ser Ile Gly Leu Glu Asn Thr Glu Ala Asn Arg
        35                  40                  45

Gln Ala Phe Arg Thr Leu Leu Val Ser Val Pro Gly Leu Gly Asn His
    50                  55                  60

Ile Ser Gly Ala Ile Leu Phe Glu Glu Thr Leu Tyr Gln Ser Thr Val
65                  70                  75                  80

Asp Gly Lys Lys Ile Val Asp Ile Leu Ala Glu Gln Gly Ile Val Pro
                85                  90                  95

Gly Ile Lys Val Asp Lys Gly Leu Val Pro Leu Thr Gly Ser Asn Asp
            100                 105                 110

Glu Ser Trp Cys Gln Gly Leu Asp Gly Leu Ala Ser Arg Glu Ala Ala
        115                 120                 125

Tyr Tyr Gln Gln Gly Ala Arg Phe Ala Lys Trp Arg Thr Val Val Ser
    130                 135                 140

Ile Pro Asn Gly Pro Ser Glu Leu Ala Val Lys Glu Ala Ala Trp Gly
145                 150                 155                 160

Leu Ala Arg Tyr Ala Ala Ile Ser Gln Asp Asn Gly Leu Val Pro Ile
                165                 170                 175

Val Glu Pro Glu Ile Leu Leu Asp Gly Glu His Gly Ile Gly Arg Thr
            180                 185                 190

Phe Glu Val Ala Gln Lys Val Trp Ala Glu Thr Phe Tyr Gln Met Ser
        195                 200                 205

Gln Asn Asn Val Met Phe Glu Gly Ile Leu Leu Lys Pro Ser Met Val
    210                 215                 220

Thr Pro Gly Ala Glu Cys Lys Asp Arg Ala Thr Pro Glu Gln Val Ala
225                 230                 235                 240

Gly Tyr Thr Leu Lys Leu Leu Ser Arg Arg Val Pro Pro Ala Val Pro
                245                 250                 255

Gly Ile Met Phe Leu Ser Gly Gly Gln Ser Glu Val Glu Ala Thr Leu
            260                 265                 270

Asn Leu Asn Ala Met Asn Gln Gly Pro Asn Pro Trp His Val Ser Phe
        275                 280                 285

Ser Tyr Ala Arg Ala Leu Gln Asn Thr Cys Leu Lys Thr Trp Gly Gly
    290                 295                 300

Arg Pro Glu Asn Val Lys Ala Ala Gln Glu Ala Leu Leu Leu Arg Ala
305                 310                 315                 320

Lys Ala Asn Ser Leu Ala Gln Leu Gly Lys Tyr Thr Ser Asp Gly Glu
                325                 330                 335

Ala Ala Glu Ala Lys Glu Gly Met Phe Val Lys Asn Tyr Ser Tyr
            340                 345                 350

<210> SEQ ID NO 21
<211> LENGTH: 352
<212> TYPE: PRT
<213> ORGANISM: Lycopersicon esculentum

<400> SEQUENCE: 21
```

-continued

```
Ala Ala Gly Ser Tyr Thr Asp Glu Leu Ile Lys Thr Ala Lys Thr Ile
1               5                   10                  15

Ala Ser Pro Gly Arg Gly Ile Leu Ala Ile Asp Glu Ser Asn Ala Thr
            20                  25                  30

Ala Gly Lys Arg Leu Ala Ser Ile Gly Leu Asp Asn Thr Glu Ala Asn
        35                  40                  45

Arg Gln Ala Tyr Arg Gln Leu Leu Leu Thr Thr Pro Gly Leu Gly Asp
    50                  55                  60

Tyr Ile Ser Gly Ser Ile Leu Phe Glu Glu Thr Leu Phe Gln Ser Thr
65                  70                  75                  80

Thr Asp Gly Lys Lys Phe Val Asp Val Leu Arg Asp Gln Lys Ile Val
                85                  90                  95

Pro Gly Ile Lys Val Asp Lys Gly Leu Val Pro Leu Pro Gly Ser Asn
            100                 105                 110

Asn Glu Ser Trp Cys Gln Gly Leu Asp Gly Leu Ala Ser Arg Ser Ala
        115                 120                 125

Glu Tyr Tyr Lys Gln Gly Ala Arg Phe Ala Lys Trp Arg Thr Val Val
    130                 135                 140

Ser Ile Pro Cys Gly Pro Ser Ala Leu Ala Val Lys Glu Ala Ala Trp
145                 150                 155                 160

Gly Leu Ala Arg Tyr Ala Ala Ile Ser Gln Asp Asn Gly Leu Val Pro
                165                 170                 175

Ile Val Glu Pro Glu Ile Leu Leu Asp Gly Asp His Pro Ile Glu Arg
            180                 185                 190

Thr Leu Glu Val Ala Glu Arg Val Trp Ala Glu Val Phe Tyr Tyr Leu
        195                 200                 205

Ala Glu Asn Asn Val Val Phe Glu Gly Ile Leu Leu Lys Pro Ser Met
    210                 215                 220

Val Thr Pro Gly Ala Glu His Lys Glu Lys Ala Thr Pro Glu Thr Ile
225                 230                 235                 240

Ala Lys Tyr Thr Leu Thr Met Leu Arg Arg Arg Val Pro Pro Ala Val
                245                 250                 255

Pro Gly Ile Met Phe Leu Ser Gly Gly Gln Ser Glu Val Glu Ala Thr
            260                 265                 270

Leu Asn Leu His Glu Met Asn Gln Ser Pro Asn Pro Trp His Val Ser
        275                 280                 285

Phe Ser Tyr Ala Arg Ala Leu Gln Asn Thr Val Leu Lys Thr Trp Gln
    290                 295                 300

Gly Arg Pro Glu Asn Val Asp Ala Ala Gln Arg Ala Leu Leu Ile Arg
305                 310                 315                 320

Ala Lys Ala Asn Ser Leu Ala Gln Leu Gly Lys Tyr Ser Ala Glu Gly
                325                 330                 335

Glu Ser Glu Glu Ala Lys Lys Gly Met Phe Val Lys Gly Tyr Thr Tyr
            340                 345                 350
```

<210> SEQ ID NO 22
<211> LENGTH: 351
<212> TYPE: PRT
<213> ORGANISM: Lycopersicon esculentum
<400> SEQUENCE: 22

```
Ala Ser Ser Tyr Ala Asp Glu Leu Val Lys Thr Ala Lys Thr Ile Ala
1               5                   10                  15

Ser Pro Gly Arg Gly Ile Leu Ala Met Asp Glu Ser Asn Ala Thr Cys
            20                  25                  30
```

```
Gly Lys Arg Leu Ala Ser Ile Gly Met Glu Asn Thr Glu Ala Asn Arg
             35                  40                  45

Gln Ala Phe Arg Thr Leu Leu Val Ser Val Pro Gly Leu Gly Glu Tyr
         50                  55                  60

Ile Ser Gly Ala Ile Leu Phe Glu Glu Thr Leu Tyr Gln Ser Thr Val
 65                  70                  75                  80

Glu Gly Lys Lys Met Val Asp Val Leu Val Glu Gln Asn Ile Val Pro
                 85                  90                  95

Gly Ile Lys Val Asp Lys Gly Leu Val Pro Leu Ala Gly Ser Asn Asn
            100                 105                 110

Glu Ser Trp Cys Gln Gly Leu Asp Gly Leu Ala Ser Arg Ser Ala Ala
        115                 120                 125

Tyr Tyr Gln Gln Gly Ala Arg Phe Ala Lys Trp Arg Thr Val Val Ser
    130                 135                 140

Ile Pro Asn Gly Pro Ser Ala Leu Ala Val Lys Glu Ala Ala Trp Gly
145                 150                 155                 160

Leu Ala Arg Tyr Ala Ala Ile Ser Gln Asp Asn Gly Leu Val Pro Ile
                165                 170                 175

Val Glu Pro Glu Ile Leu Leu Asp Gly Glu His Asn Ile Asp Arg Thr
            180                 185                 190

Phe Glu Val Ala Lys Gln Val Trp Ala Glu Val Phe Phe Tyr Leu Ala
        195                 200                 205

Gln Asn Asn Val Met Phe Glu Gly Ile Leu Leu Lys Pro Ser Met Val
    210                 215                 220

Thr Pro Gly Ala Glu Cys Lys Asp Arg Ala Thr Pro Gln Gln Val Ala
225                 230                 235                 240

Asp Tyr Thr Leu Ser Leu Leu Arg Gln Arg Ile Pro Pro Ala Val Pro
                245                 250                 255

Gly Ile Met Phe Leu Ser Gly Gly Gln Ser Glu Val Glu Ala Thr Leu
            260                 265                 270

Asn Leu Asn Ala Met Asn Gln Ser Pro Asn Pro Trp His Val Ser Phe
        275                 280                 285

Ser Tyr Ala Arg Ala Leu Gln Asn Thr Cys Leu Lys Thr Trp Ser Gly
    290                 295                 300

Arg Pro Glu Asn Val Lys Ala Ala Gln Asp Ala Leu Leu Val Arg Ala
305                 310                 315                 320

Lys Ala Asn Ser Leu Ala Gln Leu Gly Lys Tyr Thr Gly Glu Gly Glu
                325                 330                 335

Ser Asp Glu Ala Lys Lys Gly Met Phe Val Lys Gly Tyr Val Tyr
            340                 345                 350

<210> SEQ ID NO 23
<211> LENGTH: 351
<212> TYPE: PRT
<213> ORGANISM: Lycopersicon esculentum

<400> SEQUENCE: 23

Ala Ser Ser Tyr Ala Asp Glu Leu Val Lys Thr Ala Lys Thr Val Ala
 1               5                  10                  15

Ser Pro Gly Arg Gly Ile Leu Ala Met Asp Glu Ser Asn Ala Thr Cys
             20                  25                  30

Gly Lys Arg Leu Asp Ser Ile Gly Leu Glu Asn Thr Glu Ala Asn Arg
             35                  40                  45

Gln Ala Tyr Arg Thr Leu Leu Val Ser Ala Pro Gly Leu Gly Asn Tyr
         50                  55                  60
```

```
Ile Ser Gly Ala Ile Leu Phe Glu Glu Thr Leu Tyr Gln Ser Thr Val
 65                  70                  75                  80

Asp Gly Lys Lys Ile Val Asp Val Leu Leu Glu Gln Asn Ile Val Pro
                 85                  90                  95

Gly Ile Lys Val Asp Lys Gly Leu Val Pro Leu Ala Gly Ser Asn Asn
            100                 105                 110

Glu Ser Trp Cys Gln Gly Leu Asp Gly Leu Ala Ser Arg Ser Ala Ala
        115                 120                 125

Tyr Tyr Gln Gln Gly Ala Arg Phe Ala Lys Trp Arg Thr Val Val Ser
130                 135                 140

Ile Pro Asn Gly Pro Ser Ala Leu Ala Val Lys Glu Ala Ala Trp Gly
145                 150                 155                 160

Leu Ala Arg Tyr Ala Ala Ile Ser Gln Asp Asn Gly Leu Val Pro Ile
                165                 170                 175

Val Glu Pro Glu Ile Leu Leu Asp Gly Glu His Asn Ile Asp Arg Thr
            180                 185                 190

Phe Glu Val Ala Gln Gln Val Trp Ala Glu Val Phe Phe Tyr Leu Ala
        195                 200                 205

Glu Asn Asn Val Met Phe Glu Gly Ile Leu Leu Lys Pro Ser Met Val
210                 215                 220

Thr Pro Gly Ala Glu Cys Lys Glu Arg Ala Thr Pro Glu Gln Val Ala
225                 230                 235                 240

Asp Tyr Thr Leu Lys Leu Leu Gln Arg Ile Pro Pro Ala Val Pro
                245                 250                 255

Gly Ile Met Phe Leu Ser Gly Gln Ser Glu Val Ala Thr Leu
            260                 265                 270

Asn Leu Asn Ala Met Asn Gln Ser Pro Asn Pro Trp His Val Ser Phe
        275                 280                 285

Ser Tyr Ala Arg Ala Leu Gln Asn Thr Cys Leu Lys Thr Trp Gly Gly
290                 295                 300

Arg Pro Glu Asn Val Glu Ala Ala Gln Lys Ala Leu Leu Thr Arg Ala
305                 310                 315                 320

Ser Ala Asn Ser Leu Ala Gln Leu Gly Lys Tyr Thr Gly Glu Gly Glu
                325                 330                 335

Ser Glu Glu Ala Lys Glu Gly Met Phe Val Lys Gly Tyr Val Tyr
            340                 345                 350

<210> SEQ ID NO 24
<211> LENGTH: 339
<212> TYPE: PRT
<213> ORGANISM: Lotus japonicus

<400> SEQUENCE: 24

Lys Thr Ile Ala Ser Pro Gly Arg Gly Ile Leu Ala Ile Asp Glu Ser
  1               5                  10                  15

Asn Ala Thr Ala Gly Lys Arg Leu Ala Ser Ile Gly Leu Asp Asn Thr
                 20                  25                  30

Glu Thr Asn Arg Gln Ala Tyr Arg Gln Leu Leu Leu Thr Thr Pro Gly
             35                  40                  45

Leu Gly Glu Tyr Ile Ser Gly Ala Ile Phe Phe Glu Glu Thr Leu Tyr
 50                  55                  60

Gln Ser Thr Thr Asp Gly Lys Lys Phe Val Asp Cys Leu Arg Glu Glu
 65                  70                  75                  80

Asn Ile Val Pro Gly Ile Lys Val Asp Lys Gly Leu Val Pro Leu Pro
                 85                  90                  95
```

```
Gly Ser Asn Asn Glu Ser Trp Cys Gln Gly Leu Asp Gly Leu Ala Ser
                100                 105                 110

Arg Ser Ala Glu Tyr Tyr Lys Gln Gly Ala Arg Phe Ala Lys Trp Arg
            115                 120                 125

Thr Val Val Ser Ile Pro Cys Gly Pro Ser Ala Leu Ala Val Lys Glu
        130                 135                 140

Ala Ala Trp Gly Leu Ala Arg Tyr Ala Ala Ile Ser Gln Asp Asn Gly
145                 150                 155                 160

Leu Val Pro Ile Val Glu Pro Glu Ile Leu Leu Asp Gly Asp His Pro
                165                 170                 175

Ile Glu Arg Thr Leu Glu Val Ala Glu Lys Val Trp Ser Glu Val Phe
            180                 185                 190

Phe Tyr Leu Ala Glu Asn Asn Val Val Phe Glu Gly Ile Leu Leu Lys
        195                 200                 205

Pro Ser Met Val Thr Pro Gly Ala Glu His Lys Gln Lys Ala Ser Pro
        210                 215                 220

Glu Thr Ile Ala Asn Asn Thr Leu Thr Met Leu Arg Arg Val Pro
225                 230                 235                 240

Pro Ala Val Pro Gly Ile Met Phe Leu Ser Gly Gly Gln Ser Glu Val
                245                 250                 255

Glu Ala Thr Leu Asn Leu Asn Ala Met Asn Gln Ser Pro Asn Pro Trp
            260                 265                 270

His Val Ser Phe Ser Tyr Ala Arg Ala Leu Gln Asn Thr Val Leu Lys
        275                 280                 285

Thr Trp Gln Gly Arg Pro Glu Asn Val Glu Ala Ala Gln Lys Ser Leu
        290                 295                 300

Leu Ile Arg Ala Lys Ala Asn Ser Leu Ala Gln Leu Gly Arg Tyr Ser
305                 310                 315                 320

Ala Glu Gly Glu Ser Glu Glu Ala Gln Lys Gly Met Phe Val Lys Gly
                325                 330                 335

Tyr Thr Tyr

<210> SEQ ID NO 25
<211> LENGTH: 351
<212> TYPE: PRT
<213> ORGANISM: Lotus japonicus

<400> SEQUENCE: 25

Ala Gly Ser Tyr Ala Asp Glu Leu Val Lys Thr Ala Lys Thr Val Ala
1               5                   10                  15

Ser Pro Gly Arg Gly Ile Leu Ala Met Asp Glu Ser Asn Ala Thr Cys
            20                  25                  30

Gly Lys Arg Leu Ala Ser Ile Gly Leu Glu Asn Thr Glu Val Asn Arg
        35                  40                  45

Gln Ala Tyr Arg Thr Leu Leu Val Ser Ala Pro Gly Leu Gly Gln Tyr
    50                  55                  60

Ile Ser Gly Ala Ile Leu Phe Glu Glu Thr Leu Tyr Gln Ser Thr Thr
65                  70                  75                  80

Asp Gly Arg Lys Ile Val Asp Val Leu Ile Glu Gln Asn Ile Val Pro
                85                  90                  95

Gly Ile Lys Val Asp Lys Gly Leu Val Pro Leu Ala Gly Ser Asn Asp
            100                 105                 110

Glu Ser Trp Cys Gln Gly Leu Asp Gly Leu Ala Ser Arg Ser Ala Ala
        115                 120                 125

Tyr Tyr Gln Gln Gly Ala Arg Phe Ala Lys Trp Arg Thr Val Val Ser
```

```
                    130                 135                 140
Ile Pro Asn Gly Pro Thr Ala Leu Ala Val Lys Glu Ala Ala Trp Gly
145                 150                 155                 160

Leu Ala Arg Tyr Ala Ala Ile Ser Gln Asp Asn Gly Leu Val Pro Ile
                165                 170                 175

Val Glu Pro Glu Ile Leu Leu Asp Gly Glu His Asp Ile Glu Arg Thr
            180                 185                 190

Phe Glu Val Ala Gln Lys Val Trp Ala Glu Val Phe Phe Tyr Leu Ala
        195                 200                 205

Glu Asn Asn Val Leu Phe Glu Gly Ile Leu Leu Lys Pro Ser Met Val
    210                 215                 220

Thr Pro Gly Ala Glu Ser Lys Asp Lys Val Ser Pro Gln Thr Val Ser
225                 230                 235                 240

Asp Tyr Thr Leu Lys Leu Leu Lys Arg Ile Pro Pro Ala Val Pro
                245                 250                 255

Gly Ile Met Phe Leu Ser Gly Gln Ser Glu Val Glu Ala Thr Leu
            260                 265                 270

Asn Leu Asn Ala Met Asn Gln Ser Pro Asn Pro Trp His Val Ser Phe
        275                 280                 285

Ser Phe Ala Arg Ala Leu Gln Asn Thr Ala Leu Lys Thr Trp Gly Gly
    290                 295                 300

Arg Ala Glu Asn Val Lys Ala Ala Gln Asp Ala Leu Leu Phe Arg Ala
305                 310                 315                 320

Lys Ser Asn Ser Leu Ala Gln Leu Gly Lys Tyr Asn Gly Asp Gly Glu
                325                 330                 335

Ser Glu Glu Ala Lys Lys Glu Leu Phe Val Lys Gly Tyr Ser Tyr
            340                 345                 350

<210> SEQ ID NO 26
<211> LENGTH: 351
<212> TYPE: PRT
<213> ORGANISM: Lotus japonicus

<400> SEQUENCE: 26

Ala Gly Ser Tyr Ala Asp Glu Leu Val Lys Thr Ala Lys Thr Val Ala
1               5                   10                  15

Ser Pro Gly Arg Gly Ile Leu Ala Met Asp Glu Ser Asn Ala Thr Cys
            20                  25                  30

Gly Lys Arg Leu Ala Ser Ile Gly Leu Glu Asn Thr Glu Val Asn Arg
        35                  40                  45

Gln Ala Trp Arg Thr Leu Leu Val Thr Ala Pro Gly Leu Gly Gln Tyr
    50                  55                  60

Val Ser Gly Ala Ile Leu Phe Glu Glu Thr Leu Tyr Gln Ser Thr Thr
65                  70                  75                  80

Asp Gly Arg Lys Ile Val Asp Val Leu Ile Glu Gln Asn Ile Val Pro
                85                  90                  95

Gly Ile Lys Val Asp Lys Gly Leu Val Pro Leu Ala Gly Ser Asn Asp
            100                 105                 110

Glu Ser Trp Cys Gln Gly Leu Asp Gly Leu Ala Ser Arg Thr Ala Ala
        115                 120                 125

Tyr Tyr Gln Gln Gly Ala Arg Phe Ala Lys Trp Arg Thr Val Val Ser
    130                 135                 140

Ile Pro Asn Gly Pro Thr Ala Leu Ala Val Lys Glu Ala Ala Trp Gly
145                 150                 155                 160

Leu Ala Arg Tyr Ala Ala Ile Ala Gln Asp Asn Gly Leu Val Pro Ile
```

```
                      165                 170                 175
Val Glu Pro Glu Ile Leu Leu Asp Gly Glu His Gly Ile Glu Arg Thr
            180                 185                 190

Phe Glu Val Ala Gln Lys Val Trp Ala Glu Val Phe Phe Tyr Leu Ala
        195                 200                 205

Glu Asn Asn Val Leu Phe Glu Gly Ile Leu Leu Lys Pro Ser Met Val
    210                 215                 220

Thr Pro Gly Ala Glu Ser Lys Asp Lys Val Ser Pro Gln Gln Val Ser
225                 230                 235                 240

Asp Tyr Thr Leu Lys Leu Leu Gln Arg Arg Ile Pro Pro Ala Val Pro
                245                 250                 255

Gly Ile Met Phe Leu Ser Gly Gly Gln Ser Glu Val Glu Ala Thr Leu
            260                 265                 270

Asn Leu Asn Ala Met Asn Gln Ser Pro Asn Pro Trp His Val Ser Phe
        275                 280                 285

Ser Phe Ala Arg Ala Leu Gln Asn Thr Ala Leu Lys Thr Trp Gly Gly
    290                 295                 300

Arg Ala Glu Asn Val Lys Ala Ala Gln Asp Ala Leu Leu Phe Arg Ala
305                 310                 315                 320

Lys Ser Asn Ser Leu Ala Gln Leu Gly Lys Tyr Thr Gly Asp Gly Glu
                325                 330                 335

Ser Glu Glu Ala Lys Lys Glu Leu Phe Val Lys Gly Tyr Ser Tyr
            340                 345                 350

<210> SEQ ID NO 27
<211> LENGTH: 353
<212> TYPE: PRT
<213> ORGANISM: Oryza sativa

<400> SEQUENCE: 27

Ala Ala Ala Val Ser Tyr Ala Asp Glu Leu Val Ser Thr Ala Lys Ser
1               5                   10                  15

Val Ala Ser Pro Gly Arg Gly Ile Leu Ala Ile Asp Glu Ser Asn Ala
            20                  25                  30

Thr Cys Gly Lys Arg Leu Ala Ser Ile Gly Leu Asp Asn Thr Glu Val
        35                  40                  45

Asn Arg Gln Ala Tyr Arg Gln Leu Leu Leu Thr Thr Ala Gly Leu Gly
    50                  55                  60

Glu Tyr Ile Ser Gly Ala Ile Leu Phe Glu Glu Thr Leu Tyr Gln Ser
65                  70                  75                  80

Thr Thr Asp Gly Lys Lys Phe Val Asp Cys Leu Lys Asp Gln Asn Ile
                85                  90                  95

Met Pro Gly Ile Lys Val Asp Lys Gly Leu Val Pro Leu Pro Gly Ser
            100                 105                 110

Asn Asn Glu Ser Trp Cys Gln Gly Leu Asp Gly Leu Ala Ser Arg Cys
        115                 120                 125

Ala Glu Tyr Tyr Lys Gln Gly Ala Arg Phe Ala Lys Trp Arg Thr Val
    130                 135                 140

Val Ser Ile Pro Cys Gly Pro Ser Ala Leu Ala Val Lys Glu Ala Ala
145                 150                 155                 160

Trp Gly Leu Ala Arg Tyr Ala Ala Ile Ala Gln Asp Asn Gly Leu Val
                165                 170                 175

Pro Ile Val Glu Pro Glu Ile Leu Leu Asp Gly Asp His Ala Ile Glu
            180                 185                 190

Arg Thr Leu Glu Val Ala Glu Lys Val Trp Ser Glu Val Phe Phe Tyr
```

```
                      195                 200                 205
Leu Ala Gln Asn Asn Val Leu Phe Glu Gly Ile Leu Leu Lys Pro Ser
    210                 215                 220

Met Val Thr Pro Gly Ala Glu His Lys Gln Lys Ala Thr Pro Glu Ala
225                 230                 235                 240

Ile Ala Lys His Thr Leu Thr Met Leu Arg Arg Val Pro Pro Ala
                245                 250                 255

Val Pro Gly Ile Met Phe Leu Ser Gly Gln Ser Glu Val Glu Ala
                260                 265                 270

Thr Leu Asn Leu Asn Ala Met Asn Gln Glu Pro Asn Pro Trp His Val
                275                 280                 285

Ser Phe Ser Tyr Ala Arg Ala Leu Gln Asn Ser Val Leu Lys Thr Trp
    290                 295                 300

Gln Gly Arg Pro Glu Asn Val Glu Ala Ala Gln Lys Ala Leu Leu Val
305                 310                 315                 320

Arg Ala Lys Ala Asn Ser Leu Ala Gln Leu Gly Arg Tyr Thr Gly Glu
                325                 330                 335

Gly Glu Ser Asp Glu Ala Lys Lys Gly Met Phe Gln Lys Gly Tyr Thr
                340                 345                 350

Tyr

<210> SEQ ID NO 28
<211> LENGTH: 351
<212> TYPE: PRT
<213> ORGANISM: Oryza sativa

<400> SEQUENCE: 28

Ala Gly Ala Tyr Asp Asp Glu Leu Val Lys Thr Ala Lys Thr Ile Ala
1               5                   10                  15

Ser Pro Gly Arg Gly Ile Leu Ala Met Asp Glu Ser Asn Ala Thr Cys
                20                  25                  30

Gly Lys Arg Leu Ala Ser Ile Gly Leu Glu Asn Thr Glu Ala Asn Arg
            35                  40                  45

Gln Ala Tyr Arg Thr Leu Leu Val Thr Ala Pro Gly Leu Gly Gln Tyr
        50                  55                  60

Ile Ser Gly Ala Ile Leu Phe Glu Glu Thr Leu Tyr Gln Ser Thr Val
65                  70                  75                  80

Asp Gly Lys Lys Ile Val Asp Ile Leu Thr Glu Gln Lys Ile Val Pro
                85                  90                  95

Gly Ile Lys Val Asp Lys Gly Leu Val Pro Leu Ala Gly Ser Asn Asn
                100                 105                 110

Glu Ser Trp Cys Gln Gly Leu Asp Gly Leu Ala Ser Arg Glu Ala Ala
            115                 120                 125

Tyr Tyr Gln Gln Gly Ala Arg Phe Ala Lys Trp Arg Thr Val Val Ser
        130                 135                 140

Ile Pro Asn Gly Pro Ser Glu Leu Ala Val Lys Glu Ala Ala Trp Gly
145                 150                 155                 160

Leu Ala Arg Tyr Ala Ala Ile Ser Gln Asp Asn Gly Leu Val Pro Ile
                165                 170                 175

Val Glu Pro Glu Ile Leu Leu Asp Gly Glu His Gly Ile Asp Arg Thr
                180                 185                 190

Phe Glu Val Ala Gln Lys Val Trp Ala Glu Thr Phe Phe Tyr Met Ala
            195                 200                 205

Glu Asn Asn Val Met Phe Glu Gly Ile Leu Leu Lys Pro Ser Met Val
        210                 215                 220
```

```
Thr Pro Gly Ala Glu Cys Lys Asp Arg Ala Thr Pro Glu Gln Val Ser
225                 230                 235                 240

Asp Tyr Thr Leu Lys Leu Leu His Arg Arg Ile Pro Pro Ala Val Pro
                245                 250                 255

Gly Ile Met Phe Leu Ser Gly Gly Gln Ser Glu Val Glu Ala Thr Gln
            260                 265                 270

Asn Leu Asn Ala Met Asn Gln Gly Pro Asn Pro Trp His Val Ser Phe
        275                 280                 285

Ser Tyr Ala Arg Ala Leu Gln Asn Thr Cys Leu Lys Thr Trp Gly Gly
    290                 295                 300

Gln Pro Glu Asn Val Lys Ala Ala Gln Asp Ala Leu Leu Leu Arg Ala
305                 310                 315                 320

Lys Ala Asn Ser Leu Ala Gln Leu Gly Lys Tyr Thr Ser Asp Gly Glu
                325                 330                 335

Ala Ala Glu Ala Lys Glu Gly Met Phe Val Lys Asn Tyr Val Tyr
            340                 345                 350
```

<210> SEQ ID NO 29
<211> LENGTH: 351
<212> TYPE: PRT
<213> ORGANISM: Picea sitchensis

<400> SEQUENCE: 29

```
Ala Gly Ser Tyr Ala Glu Glu Leu Val Gln Thr Ala Lys Thr Val Ala
1               5                   10                  15

Ser Pro Gly Arg Gly Ile Leu Ala Ile Asp Glu Ser Asn Ala Thr Cys
            20                  25                  30

Gly Lys Arg Leu Ala Ser Ile Gly Leu Glu Asn Asn Glu Thr Asn Arg
        35                  40                  45

Gln Ala Tyr Arg Gln Leu Leu Leu Thr Thr Pro Gly Leu Gly Glu Tyr
    50                  55                  60

Ile Ser Gly Ser Ile Leu Phe Glu Glu Thr Leu Tyr Gln Ser Thr Thr
65                  70                  75                  80

Asp Gly Arg Lys Phe Val Asp Cys Leu Arg Glu Gln Asn Ile Met Pro
                85                  90                  95

Gly Ile Lys Val Asp Lys Gly Leu Val Pro Leu Pro Gly Ser Asn Asn
            100                 105                 110

Glu Ser Trp Cys Gln Gly Leu Asp Gly Leu Ala Ser Arg Ser Ala Glu
        115                 120                 125

Tyr Tyr Lys Gln Gly Ala Arg Phe Ala Lys Trp Arg Thr Val Val Ser
    130                 135                 140

Ile Pro Asn Gly Pro Ser Asp Leu Ala Val Lys Glu Ala Ala Trp Gly
145                 150                 155                 160

Leu Ala Arg Tyr Ala Ala Ile Ser Gln Asp Asn Gly Leu Val Pro Ile
                165                 170                 175

Val Glu Pro Glu Ile Leu Leu Asp Gly Asp His Ser Ile Asp Arg Thr
            180                 185                 190

Leu Glu Val Ala Glu Lys Val Trp Ala Glu Val Phe Phe Tyr Leu Ala
        195                 200                 205

Glu Asn Asn Val Phe Phe Glu Gly Ile Leu Leu Lys Pro Ser Met Val
    210                 215                 220

Thr Pro Gly Ala Glu His Lys Glu Lys Ala Thr Pro Gln Gln Val Ala
225                 230                 235                 240

Asp Tyr Thr Leu Lys Met Leu Lys Arg Arg Val Pro Pro Ala Val Pro
                245                 250                 255
```

-continued

Gly Ile Met Phe Leu Ser Gly Gly Gln Ser Glu Val Glu Ala Thr Leu
              260                 265                 270

Asn Leu Asn Ala Met Asn Gln Ser Pro Asn Pro Trp His Val Ser Phe
            275                 280                 285

Ser Tyr Ala Arg Ala Leu Gln Asn Thr Ser Leu Lys Thr Trp Lys Gly
        290                 295                 300

Leu Pro Glu Asn Ile Glu Ala Ala Gln Arg Ala Leu Leu Ile Arg Ala
305                 310                 315                 320

Lys Ala Asn Ser Leu Ala Gln Leu Gly Arg Tyr Ser Ala Glu Gly Glu
                325                 330                 335

Ser Glu Glu Ser Lys Lys Gly Met Phe Val Lys Gly Tyr Thr Tyr
            340                 345                 350

<210> SEQ ID NO 30
<211> LENGTH: 351
<212> TYPE: PRT
<213> ORGANISM: Picea sitchensis

<400> SEQUENCE: 30

Ala Gly Ala Tyr Ser Glu Glu Leu Ile Lys Thr Ala Lys Arg Val Ala
1               5                   10                  15

Ser Pro Gly Arg Gly Ile Leu Ala Met Asp Glu Ser Asn Ala Thr Cys
            20                  25                  30

Gly Lys Arg Leu Ala Ser Ile Gly Leu Glu Asn Thr Glu Ala Asn Arg
        35                  40                  45

Gln Ala Tyr Arg Gln Leu Leu Val Ser Ala Pro Gly Leu Gly Gln Tyr
    50                  55                  60

Ile Ser Gly Ser Ile Leu Phe Glu Glu Thr Leu Tyr Gln Ser Thr Thr
65                  70                  75                  80

Asp Gly Lys Lys Met Val Asp Val Leu Val Gln Gln Asp Ile Val Pro
                85                  90                  95

Gly Ile Lys Val Asp Lys Gly Leu Val Pro Leu Ala Gly Ser Asn Asp
            100                 105                 110

Glu Ser Trp Cys Gln Gly Leu Asp Gly Leu Ala Ser Arg Cys Ala Ala
        115                 120                 125

Tyr Tyr Gln Gln Gly Ala Arg Phe Ala Lys Trp Arg Thr Val Val Ser
    130                 135                 140

Ile Pro Asn Gly Pro Ser Ala Leu Ala Val Lys Glu Ala Ala Trp Gly
145                 150                 155                 160

Leu Ala Arg Tyr Ala Ala Ile Ala Gln Asp Asn Gly Leu Val Pro Ile
                165                 170                 175

Val Glu Pro Glu Ile Leu Leu Asp Gly Glu His Gly Leu Glu Arg Thr
            180                 185                 190

Phe Glu Val Ala Leu Lys Val Trp Ala Glu Val Phe Phe Tyr Leu Ala
        195                 200                 205

Glu Asn Asn Val Leu Phe Glu Gly Ile Leu Leu Lys Pro Ser Met Val
    210                 215                 220

Thr Pro Gly Ala Glu Cys Lys Asp Arg Ala Ser Pro Glu Thr Val Ala
225                 230                 235                 240

Gln Tyr Thr Leu Asn Leu Leu Arg Arg Arg Val Pro Pro Ala Val Pro
                245                 250                 255

Gly Ile Met Phe Leu Ser Gly Gly Gln Ser Glu Val Glu Ala Thr Leu
            260                 265                 270

Asn Leu Asn Ala Met Asn Gln Ala Pro Asn Pro Trp His Val Ser Phe
        275                 280                 285

Ser Tyr Ala Arg Ala Leu Gln Asn Thr Cys Leu Lys Thr Trp Ala Gly
            290                 295                 300

Arg Pro Glu Asn Val Asp Ala Ala Gln Lys Ile Leu Leu Val Arg Ala
305                 310                 315                 320

Lys Ala Asn Ser Leu Ala Gln Leu Gly Lys Tyr Ser Ala Glu Gly Glu
            325                 330                 335

Ser Ala Glu Ser Lys Glu Gly Met Phe Val Lys Gly Tyr Thr Tyr
            340                 345                 350

<210> SEQ ID NO 31
<211> LENGTH: 351
<212> TYPE: PRT
<213> ORGANISM: Populus trichocarpa

<400> SEQUENCE: 31

Ala Asn Ser Tyr Thr Asp Glu Leu Val Gln Thr Ala Lys Thr Ile Ala
1               5                   10                  15

Ser Pro Gly Arg Gly Ile Leu Ala Ile Asp Glu Ser Asn Ala Thr Cys
            20                  25                  30

Gly Lys Arg Leu Ala Ser Ile Gly Leu Asp Asn Thr Glu Thr Asn Arg
            35                  40                  45

Gln Ala Tyr Arg Gln Leu Leu Leu Thr Thr Pro Ser Leu Gly Glu Tyr
50                  55                  60

Ile Ser Gly Ala Ile Leu Phe Glu Glu Thr Leu Tyr Gln Ser Thr Thr
65                  70                  75                  80

Asp Gly Lys Lys Phe Val Asp Cys Leu Arg Asp Glu Asn Ile Val Pro
                85                  90                  95

Gly Ile Lys Val Asp Lys Gly Leu Val Pro Leu Pro Gly Ser Asn Asn
            100                 105                 110

Glu Ser Trp Cys Gln Gly Leu Asp Gly Leu Ala Ser Arg Ser Ala Glu
            115                 120                 125

Tyr Tyr Lys Gln Gly Ala Arg Phe Ala Lys Trp Arg Thr Val Val Ser
130                 135                 140

Ile Pro Cys Gly Pro Ser Ala Leu Ala Val Lys Glu Ala Ala Trp Gly
145                 150                 155                 160

Leu Ala Arg Tyr Ala Ala Ile Ser Gln Asp Asn Gly Leu Val Pro Ile
                165                 170                 175

Val Glu Pro Glu Ile Leu Leu Asp Gly Asp His Pro Ile Asp Arg Thr
            180                 185                 190

Leu Glu Val Ala Glu Lys Val Trp Ser Gly Val Phe Tyr Tyr Leu Ala
            195                 200                 205

Glu Asn Asn Val Val Phe Glu Gly Ile Leu Leu Lys Pro Ser Met Val
210                 215                 220

Thr Pro Gly Ala Glu His Lys Glu Lys Ala Ser Ala Asp Thr Ile Ala
225                 230                 235                 240

Lys Tyr Thr Leu Thr Met Leu Lys Arg Val Pro Pro Ala Val Pro
                245                 250                 255

Gly Ile Met Phe Leu Ser Gly Gly Gln Ser Glu Val Gln Ala Thr Leu
            260                 265                 270

Asn Leu Asn Ala Met Asn Gln Ser Pro Asn Pro Trp His Val Ser Phe
            275                 280                 285

Ser Tyr Ala Arg Ala Leu Gln Asn Thr Val Leu Lys Thr Trp Gln Gly
            290                 295                 300

Arg Pro Asp Asn Val Glu Ala Ala Gln Lys Ser Leu Leu Val Arg Ala
305                 310                 315                 320

```
Lys Ala Asn Ser Leu Ala Gln Leu Gly Arg Tyr Ser Ala Glu Gly Glu
            325                 330                 335

Ser Glu Glu Ala Thr Lys Gly Met Phe Val Lys Gly Tyr Thr Tyr
            340                 345                 350

<210> SEQ ID NO 32
<211> LENGTH: 351
<212> TYPE: PRT
<213> ORGANISM: Populus trichocarpa

<400> SEQUENCE: 32

Ala Gly Ser Tyr Ala Asp Glu Leu Val Lys Thr Ala Lys Thr Ile Ala
1               5                   10                  15

Ser Pro Gly Arg Gly Ile Leu Ala Met Asp Glu Ser Asn Ala Thr Cys
            20                  25                  30

Gly Lys Arg Leu Ala Ser Ile Gly Leu Glu Asn Thr Glu Ala Asn Arg
        35                  40                  45

Gln Ala Tyr Arg Thr Leu Leu Val Thr Val Pro Gly Leu Gly Asn Tyr
    50                  55                  60

Val Ser Gly Ala Ile Leu Phe Glu Glu Thr Leu Tyr Gln Ser Thr Thr
65                  70                  75                  80

Asp Gly Lys Lys Met Val Asp Val Leu Val Glu Gln Lys Ile Val Pro
                85                  90                  95

Gly Ile Lys Val Asp Lys Gly Leu Val Pro Leu Ala Gly Ser Asn Asp
            100                 105                 110

Glu Ser Trp Cys Gln Gly Leu Asp Gly Leu Ala Ser Arg Ser Ala Ala
        115                 120                 125

Tyr Tyr Gln Gln Gly Ala Arg Phe Ala Lys Trp Arg Thr Val Val Ser
    130                 135                 140

Ile Pro Asn Gly Pro Ser Ala Leu Ala Val Lys Glu Ala Ala Trp Gly
145                 150                 155                 160

Leu Ala Arg Tyr Ala Ala Ile Ser Gln Asp Asn Gly Leu Val Pro Ile
                165                 170                 175

Val Glu Pro Glu Ile Leu Leu Asp Gly Glu His Gly Ile Glu Arg Thr
            180                 185                 190

Phe Glu Val Ala Gln Lys Val Trp Ala Glu Val Phe Tyr Tyr Met Ala
        195                 200                 205

Glu Asn Asn Val Met Phe Glu Gly Ile Leu Leu Lys Pro Ser Met Val
    210                 215                 220

Thr Pro Gly Ala Glu Cys Lys Asp Arg Ala Ser Pro Asp Gln Val Ala
225                 230                 235                 240

Glu Tyr Thr Leu Lys Leu Leu His Arg Arg Ile Pro Pro Ala Val Pro
                245                 250                 255

Gly Ile Met Phe Leu Ser Gly Gly Gln Ser Glu Val Glu Ala Thr Leu
            260                 265                 270

Asn Leu Asn Ala Met Asn Gln Ser Pro Asn Pro Trp His Val Ser Phe
        275                 280                 285

Ser Tyr Ala Arg Ala Leu Gln Asn Thr Cys Leu Lys Thr Trp Gly Gly
    290                 295                 300

Arg Pro Glu Asn Val Gln Asp Ala Gln Glu Thr Leu Leu Ile Arg Ala
305                 310                 315                 320

Lys Ala Asn Ser Leu Ala Gln Leu Gly Lys Tyr Thr Gly Glu Gly Glu
                325                 330                 335

Ser Asp Asp Ala Lys Lys Gly Met Tyr Val Lys Asn Tyr Ser Tyr
            340                 345                 350
```

<210> SEQ ID NO 33
<211> LENGTH: 351
<212> TYPE: PRT
<213> ORGANISM: Populus trichocarpa

<400> SEQUENCE: 33

```
Thr Gly Ser Tyr Ala Glu Glu Leu Val Lys Thr Ala Lys Thr Ile Ala
1               5                   10                  15
Ser Pro Gly Arg Gly Ile Leu Ala Met Asp Glu Ser Asn Ala Thr Cys
            20                  25                  30
Gly Lys Arg Leu Ala Ser Ile Gly Leu Glu Asn Thr Glu Ala Asn Arg
        35                  40                  45
Gln Ala Tyr Arg Thr Leu Leu Val Thr Pro Gly Leu Gly Asp Tyr
    50                  55                  60
Val Ser Gly Ala Ile Leu Phe Glu Glu Thr Leu Tyr Gln Ser Thr Thr
65                  70                  75                  80
Asp Gly Lys Lys Met Val Asp Val Leu Val Glu Gln Lys Ile Val Pro
                85                  90                  95
Gly Ile Lys Val Asp Lys Gly Leu Val Pro Leu Ala Gly Ser Asn Asp
            100                 105                 110
Glu Ser Trp Cys Gln Gly Leu Asp Gly Leu Ala Ser Arg Thr Ala Ala
        115                 120                 125
Tyr Tyr Gln Gln Gly Ala Arg Phe Ala Lys Trp Arg Thr Val Val Ser
    130                 135                 140
Ile Pro Asn Gly Pro Ser Ala Leu Ala Val Lys Glu Ala Ala Trp Gly
145                 150                 155                 160
Leu Ala Arg Tyr Ala Ala Ile Ser Gln Asp Asn Gly Leu Val Pro Ile
                165                 170                 175
Val Glu Pro Glu Ile Leu Leu Asp Gly Glu His Gly Ile Asp Arg Thr
            180                 185                 190
Phe Glu Val Ala Gln Lys Val Trp Ala Glu Val Phe Phe Tyr Met Ala
        195                 200                 205
Glu Asn Asn Val Met Phe Glu Gly Ile Leu Leu Lys Pro Ser Met Val
    210                 215                 220
Thr Pro Gly Ala Glu Cys Lys Asp Arg Ala Thr Pro Glu Gln Val Ala
225                 230                 235                 240
Glu Tyr Thr Leu Lys Leu Leu Gln Arg Arg Ile Pro Pro Ser Val Pro
                245                 250                 255
Gly Ile Met Phe Leu Ser Gly Gly Gln Ser Glu Val Glu Ala Thr Leu
            260                 265                 270
Asn Leu Asn Ala Met Asn Gln Ser Ala Asn Pro Trp His Val Ser Phe
        275                 280                 285
Ser Tyr Ala Arg Ala Leu Gln Asn Thr Cys Leu Lys Thr Trp Gly Gly
    290                 295                 300
Arg Pro Glu Asn Val Asn Ala Ala Gln Glu Ala Leu Leu Ile Arg Ala
305                 310                 315                 320
Lys Ala Asn Ser Leu Ala Gln Leu Gly Lys Tyr Thr Gly Glu Gly Glu
                325                 330                 335
Ser Asp Glu Ala Lys Lys Gly Met Phe Val Lys Asn Tyr Ala Tyr
            340                 345                 350
```

<210> SEQ ID NO 34
<211> LENGTH: 245
<212> TYPE: PRT
<213> ORGANISM: Zea mays

<400> SEQUENCE: 34

```
His Glu Gly Ser Asn Asn Glu Ser Trp Cys Gln Gly Leu Asp Gly Leu
1               5                   10                  15
Ala Ser Arg Cys Ala Glu Tyr Tyr Lys Gln Gly Ala Arg Phe Ala Lys
            20                  25                  30
Trp Arg Thr Val Val Ser Ile Pro Cys Gly Pro Ser Ala Leu Ala Val
        35                  40                  45
Lys Glu Ala Ala Trp Gly Leu Ala Arg Tyr Ala Ala Ile Ala Gln Asp
50                  55                  60
Asn Gly Leu Val Pro Ile Val Glu Pro Glu Ile Leu Leu Asp Gly Asp
65                  70                  75                  80
His Gly Ile Glu Arg Thr Leu Glu Val Ala Glu Lys Val Trp Ser Glu
                85                  90                  95
Val Phe Phe Tyr Leu Ala Gln Asn Asn Val Leu Phe Glu Gly Ile Leu
            100                 105                 110
Leu Lys Pro Ser Met Val Thr Pro Gly Ala Asp His Lys Glu Lys Ala
        115                 120                 125
Ser Pro Glu Ala Ile Ala Lys Tyr Thr Leu Thr Met Leu Arg Arg Arg
130                 135                 140
Val Pro Pro Ala Val Pro Gly Ile Met Phe Leu Ser Gly Gly Gln Ser
145                 150                 155                 160
Glu Val Glu Ala Thr Leu Asn Leu Asn Ala Met Asn Gln Ser Pro Asn
                165                 170                 175
Pro Trp His Val Ser Phe Ser Tyr Ala Arg Ala Leu Gln Asn Ser Val
            180                 185                 190
Leu Lys Thr Trp Gln Gly Arg Pro Glu Asn Val Glu Ala Ala Gln Lys
        195                 200                 205
Ala Leu Leu Val Arg Ala Lys Ala Asn Ser Leu Ala Gln Leu Gly Arg
210                 215                 220
Tyr Thr Gly Glu Gly Glu Ser Asp Glu Ala Lys Lys Gly Met Phe Gln
225                 230                 235                 240
Lys Gly Tyr Thr Tyr
                245
```

<210> SEQ ID NO 35
<211> LENGTH: 350
<212> TYPE: PRT
<213> ORGANISM: Glycine max

<400> SEQUENCE: 35

```
Ala Ser Ser Tyr Gln His Glu Leu Val Gln Thr Ala Lys Ser Ile Ala
1               5                   10                  15
Ser Pro Ser Arg Gly Ile Leu Ala Ile Asp Glu Ser Asn Ala Thr Cys
            20                  25                  30
Gly Lys Arg Leu Ala Ser Ile Gly Leu Asp Asn Thr Glu Val Asn Arg
        35                  40                  45
Gln Ala Tyr Arg Gln Leu Leu Leu Thr Thr Pro Gly Leu Gly Glu Tyr
50                  55                  60
Ile Ser Gly Ala Ile Leu Phe Glu Glu Thr Leu Tyr Gln Ser Thr Thr
65                  70                  75                  80
Asp Gly Asn Lys Phe Val Asp Cys Leu Arg Asp Gln Asn Ile Val Pro
                85                  90                  95
Asp Ile Lys Val Asp Lys Gly Leu Val Pro Leu Pro Gly Ser Asn Asn
            100                 105                 110
```

```
Glu Ser Trp Cys Gly Leu Asp Gly Leu Ala Ser Arg Ser Ala Glu Tyr
            115                 120                 125

Tyr Lys Gln Gly Ala Arg Phe Ala Lys Trp Arg Thr Val Val Ser Ile
    130                 135                 140

Pro Cys Gly Pro Ser Ala Leu Ala Val Lys Glu Ala Ala Trp Gly Leu
145                 150                 155                 160

Ala Arg Tyr Ala Ala Ile Ser Gln Asp Asn Gly Leu Val Pro Ile Val
                165                 170                 175

Glu Pro Glu Ile Leu Leu Asp Gly Asp His Pro Ile Glu Arg Thr Leu
            180                 185                 190

Glu Val Ala Glu Lys Val Trp Ser Glu Val Phe Tyr Leu Ala Glu
        195                 200                 205

Asn Asn Val Leu Phe Glu Gly Ile Leu Leu Lys Pro Ser Met Val Thr
    210                 215                 220

Pro Gly Ala Glu His Thr Glu Lys Ala Ser Pro Glu Thr Ile Ala Lys
225                 230                 235                 240

Tyr Thr Leu Thr Met Leu Arg Arg Arg Val Pro Pro Ala Leu Pro Gly
                245                 250                 255

Ile Met Phe Leu Ser Gly Gly Gln Ser Glu Val Glu Ala Thr Leu Asn
            260                 265                 270

Leu Asn Ala Met Asn Gln Ser Pro Asn Pro Trp His Val Ser Phe Ser
    275                 280                 285

Tyr Ala Arg Ala Leu Gln Asn Thr Val Leu Lys Thr Trp Gln Gly His
290                 295                 300

Pro Glu Asn Val Glu Ala Ala Gln Lys Ser Leu Leu Val Arg Ala Lys
305                 310                 315                 320

Ala Asn Ser Leu Ala Gln Leu Gly Arg Tyr Ser Ala Glu Gly Glu Ser
                325                 330                 335

Glu Glu Ala Lys Lys Gly Met Phe Val Lys Gly Tyr Thr Tyr
            340                 345                 350

<210> SEQ ID NO 36
<211> LENGTH: 358
<212> TYPE: PRT
<213> ORGANISM: Arabidopsis thaliana

<400> SEQUENCE: 36

Met Ser Ala Phe Val Ser Lys Tyr Glu Asp Glu Leu Ile Lys Thr Ala
1               5                   10                  15

Lys Tyr Ile Ala Thr Pro Gly Arg Gly Ile Leu Ala Ala Asp Glu Ser
                20                  25                  30

Thr Glu Thr Ile Gly Lys Arg Phe Ala Gly Ile Asn Val Glu Asn Thr
            35                  40                  45

Glu Ser Asn Arg Gln Ala Tyr Arg Glu Leu Leu Phe Thr Ser Pro Gly
    50                  55                  60

Ser Tyr Pro Cys Leu Ser Gly Val Ile Leu Phe Glu Glu Thr Leu Tyr
65                  70                  75                  80

Gln Lys Thr Ser Asp Gly Lys Pro Phe Val Asp Leu Leu Met Glu Asn
                85                  90                  95

Gly Val Ile Pro Gly Ile Lys Val Asp Lys Gly Leu Val Asp Leu Ala
            100                 105                 110

Gly Thr Asn Gly Glu Thr Thr Thr Gln Gly Leu Asp Ser Leu Gly Ala
    115                 120                 125

Arg Cys Gln Gln Tyr Tyr Glu Ala Gly Ala Arg Phe Ala Lys Trp Arg
130                 135                 140
```

```
Ala Phe Phe Lys Ile Gly Ala Thr Glu Pro Ser Val Leu Ser Ile Gln
145                 150                 155                 160

Glu Asp Ala Arg Val Leu Ala Arg Tyr Ala Ile Ile Cys Gln Glu Asn
                165                 170                 175

Gly Leu Val Pro Ile Val Glu Pro Glu Val Leu Thr Gly Gly Ser His
            180                 185                 190

Asp Ile Lys Lys Cys Ala Ala Val Thr Glu Thr Val Leu Ala Ala Val
        195                 200                 205

Phe Lys Ala Leu Asn Tyr His His Val Leu Leu Glu Gly Thr Leu Leu
    210                 215                 220

Lys Pro Asn Met Val Thr Pro Gly Ser Asp Ser Pro Lys Val Ala Pro
225                 230                 235                 240

Glu Leu Ile Ala Glu Tyr Thr Val Thr Ala Leu Arg Arg Thr Val Pro
                245                 250                 255

Pro Ala Ile Pro Gly Ile Val Phe Leu Ser Gly Ile Gln Arg Glu Glu
            260                 265                 270

Gln Ala Thr Leu Asn Leu Asn Ala Met Asn Lys Leu Asp Val Leu Lys
        275                 280                 285

Pro Trp Thr Leu Thr Phe Ser Phe Gly Gly Ala Leu Gln Gln Ser Ala
290                 295                 300

Ile Lys Ala Trp Ala Gly Lys Pro Glu Asn Val Ala Lys Ala Gln Ala
305                 310                 315                 320

Lys Phe Leu Thr Arg Cys Lys Ala Asn Lys Asp Ala Thr Leu Gly Lys
                325                 330                 335

Tyr Thr Gly Trp Ala Ser Gly Asp Ser Ala Ala Phe Glu Asn Leu Val
            340                 345                 350

Val Ile Gly Tyr Arg Tyr
            355

<210> SEQ ID NO 37
<211> LENGTH: 1056
<212> TYPE: DNA
<213> ORGANISM: Arabidopsis thaliana

<400> SEQUENCE: 37
gccggtgctt actccgacga gcttgttaaa accgccaaaa gcattgcatc ccctgggaga      60
ggtatcttgg cgatcgatga gtccaatgca acctgtggga gaggcttgc ttctatcggc     120 ttggataaca ccgaggacaa ccgtcaggcc tacaggcaac ttctgcttac cactcctggc     180
ctcggcgatt acatctctgg ttccattctc ttcgaggaga ctctttacca gtccaccaag     240
gacggtaaga cctttgtcga ttgcttgcgc gatgccaaca tcgtccctgg catcaaagtt     300
gacaagggct tgtctcccct agccggttcc aacgaagagt cttggtgcca aggcttggat     360
ggattggcct cacgctctgc tgagtactac aagcaaggcg ctcgttttgc caagtggagg     420
acagtggtga tgttccctg cggtccttca gcactggctg tgaaggaagc tgcgtggggg     480
ctggctcgct atgcagccat tctctcagga atggtcttg tccccattgt ggagccagag     540
atccttctgg acgggacca cccaatagag aggactctgg aggtggcaga aaagtgtgg     600 tcagaggtgt tcttctactt ggcacagaac aacgtcatgt ttgagggcat tctgttgaag     660
ccgagcatgg tcaccccagg cgctgagcac aagaacaagg cctctcccga gaccgttgca     720
gatttcacgc tcaccatgct gaaaaggagg gttcctccgg ctgtcccagg gatcatgttt     780
ctgtcaggag acaatcaga ggcagaggcc acactgaacc tgaacgccat gaaccagagc     840
ccaaacccat ggcatgtgtc cttctcatac gcacgtgccc tgcagaactc cgtgctcaga     900
```

| | |
|---|---|
| acatggcaag gcaagccgga gaagattgag gcctcgcaga aggcactgtt ggtgagggca | 960 |
| aaggccaact cactggccca gctcggcaaa tactcagccg agggagagaa cgaggatgcc | 1020 |
| aagaaaggaa tgtttgtcaa gggttacacc tactga | 1056 |

<210> SEQ ID NO 38
<211> LENGTH: 1059
<212> TYPE: DNA
<213> ORGANISM: Arabidopsis thaliana

<400> SEQUENCE: 38

| | |
|---|---|
| gccgcttctg cttacgccga tgagctcgtc aaaaccgcta aaacaatcgc gtctccggga | 60 |
| cacggaatta tggcgatgga tgagtccaac gcgacttgtg aaagcgtttt ggcgtcaatt | 120 |
| gggctagaga acacggaggc taaccgtcaa gcttgcagga cgttgcttgt gtcggctcca | 180 |
| ggacttggac agtacatctc cggagctatc ctgttcgagg agactctgta ccaatccacc | 240 |
| actgatggca agaaaatggt tgatgttctc gtcgagcaga acatcgtccc tggcatcaaa | 300 |
| gtcgacaagg gtttggtgcc acttgttggg tcttacgacg agtcatggtg ccaaggactt | 360 |
| gacggtttag cctctcgcac cgctgcttac taccaacaag gtgctcgttt cgccaaatgg | 420 |
| cgtactgttg tgagcattcc aaatggaccc tctgctttgg ctgttaaaga agcagcttgg | 480 |
| ggacttgctc gctacgcagc tatttctcaa gacagcggtc tggtgccgat gtggagcca | 540 |
| gagattatgt tggacggaga acacggcatt gacaggacat cgacgttgc agagaaggtt | 600 |
| tgggctgagg tcttcttcta cctcgctcag aacaacgtca tgttcgaagg tattctcctg | 660 |
| aagccaagca tggttactcc aggagctgag gccacagaca gagctactcc tgagcaggtt | 720 |
| gcttcctaca ctctcaagct ccttcgcaac agaatccctc ctgctgtccc cggaatcatg | 780 |
| ttcttgtctg gtggacagtc cgagttggag gcgaccttga acttgaacgc aatgaaccag | 840 |
| gcaccgaacc catggcacgt gtccttctcc tacgcacgtg ccttgcagaa cacttgcttg | 900 |
| aagacatggg gaggcaagga agagaacgtg aaggcggctc aggacattct cttggccaga | 960 |
| gccaaagcca attcgctggc tcagctcggg aaatacactg agaaggcga gtctgaggaa | 1020 |
| gccaaggagg gtatgtttgt aaaaggctac acctactaa | 1059 |

<210> SEQ ID NO 39
<211> LENGTH: 1059
<212> TYPE: DNA
<213> ORGANISM: Arabidopsis thaliana

<400> SEQUENCE: 39

| | |
|---|---|
| gccgcttcct cctacgccga tgagcttgtt aagacagcga aaactattgc gtctcccgga | 60 |
| cgtggaatct tggcgatgga cgagtcaaac gcgacttgcg ggaaacgttt ggattcgata | 120 |
| gggctagaga acactgaggc aaatcgtcaa gctttccgga ctttgctggt ctctgcaccg | 180 |
| ggactcggac agtacgtctc cggcgcaatt ctatttgagg agactctgta ccagtctacc | 240 |
| accgaaggca agaaaatggt cgacgtcctc gtcgagcaga acattgtccc tggtatcaaa | 300 |
| gtcgacaagg gtttggtgcc acttgttgga tccaacaatg agtcatggtg ccaaggacta | 360 |
| gatggtctat catctcgaac tgctgcttac tatcaacagg gtgcgcgttt cgccaaatgg | 420 |
| cgtactgtcg tgagcattcc taacggtccg tctgccctcg ccgtcaaaga agctgcttgg | 480 |
| ggtcttgctc gatacgctgc catttcacag gacagcggtt tggttccgat gttgagcca | 540 |
| gagatcttgt tggatggaga acacgacatt gacagaacat cgacgtagc agagaaggtt | 600 |
| tgggctgagg ttttctttta ccttgctcag aacaatgtca tgtttgaagg tatcctccta | 660 |

| | | | |
|---|---|---|---|
| aaaccgagca | tggtgactcc | cggagctgag | tctaaagaca | gagctactcc | tgaacaagtt | 720 |
| gccgcctaca | ccctcaagct | cctccgcaac | agagtccctc | ccgcagtccc | cggaatcatg | 780 |
| tttttgtccg | gaggacagtc | ggaggtggag | gcaacactca | acttgaacgc | aatgaaccag | 840 |
| gcaccaaacc | catggcacgt | gtccttctcc | tacgcacgtg | cgttgcagaa | cacttgtctg | 900 |
| aaaacatggg | gcggcagacc | cgagaacgtg | aacgcagctc | agaccactct | cttggcccgt | 960 |
| gccaaggcca | attcgttggc | tcagctcgga | aaatacaccg | gtgagggtga | gtccgaagag | 1020 |
| gctaaggagg | gcatgttcgt | caaagggtac | acctattga | | | 1059 |

<210> SEQ ID NO 40
<211> LENGTH: 1062
<212> TYPE: DNA
<213> ORGANISM: Hordeum Vulgare

<400> SEQUENCE: 40

| | | | | | | |
|---|---|---|---|---|---|---|
| gcctccggcg | gctcctacgc | cgacgagctc | gtctccaccg | cgaaaactgt | tgcttcccct | 60 |
| ggccgtggga | tccttgcgat | cgacgagtcg | agtgcaacat | gtggaaagag | attggcatcc | 120 |
| attgggttgg | acaacaccga | agttaaccgc | caggcttaca | ggcagctgtt | gctgaccact | 180 |
| gctggtcttg | gtgaatatat | ctctggtgct | attctctttg | aggaaactct | ctaccagtcc | 240 |
| actacagatg | gcaagacctt | tgttgatgtc | ttgaaggacc | agaatatcat | gcctggtatc | 300 |
| aaggttgaca | agggtttggt | tccattgccc | ggatccaaca | atgaatcctg | gtgccaaggt | 360 |
| cttgatggtt | tggcctcaag | gtgtgctgag | tactacaagc | agggtgcacg | cttcgcaaag | 420 |
| tggcggactg | ttgttagcat | cccttgtggt | cctactgcat | tagctgtcaa | ggaagcggca | 480 |
| tggggacttg | ctcgctatgc | tgctattgct | caggacaatg | gtttagtgcc | aattgtggag | 540 |
| ccagagatcc | tcctcgacgg | tgaccatggc | atcgagagaa | ctcttgaggt | cgccgagaag | 600 |
| gtgtggtccg | aggtgttctt | ctacctggcc | gaaaacaatg | ttcttttga | gggcatcctg | 660 |
| ctgaagccca | gcatggttac | ccctggtgct | gagcacaagg | agaaggcttc | tccagaagcc | 720 |
| attgcgaaga | acaccctcac | aatgctgagg | aggagagtac | cgcccgctgt | ccctggaatc | 780 |
| atgttccttt | ctggcgggca | gtccgaactg | gaggcgacga | tgaacctgaa | cgcgatgaac | 840 |
| cagtccgcca | accgtggca | cgtgtccttc | tcgtacgccc | gggccctcca | gaactcggtg | 900 |
| ctgaagacat | ggcaggggca | gcccgagaac | atcgaggcgg | cgcagaaggc | cctgctggtc | 960 |
| cgcgccaagg | ccaactcgtt | ggcgcagctc | ggcagctaca | cgggcgaggg | cgagagcgac | 1020 |
| gaggccaaga | agggcatgtt | ccagaagggc | tacacctact | ga | | 1062 |

<210> SEQ ID NO 41
<211> LENGTH: 732
<212> TYPE: DNA
<213> ORGANISM: Hordeum vulgare

<400> SEQUENCE: 41

| | | | | | | |
|---|---|---|---|---|---|---|
| gccagcgcgt | acgccgatga | gcttgtgaaa | accgcgaaaa | ccatcgcatc | gcctggcagg | 60 |
| ggtatccttg | ccatggatga | gtcgaatgct | acctgtggca | agagacttgc | ctcgattggc | 120 |
| cttgagaaca | ccgaggctaa | ccgccaggct | taccggaccc | tccttgtcac | tccaccaggc | 180 |
| ttgggaaact | acatctctgg | tgctatcctc | tttgaggaga | ccctctacca | gtcgactgtt | 240 |
| gatggcaaga | agattgttga | catccttgtc | gagcagggga | tcgttcccgg | tatcaaggtt | 300 |
| gacaagggtc | ttgtgccaat | tgttggttcc | aacgatgagt | catggtgcca | aggcctcgat | 360 |
| ggccttgcct | cccgtgaagc | agcatactgc | cagcaaggcg | cccgcttcgc | caagtggcgc | 420 |

```
actgttgtca gcattcctaa cggaccatct gagcttgctg tcaaggaagc tgcctggggt      480
cttgcccgtt acgcggccat ctcacaggac aatgggctgt gccgattgt ggagcctgag       540 atcatgctcg atggtgagca cggcatcgag aggaccttcg aggtggcgca aaggtgtgg       600 gcggagacct tttactacat ggcccagaac aacgtcatgt ttgagggcat cctcctgaag      660
ccaagcatgg tgacccctgg tgccgagtgc aaggacaggg ccaccctga ggaagtagcc      720 agccctcaag tg                                                          732

<210> SEQ ID NO 42
<211> LENGTH: 1056
<212> TYPE: DNA
<213> ORGANISM: Hordeum vulgare

<400> SEQUENCE: 42
gccggcgcct acgacgatga gctcgtcaag acagcgaaaa ccatcgcgtc gccggggcgc       60
ggcatcctgg ccatggacga gtccaacgcc acctgcggga agcgcctcga ctcgatcggc      120
ctggagaaca cggaggccaa ccggcaggcg ttccgcacgc tgctggtctc cgtacctggc      180
ctcggcaacc acatttccgg cgccatcctc ttcgaggaga cgctctacca gtccaccgtc      240
gacggcaaga agattgtcga catcctggca gagcagggca tcgtgcccgg gatcaaggtg      300
gacaaggggc tcgtgccgct caccggctcc aacgacgagt cttggtgtca gggcctcgac      360
ggcctcgcct cccggaggc cgcctactac cagcagggcg cccgcttcgc caagtggcgc      420
accgtggtca gcatccccaa cggcccctcc gagctcgccg tcaaggaggc cgcctggggc      480
ctcgcccgct acgccgccat ctcgcaggac aacggcctgg tgcccatcgt ggagccggag      540
atcctgctgg acggggagca cggcatcggg cgcaccttcg aggtggcgca aaggtgtgg      600 gccgagacat tctaccagat gtcccagaac aacgtcatgt tcgagggcat cctgctcaaa      660
cccagcatgg tcacccctgg cgctgagtgc aaggacaggg ctacgccgga gcaggtggcc      720
ggctacaccc tcaagctcct cagccgccgc gtgccgcccg ccgtcccggg catcatgttc      780
ctgtcgggag gcagtccga ggtggaggcc acgctcaacc tcaacgccat gaaccagggg      840
cccaacccgt ggcacgtctc cttctcctac gccagggcgc tgcagaacac gtgcctcaag      900
acgtggggtg ccgaccggga gaacgtcaag gcggcgcagg aggcgctgtt gctgcgtgcc      960
aaggccaact cgctcgcgca gctcggaaag tacaccagc acggcgaggc cgccgaggcc     1020
aaagagggca tgttcgtcaa aaactacagc tattaa                              1056

<210> SEQ ID NO 43
<211> LENGTH: 1059
<212> TYPE: DNA
<213> ORGANISM: Lycopersicon esculentum

<400> SEQUENCE: 43
gctgctggat cttacaccga tgagctcatc aaaaccgcta aaactattgc ttctcctgga       60
aggggcatcc ttgccattga tgaatcgaat gcaactgccg aaagagact ggcgtcaatt      120 ggtctggaca acacagaagc aaacagacaa gcttaccgtc aactcttgtt gaccactcct      180
ggcctaggtg attacatctc tggatccatt ctattcgaag agacactttt ccagtccact      240
accgatggga agaagtttgt tgatgtcttg cgcgatcaga agattgtacc tggaatcaaa      300
gttgacaagg gtttggttcc cctaccagga tccaacaatg aatcctggtg ccaaggattg      360
gatggattgg cttctaggtc tgctgaatac tacaagcaag gggcacgttt tgccaagtgg      420
agaacagttg ttagcattcc ttgcggtcct tctgctttgg ctgtaaaaga agcagcttgg      480
```

| | |
|---|---|
| ggtcttgctc gatatgctgc tatatctcag dacaatggtt tagtgccaat agtagagcct | 540 |
| gagattcttt tggatggtga ccacccaata gaacgaaccc ttgaagttgc ggaacgtgtt | 600 |
| tgggcagaag tcttctacta cctagcagaa acaatgtcg tttttgaagg tattttgctc | 660 |
| aaacctagca tggttactcc tggtgctgaa cacaaagaga aggctacccc agaaaccatt | 720 |
| gctaaataca cacttaccat gttgaggaga agagttcctc ctgcagttcc tggaatcatg | 780 |
| tttctgtccg gaggacaatc tgaagtgcaa gcgacactca acctccacga aatgaaccag | 840 |
| agccccaacc catggcatgt atctttctca tatgcaagag cactccagaa cacagtgctc | 900 |
| aagacatggc aaggacgtcc tgagaatgtg gatgctgcac agagggcact cttgattcgt | 960 |
| gcaaaagcaa actccttggc tcagctcgga aaatactccg cagaaggtga aagtgaggaa | 1020 |
| gccaagaagg gaatgtttgt caagggctac acctactaa | 1059 |

<210> SEQ ID NO 44
<211> LENGTH: 1056
<212> TYPE: DNA
<213> ORGANISM: Lycopersicon esculentum

<400> SEQUENCE: 44

| | |
|---|---|
| gctagctcct atgctgatga gctcgtcaaa accgcgaaaa ctattgcatc ccctggtcgt | 60 |
| ggaattttgg ccatggatga gtccaatgct acctgtggga agcgtttagc ttcaatcgga | 120 |
| atggagaaca ctgaggctaa ccgccaggcg ttcaggaccc tgctagtttc agttcctgga | 180 |
| ctaggggagt acatctctgg tgcaatcctc tttgaggaga cactttatca atcaaccgtc | 240 |
| gagggaaaga aaatggttga tgtgcttgtt gagcagaaca ttgttcctgg tattaaggtt | 300 |
| gacaagggtc ttgttccttt ggctggctca acaatgaat catggtgcca aggtcttgat | 360 |
| ggccttgcct ctcgctctgc tgcttactac caacaaggcg cccggtttgc caaatggcgt | 420 |
| actgttgtga gcatccctaa tggtccttca gcacttgcag tgaaggaagc agcctggggt | 480 |
| cttgctcgct acgctgctat ttctcaggac aatgggttgg tacccatcgt tgagccagag | 540 |
| atcttacttg atggtgaaca caacattgat aggacctttg aagtcgccaa gcaggtgtgg | 600 |
| gctgaagttt tcttctacct tgcccagaac aatgtcatgt ttgaaggtat cttgttgaag | 660 |
| cccagcatgg tcacccctgg agctgagtgc aaggacaggg ccaccccaca gcaagttgct | 720 |
| gactacaccc tcagtctcct ccgccaaaga atccctcctg ccgtcccagg aatcatgttt | 780 |
| ttgtctggtg dacaatctga agttgaggca actcttaact tgaacgccat gaaccaaagt | 840 |
| cccaacccat ggcacgtgtc gttctcatac gccagagccc ttcagaacac atgcctcaag | 900 |
| acttggagtg aaggccaga aaatgtgaag gcagctcagg atgccttgct tgttagagca | 960 |
| aaggccaact ctcttgccca gctagggaaa tacaccggtg aaggtgagtc cgatgaggcc | 1020 |
| aagaagggaa tgttcgtgaa gggatacgtc tattaa | 1056 |

<210> SEQ ID NO 45
<211> LENGTH: 1056
<212> TYPE: DNA
<213> ORGANISM: Lycopersicon esculentum

<400> SEQUENCE: 45

| | |
|---|---|
| gccagctcct acgctgatga gctcgtcaaa accgcgaaaa ctgttgcatc tcctggtcgt | 60 |
| ggaattttgg cgatggatga gtcgaatgct acctgtggga agcgtttaga ttcaatcgga | 120 |
| ctagagaaca cggaagctaa tcgccaagca tacaggaccc ttcttgtttc agctccagga | 180 |
| cttggtaact acatttcagg tgccatcctt tttgaggaga cactttacca gtccactgtt | 240 |

```
gatggaaaga aaattgttga tgtacttctt gaacagaaca ttgttcctgg aattaaggtt      300
gacaagggtt tagttccttt ggctggttca acaatgaat cttggtgcca aggtcttgat       360
ggccttgcct cgcgctctgc tgcttactac caacaaggcg ctcgttttgc taaatggcgt      420
actgtagtga gcattcccaa tggtccttct gcacttgcag ttaaggaggc agcctggggt      480
cttgctcgct atgctgcaat ttctcaggac aatgggttag taccaattgt tgagccagag     540
attttgctag atggtgaaca caatatcgat aggacctttg aggttgctca acaggtgtgg     600
gctgaagttt tcttctacct ggccgaaaac aatgtcatgt ttgaaggtat cttgttgaag    660
cctagcatgg tcaccccggg agcagaatgc aaggagaggg ccaccccaga acaagttgct    720
gattataccc tcaagctcct ccaacgaaga attcccctg ctgtccctgg aatcatgttc      780
ttgtctggtg gacaatctga agtggaagct actcttaact tgaacgcgat gaaccaatct    840
cccaacccat ggcacgtatc gttctcatat gcaagagccc ttcagaacac atgtctcaag    900
acatggggtg gaagaccaga aaatgttgag gcagctcaga aagctttgct tactagagca     960
agtgccaact ctctcgcgca actaggcaaa tacaccggtg aaggtgagtc tgaggaggcc   1020
aaggagggaa tgtttgtgaa aggatatgtc tactaa                              1056
```

<210> SEQ ID NO 46
<211> LENGTH: 1017
<212> TYPE: DNA
<213> ORGANISM: Lotus japonicus

<400> SEQUENCE: 46

```
aaaactattg cgtctcctgg tcgtggaata cttgcaattg atgagtcaaa cgcgaccgct      60
gggaagcgtt tggcatcgat tggattggac aacacgagaa ccaatcgcca ggcctacagg    120
caacttctgc tgaccacacc tggccttggt gaatacatct ctggtgccat ttttttcgag    180
gaaacccttt accagtcaac cactgatgga agaagtttg tggactgtct tcgtgaggag     240
aacattgtac ctggaatcaa agttgataag ggtttggtcc tctgccaggg gtcaaacaat  300
gaatcttggt gccaagggtt ggatggattg gcttcaagat ctgctgaata ctacaagcaa   360
ggtgctagat ttgccaagtg gaggacagtt gtcagcattc cttgtggtcc ttctgcattg   420
gccgttaagg aagcagcatg gggacttgca cgttacgctg ctatctctca ggacaatggc   480
cttgttccaa ttgtagagcc tgaaattctt cttgatgggg accacccaat cgagaggaca    540
ttggaagtgg ccgagaaggt ctggtctgaa gtcttcttct atttggctga aaacaatgtc   600
gtttttgagg gaatttgct caaacctagc atggttacgc ctggagcgga acacaagcaa    660
aaggcttctc cagaaactat tgccaataac acactaacca tgcttagaag gagagttcct    720
ccagcagtcc ctgaatcat gtttctgtcg ggtggacaat ctgaagtgga agccacacta    780
aatctcaatg ctatgaacca aagtccaaac ccatggcatg tttcgttctc gtatgcaaga    840
gctctgcaga cactgtgct taagacttgg caaggacgcc ctgaaaatgt ggaagctgcg     900
cagaagtctc tcttgatccg cgctaaagca aactccttgg ctcaacttgg aagatactct    960
gctgagggtg aaagtgaaga agcacagaaa ggaatgtttg tcaagggcta cacctac     1017
```

<210> SEQ ID NO 47
<211> LENGTH: 1056
<212> TYPE: DNA
<213> ORGANISM: Lotus japonicus

<400> SEQUENCE: 47

```
gctggttcct atgctgatga gcttgttaag actgcgaaaa ctgttgcttc accagggcgt      60
```

```
ggtattttgg ccatggatga gtcaaatgct acctgtggga agcgtttggc ttcaattggg    120
ctagagaaca ccgaagttaa ccgccaagca taccgtactc ttcttgtgtc tgctccaggc    180
cttggccagt acatctctgg tgccattctc tttgaggaaa ctctctacca atccacaact    240
gatggcagga agattgttga tgtacttatt gaacagaaca tcgttcctgg tattaaagtt    300
gacaagggtt tggtaccact ggctggttcc aatgatgaat catggtgcca aggtctggat    360
ggtcttgcct ctcgctcagc agcatactac caacaaggtg cccgattcgc caaatggcgt    420
accgttgtga gcatccccaa cggtcccact gctttggcag ttaaggaagc agcctggggt    480
ctggctcgtt atgctgcaat ttctcaggac aatgggctag ttccaattgt ggagcctgag    540
atcctgcttg acggtgagca tgatattgaa aggacttttg aggtagccca aaaggtgtgg    600
gctgaggttt tcttctacct tgctgagaac aatgtcctgt ttgagggtat tctcctcaag    660
cctagcatgg ttacccctgg agctgagagc aaggacaagg tctctcctca gacggtttct    720
gattacaccc tcaagctcct taaaaggaga attccccctg ctgtccctgg aatcatgttt    780
ttgtctggtg acaatctgga ggttgaagca accctgaact tgaatgccat gaaccaatct    840
ccaaacccat ggcatgtgtc gttctcgttt gcaagagctc tccaaaatac cgccttgaag    900
acatgggggg gtcgcgcgga aacgtgaag gcagcacaag atgcactcct tttccgtgct    960
aagagcaact cactggctca gcttgggaag tacaatggtg atggtgaatc tgaggaggcc   1020
aagaaggagt tgttcgtcaa aggatactcc tattaa                             1056

<210> SEQ ID NO 48
<211> LENGTH: 1056
<212> TYPE: DNA
<213> ORGANISM: Lotus japonicus

<400> SEQUENCE: 48
gctggttcct atgctgatga gcttgttaag actgcgaaaa ctgttgcttc accagggcgt     60
ggcattttgg ccatggatga gtccaatgct acctgtggga agcgtttggc ttcaattggg    120
ctagagaaca ccgaagttaa ccgccaagca tggcgtactc ttcttgtgac tgctcctggc    180
cttggtcagt acgtctctgg ggccattctc tttgaagaaa ctctctacca atccacaacc    240
gatggcagga agattgttga tgttcttatt gagcaaaaca tcgttcccgg tattaaagtt    300
gacaagggtt tggtgcccct ggctggttcc aatgatgagt catggtgtca aggtctggat    360
ggtcttgcct ctcgcacagc tgcatactac cagcaaggtg cccgattcgc caaatggcgt    420
actgttgtga gcatccccaa cggtcccact gctttggcag ttaaggaagc agcttggggt    480
ctggctcgtt atgctgcaat tgctcaggac aatgggctag tcccaattgt ggagcctgag    540
atcctgcttg atggtgaaca tggtattgaa aggacttttg aagtagccca aaaggtttgg    600
gctgaggttt tcttctacct tgctgagaac aatgtcttgt ttgagggtat tctcctcaag    660
cctagcatgg ttacccctgg agctgagagc aaggataagg tctctcctca gcaagtttct    720
gattacaccc tcaagctcct tcagaggaga attcccccag ctgtccctgg aatcatgttt    780
ttgtcaggag acaatctgga ggttgaagca accctgaact tgaatgccat gaaccaatct    840
ccaaacccat ggcatgtgtc attctcarttt gccagagctc tccaaaacac cgccttgaag    900
acatgggggg gccgcgcaga gaatgtgaag gcagcacaag atgcactcct tttccgcgct    960
aagagcaact cattggctca gcttggaaag tacactggtg atggtgaatc tgaggaagcc   1020
aagaaggagt tgttcgtcaa aggctactcc tattaa                             1056

<210> SEQ ID NO 49
```

<211> LENGTH: 1062
<212> TYPE: DNA
<213> ORGANISM: Oryza sativa

<400> SEQUENCE: 49

| | | | | | |
|---|---|---|---|---|---|
| gccgccgccg | tctcctacgc | cgacgagctc | gtctccaccg | cgaaatctgt | tgcttcccca | 60 |
| gggcgtggta | tcctggcaat | tgatgagtcg | aatgccacat | gcggaaagag | attagcatcc | 120 |
| attggtttgg | acaacacaga | agttaaccgc | caggcttaca | ggcagctttt | actgaccact | 180 |
| gctggtcttg | gtgaatatat | ttctggtgct | atccttttg | aggaaactct | ttatcagtca | 240 |
| accactgatg | gtaagaagtt | tgttgactgc | ttgaaggatc | agaatatcat | gcccggtatc | 300 |
| aaggtcgaca | agggcttggt | tccattgcct | gggtccaaca | atgaatcttg | gtgccaaggc | 360 |
| ctagatggtt | tggcttcaag | gtgtgctgag | tactacaagc | aggggggcacg | cttcgctaag | 420 |
| tggcggactg | ttgttagcat | cccttgtggt | ccctcagcat | tagcagtcaa | ggaagcggca | 480 |
| tggggacttg | ctcgatatgc | tgccattgct | caggacaatg | gcttagtgcc | aattgttgag | 540 |
| ccagagatcc | ttcttgatgg | tgaccatgcg | atcgagagaa | ctcttgaagt | ggcagagaaa | 600 |
| gtgtggtctg | aggtattctt | ctacctggcc | caaaacaatg | ttctttttga | gggtatcctg | 660 |
| ctgaaaccca | gcatggtgac | ccctggagct | gaacacaagc | agaaggccac | tccagaagcc | 720 |
| attgcgaagc | acacccttac | aatgctgagg | aggagagtgc | cgcctgctgt | ccctggaatc | 780 |
| atgttccttt | ctggtgggca | atctgaggtg | gaggcaaccc | tgaacctgaa | cgcgatgaac | 840 |
| caagaaccaa | acccatggca | tgtgtccttc | tcatacgccc | gggctctcca | gaactcggtg | 900 |
| ctgaagacat | ggcaggggcg | ccccgagaac | gtggaggcag | cgcagaaggc | actgctggtc | 960 |
| cgtgccaagg | cgaactcgct | ggctcagctc | ggtcgctaca | ccggcgaggg | cgagagcgat | 1020 |
| gaggccaaga | agggaatgtt | ccagaagggc | tacacttact | ga | | 1062 |

<210> SEQ ID NO 50
<211> LENGTH: 1056
<212> TYPE: DNA
<213> ORGANISM: Oryza sativa

<400> SEQUENCE: 50

| | | | | | |
|---|---|---|---|---|---|
| gctggtgcct | acgacgatga | gcttgtcaag | accgcgaaaa | ccattgcatc | accaggaagg | 60 |
| ggtatccttg | ccatggatga | gtcgaacgcg | acctgccgta | agaggcttgc | gtcaattggc | 120 |
| cttgagaaca | ccgaggccaa | ccgccaggct | taccggaccc | tccttgtcac | cgcaccgggc | 180 |
| ttgggacagt | acatctccgg | tgctatcctc | ttcgaggaga | ctctgtacca | gtcaactgta | 240 |
| gatggcaaga | agattgtcga | catcctcact | gagcagaaaa | tcgttccagg | tatcaaggtc | 300 |
| gacaagggtc | ttgtgcccct | tgctggctcc | aacaacgagt | catggtgcca | aggtctcgac | 360 |
| ggccttgcct | cgcgcgaggc | ggcatactac | cagcagggcg | ctcgcttcgc | caagtggcgc | 420 |
| actgttgtca | gcatccccaa | cggcccatct | gaactcgccg | tgaaggaggc | tgcctggggc | 480 |
| cttgcccgct | acgccgccat | ttctcaggac | aacgggctgg | tgccgattgt | cgagcctgag | 540 |
| atcctcctcg | acggtgagca | tggcatcgac | aggaccttcg | aggtggcgca | gaaggtgtgg | 600 |
| gcggagacct | tcttctacat | ggccgagaac | aatgtgatgt | tcgagggcat | cctcctcaag | 660 |
| ccaagcatgg | tgacacccgg | tgccgagtgc | aaggacaggg | ccacccctga | gcaagtatct | 720 |
| gactacaccc | tcaagctcct | ccacagaagg | atccccccctg | ccgtccccgg | catcatgttc | 780 |
| ttgtcgggtg | ggcagtcgga | ggtggaggcg | acgcagaacc | tgaacgcgat | gaaccagggg | 840 |
| cccaacccgt | ggcacgtgtc | gttctcgtac | gcgagggcgc | tgcagaacac | gtgcctcaag | 900 |

| | | | | | |
|---|---|---|---|---|---|
| acgtggggcg | gcagccgga | gaacgtgaag | gcggcgcagg | acgcgctgct | cctccgcgcc | 960 |
| aaggccaact | cgctggcgca | gctcggcaag | tacaccagcg | acggcgaggc | cgccgaggcc | 1020 |
| aaggagggca | tgttcgtcaa | gaactacgtc | tactaa | | | 1056 |

<210> SEQ ID NO 51
<211> LENGTH: 1056
<212> TYPE: DNA
<213> ORGANISM: Picea sitchensis

<400> SEQUENCE: 51

| | | | | | |
|---|---|---|---|---|---|
| gccggatcgt | atgccgagga | gcttgttcaa | accgcgaaaa | ctgttgcatc | tcctggtcgt | 60 |
| ggtattcttg | ccatagatga | gtccaatgcc | acttgtggga | agaggcttgc | ttccattgga | 120 |
| ctcgaaaaca | atgaaaccaa | ccgccaagca | tacagacaac | tcttgttgac | acaccagga | 180 |
| cttggggaat | atatttccgg | ttccatcctt | tttgaagaaa | ccctctacca | gtccacaact | 240 |
| gatggagga | aatttgttga | ttgtttgcgc | gagcagaata | ttatgcctgg | catcaaagtt | 300 |
| gacaagggtt | tagtcccatt | gccaggatca | acaatgaat | cttggtgcca | gggtctggat | 360 |
| ggattagcct | caagatctgc | cgagtactac | aaacagggtg | caagatttgc | taaatggcga | 420 |
| actgttgtca | gcataccaaa | cgggccatct | gacttagctg | tcaaggaagc | tgcctggga | 480 |
| cttgcacgtt | atgctgccat | ttctcaggac | aatggtcttg | tgcccattgt | ggagccagag | 540 |
| attcttctgg | atggagacca | ttccattgat | agaacccttg | aagtggcaga | gaaagtctgg | 600 |
| gctgaagttt | tcttctactt | ggcagagaac | aatgtgtttt | tcgagggtat | tttgttaaag | 660 |
| cccagtatgg | tgactcctgg | tgctgagcac | aaggagaaag | caacccccaca | acaggttgca | 720 |
| gattacactc | ttaaaatgct | caagaggagg | gtgccaccag | ctgttcctgg | gattatgttc | 780 |
| ttgtctggag | acagtccga | ggttgaggca | actttgaatt | tgaatgcaat | gaaccaaagc | 840 |
| ccaaatccat | ggcatgtttc | cttttcatat | gcacgagcct | tgcagaacac | atctctcaag | 900 |
| acctggaagg | gtctcccaga | gaatattgaa | gcagctcaga | gggcacttct | tattcgtgcc | 960 |
| aaggctaatt | ctctggccca | gcttgggcga | tactccgctg | aaggtgaaag | tgaggagtcc | 1020 |
| aagaagggaa | tgtttgtcaa | gggatacaca | tattaa | | | 1056 |

<210> SEQ ID NO 52
<211> LENGTH: 1056
<212> TYPE: DNA
<213> ORGANISM: Picea sitchensis

<400> SEQUENCE: 52

| | | | | | |
|---|---|---|---|---|---|
| gccggggctt | acagcgaaga | actcatcaag | acggcgaaaa | gagtggcgtc | tccggggaga | 60 |
| ggcatcctgg | cgatggacga | gtccaacgct | acctgcggca | aacggctggc | gtccatcggg | 120 |
| ctggagaaca | cggaggcgaa | ccgccaggca | tacaggcagc | ttctcgtcag | cgctcccggc | 180 |
| ctgggacagt | acatctccgg | ctccattctc | ttcgaggaga | ccctctacca | gtccacgacc | 240 |
| gacggcaaga | agatggtaga | tgtcctcgtg | cagcaggaca | tagtccccgg | catcaaagtt | 300 |
| gacaagggtt | tggttccttt | ggctggctca | aacgacgaat | cttggtgcca | aggcctagac | 360 |
| ggcctcgcat | cgaggtgcgc | tgcatattac | cagcagggtg | cccgcttcgc | taaatggcgt | 420 |
| accgttgtga | gcattcccaa | cggcccctct | gctctggccg | tgaaagaagc | tgcatggggt | 480 |
| ctcgcccgct | acgcggcaat | tgctcaggac | aacggtctgg | ttcccatagt | ggagccggag | 540 |
| atcctgttgg | acggagagca | cggccttgag | aggactttg | aagtagcgct | gaaggtttgg | 600 |
| gccgaggtgt | tcttctactt | agctgagaac | aacgtgctgt | tcgaaggcat | tctgctgaag | 660 |

```
ccgagcatgg ttaccccagg tgccgagtgc aaggacaggg caagcccaga aactgttgcc      720
caatatactc tcaaccttct tcgaagaaga gttccaccag ctgttcctgg tatcatgttc      780
ttgtctggtg ggcaatctga ggtggaggcg acgttgaact tgaacgcgat gaaccaggcg      840
ccgaacccgt ggcacgtatc attctcatac gctcgtgcac tgcaaaatac atgcttaaag      900
acatgggctg gcaggcccga aaacgtggac gcagcccaga agatcctgtt ggttcgggca      960
aaggccaact cccttgcaca gctcggcaaa tactctgctg aaggcgagtc tgcagagtcg     1020
aaggagggaa tgttcgtgaa gggctacact tactaa                               1056
```

```
<210> SEQ ID NO 53
<211> LENGTH: 1056
<212> TYPE: DNA
<213> ORGANISM: Populus trichocarpa

<400> SEQUENCE: 53
gccaactctt acactgacga gctcgtccaa accgctaaaa ctattgcatc acctggtcgt       60
ggtatccttg ccatagacga atcaaatgca acctgtggga agaggttggc atctattggc      120
ttggataaca ccgaaaccaa ccgacaagca tacagacaac ttttattgac tactcctagt      180
cttggcgaat acatttctgg tgccattctt ttcgaggaga cactttacca gtctacaact      240
gatggaaaga agttcgtgga ttgcctgcgt gatgagaaca ttgtacctgg catcaaagtt      300
gacaagggtt tagtccccct accaggttca aacaacgagt cttggtgcca aggtttggat      360
ggattggctt caagatctgc tgaatattac aagcaaggtg cacgttttgc taagtggagg      420
actgttgtca gcattccctg tggcccttct gctctggctg tcaaggaagc tgcatgggga      480
cttgcacgat atgctgccat ttctcaggat aacggtcttg tgcccatagt tgagcctgag      540
attctacttg atggggacca tccaattgac aggaccettg aagttgctga aaggtctgg      600 tcaggagtct tttactattt ggctgaaaac aatgttgtgt ttgagggcat cctacttaag      660
cctagcatgg taacgccagg ggctgaacac aaggagaagg catcagcaga taccatagcc      720
aaatatacac ttacgatgct taaaaggaga gtacctcctg cagttcctgg tatcatgttt      780
ttgtctggag ggcaatctga agtgcaagca accctcaacc tcaatgcaat gaaccaaagc      840
cccaacccat ggcatgtttc cttctcatat gcacgtgcac tgcagaacac cgtgctcaag      900
acatggcaag gacgccctga taacgtggaa gctgctcaga gtcactttt ggtgcgtgcc      960 aaggctaact ccttggctca gcttggaagg tattctgccg agggtgaaag cgaggaagct     1020
acgaagggaa tgttcgtaaa gggctatacc tattga                               1056
```

```
<210> SEQ ID NO 54
<211> LENGTH: 1056
<212> TYPE: DNA
<213> ORGANISM: Populus trichocarpa

<400> SEQUENCE: 54
gctggttctt atgctgatga gcttgtcaag accgcgaaaa ccattgcatc tcctggtcgt       60
ggtattttgg ccatggacga gtccaatgct acctgtggga aacgtctagc ctcaattggg      120
ctagagaaca ctgaggctaa ccgccaggca taccgaaccc ttcttgtgac agtccctggt      180
cttggcaatt acgtctctgg tgccatcctt tttgaggaga ctctctacca atccacaact      240
gatggcaaga agatggttga tgttcttgtt gagcagaaga ttgttcctgg tatcaaagtc      300
gacaagggtt tggtgcctct agctggtcc aatgacgagt cgtggtgcca aggtcttgat      360
ggacttgcct cccgctcagc tgcttactac cagcagggtg ctcgtttcgc caaatggcgt      420
```

```
actgttgtga gcattcccaa cggcccatct gccttggcag tgaaggaggc tgcctggggt    480
cttgcccgct atgctgccat ttctcaagac aacggattgg tccctattgt ggagccagaa    540
atcttacttg atggcgagca tggcattgag aggacttttg aagtagccca gaaggtgtgg    600
gctgaggttt tctactacat ggcagagaac aatgtcatgt ttgagggtat cctcctcaag    660
cctagtatgg tcactcctgg cgctgaatgc aaggacaggg cctcccctga ccaagttgct    720
gaatacaccc tcaagctcct ccacaggaga atccccccag ccgtccctgg aatcatgttt    780
ttgtctggtg ggcaatctga ggtcgaagca accctgaacc tcaacgcaat gaaccaatct    840
ccaaacccat ggcacgtgtc attctcatat gccagagctc tccagaacac ttgtttgaaa    900
acatggggag gcaggccaga gaacgttcag gatgctcagg aaacacttct catccgtgcc    960
aaggccaact ctcttgctca gcttggcaag tacaccggtg aaggagagtc agatgatgcc    1020
aagaaaggaa tgtacgtcaa gaactactcc tactaa                              1056
```

<210> SEQ ID NO 55
<211> LENGTH: 1056
<212> TYPE: DNA
<213> ORGANISM: Populus trichocarpa

<400> SEQUENCE: 55

```
actggttcct atgctgagga gcttgtcaaa ccgcgaaaa ctattgcatc tcctggccga     60
ggtattttgg ccatggatga gtctaacgct acctgtggaa aacgtctcgc tcaatcggg    120 ctagagaaca ccgaggctaa ccgccaggca taccgtaccc ttcttgtgac agtccctggc    180
cttggtgatt acgtctctgg tgccatcctt tttgaggaga ctctctacca atccaccact    240
gatggcaaga gatggttga tgttcttgtt gagcaaaaga ttgttcccgg catcaaagtt     300
gacaagggtt tggtgcctct agctggttcc aatgatgagt catggtgcca aggtcttgat    360
ggactcgcct cccgcacagc tgcttactac aacagggag ctcgttttgc caaatggcgt     420
actgttgtga gcattcccaa cggcccatct gccttggcag tgaaggaggc tgcctggggt    480
cttgcccgct atgctgccat ttctcaagac aatggattgg tcccaattgt ggagccagaa    540
atcttgcttg atggtgagca tggcattgac aggactttcg aagtagccca gaaggtttgg    600
gctgaggttt tcttctacat ggcagagaac aatgtcatgt ttgagggtat tcttctcaag    660
cctagtatgg tcactcctgg tgctgaatgc aaggacaggg ccaccctga caagttgct    720 gagtacacac tcaagctcct tcagaggaga atccccccat ccgtccctgg aatcatgttt    780
ttgtctggtg ggcaatccga ggttaagca accctgaacc tcaacgcaat gaaccagtct    840
gcaaacccat ggcacgtgtc tttctcatat gctagagctc tccagaacac ttgcttgaag    900
acatggggag gcaggccaga gaacgtgaat gcagctcagg aagcacttct catccgtgcc    960
aaggccaact ctcttgctca gcttggcaag tacaccggtg agggagagtc agatgaagcc    1020
aagaaaggaa tgttcgtcaa gaactacgcc tactaa                              1056
```

<210> SEQ ID NO 56
<211> LENGTH: 738
<212> TYPE: DNA
<213> ORGANISM: Zea mays

<400> SEQUENCE: 56

```
cacgagggtt ccaacaatga atcgtggtgc caaggtcttg atggtttggc ttcaaggtgt     60
gctgagtact ataagcaggg ggcccgcttc gcaaagtgga ggactgttgt tagcatccct    120
tgtggtccat ctgcattagc agtgaaggaa gcagcatggg gacttgctcg atatgctgct    180
```

-continued

```
attgctcagg ataatggctt agtgccaatt gtggagccag agatccttct tgatggagac    240
catgggatcg aaagaactct tgaggtggca gagaaagtgt ggtctgaggt gttcttctac    300
ttggcccaga acaatgttct gtttgagggt atcctgctga agcccagcat ggtcactcct    360
ggagccgacc acaaggagaa ggcttctcca gaagccatcg caaagtacac gctaacaatg    420
ctcaggagga gagtgcctcc ggctgttcct ggaatcatgt tcctttctgg tgggcagtcc    480
gaggtggagg cgactctgaa cctgaatgcg atgaaccagt ctccgaaccc atggcacgta    540
tcattctcct acgcccgggc tctgcagaac tcggtgctga agacatggca agggcgcccc    600
gagaacgttg aggcggcgca aaaggccctg ctggtgcgcg caaaggccaa ctcgctggca    660
cagctaggtc gctacactgg tgagggtgag agcgacgagg cgaagaaagg catgttccag    720
aagggctaca cctactaa                                                  738
```